(12) United States Patent
Stojiljkovic et al.

(10) Patent No.: US 7,026,157 B1
(45) Date of Patent: Apr. 11, 2006

(54) BACTERIAL HEMOGLOBIN RECEPTOR GENES

(75) Inventors: Igor Stojiljkovic, Portland, OR (US); Magdalene So, Portland, OR (US); Vivian Hwa, Portland, OR (US); Fred Heffron, West Linn, OR (US); Xavier Nassif, Paris (FR)

(73) Assignee: Oregon Health and Science University, Portland, OR (US)

( * ) Notice: Subject to any disclaimer, the term of this patent is extended or adjusted under 35 U.S.C. 154(b) by 501 days.

(21) Appl. No.: 09/665,358

(22) Filed: Sep. 19, 2000

Related U.S. Application Data

(63) Continuation of application No. 08/537,361, filed on Oct. 2, 1995, now Pat. No. 6,121,037, which is a continuation-in-part of application No. 08/326,670, filed on Oct. 18, 1994, now Pat. No. 5,698,438.

(51) Int. Cl.
  C12N 1/21 (2006.01)
  C12N 15/31 (2006.01)
  C12N 15/63 (2006.01)
  C12N 15/74 (2006.01)

(52) U.S. Cl. ............................ 435/252.3; 435/320.1; 536/23.7

(58) Field of Classification Search ............ 435/252.3, 435/320.1; 536/23.7, 23.1; 935/11
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis et al. |
| 5,223,409 A | 6/1993 | Ladner et al. |
| 5,304,487 A | 4/1994 | Wilding et al. |
| 6,121,037 A | 9/2000 | Stojiljkovic et al. |

OTHER PUBLICATIONS

Archibald and DeVoe, (1979) FEMS Mirocbiol. Lett., 6, pp. 159-162.
Baggs amd Neilands, (1991), Microbiol. Rev., 51:509-518.
Calver et al., (1976) Can. J. Microbiol., 22, 832-838.
Cornelissen et al., (1993) J. Bacteriol., 174: pp. 5788-5797.
Correia et al., (1988) J. Biol. Chem., 263: 12194-12198.
Coulton and Pang, (1983) Curr. Microbiol., 9: pp. 93-98.
Dyer et al., (1987) Infect. Immun., 55: pp. 2171-2175.
Fenno et al., (1993) Gene, 130: 81-90.
Gerlach et al., (1992) Infect. Immun., 60: 3253-3261.
Gotschlich et al., (1987) J. Exp. Med., 165: pp. 471-482.
Heller et al., (1988) Gene, 64: pp. 147-153.
Henderson and Payne, (1994) J. Bacteriol, 176: pp. 3269-3277.
Hnatowich et al., (1983) Science, 220: pp. 613-615.
Holbien et al., (1981) Infect. Immun., 34: 120-125.
Jarosik et al., (1994) Infect. Immun., 62: pp. 2470-2477.
Kellog et al., (1963) J. Bacteriol., 85: 1274-1279.
Knight et al., (1992) Mol. Microbiol., 6: pp. 1565-1573.
Koebnik et al., (1993) Trends Microbiol., 6: pp. 1565-1573.
Lee and Hill, (1992) J. Gen. Microbiol., 138: 2647-2656.
Lee, (1994) Microbiol., 140: 1473-1480.
Lundrigan & Kadner, (1986) J. Biol. Chem., 261: pp. 10797-10801.
Martek and Lee, (1994) Infect. Immun., 62: 700-703.
Meares et al., (1984) Anal. Biochem., 142: 68-78.
Mickelson et al., (1982) Infect. Immun., 35: pp. 915-920.
Nassif et al., (1993) Mol. Microbiol., 6: pp. 719-725.
Otto et al., (1992) Crit. Rev. Microbiol., 18:217-233.
Pettersson et al., (1993) Infect. Immun., 61: 4724-4733.
Pettersson et al., (1994) J. Bacteriol 176:pp. 1764-1766.
Postle, (1990) Mol. Microbiol., 133: pp. 891-898.
Riboli et al., (1991) Microb. Pathogen., 10: pp. 393-403.
Rudinger, Jun. 1976, Peptide Hormones, pp. 1-7.
Saiki et al., (1988) Science, 230: 1350-1354.
Schoffler and Braun, Molec. Gen. Genet., 217: pp. 378-383.
Schryvers and Morris, (1988) Infect. Immun., 56: pp. 1144-1149.
Schryvers and Morris, (1988) Mol. Microbiol., 2: 281-288.
Schryvers et al., (1989) Infect. Immun., 57(8): pp. 2425-2429.
Stojilkovic et al., (1995) Mol. Microbiol. 15:pp. 531-541.
Stroebner and Payne, (1988) Infec. Immun., 56: pp. 2891-2895.
Struyve et al., (1991) J. Mol. Biol., 218: 141-148.
Walters, (1993) *Pharmaceutical Biotechnology*, pp. 165-174.
Weinberg. (1984) Physiological Rev., 64: pp. 65-102.
West and Sparling, (1985) Infect. Immun., 47: pp. 288-294.

*Primary Examiner*—Robert C. Hayes
(74) *Attorney, Agent, or Firm*—McDonnell Boehnen Hulbert & Berghoff

(57) ABSTRACT

The present invention relates to novel bacterial hemoglobin receptor proteins and genes that encode such proteins. The invention is directed toward the isolation, characterization, diagnostic and therapeutic use of bacterial hemoglobin receptor proteins, nucleic acid encoding such proteins, recombinant expression constructs comprising such nucleic acids and cells transformed therewith, and antibodies and epitopes of such hemoglobin receptor proteins. The invention relates particularly to hemoglobin receptor proteins and genes encoding such proteins from *Neisseria* species, especially *N. meningitidis* and serotypes thereof, and *N. gonorrhoeae*. Methods for the diagnostic and therapeutic use of the proteins, epitopes, antibodies and nucleic acids of the invention are also provided, including the use of the proteins, epitopes, antibodies and nucleic acids of the invention for the production of vaccines effectinve in providing immunization of a human against infection by pathogenic bacteria of *Neisseria* species.

3 Claims, 47 Drawing Sheets

FIG. 2A

Figure 1:
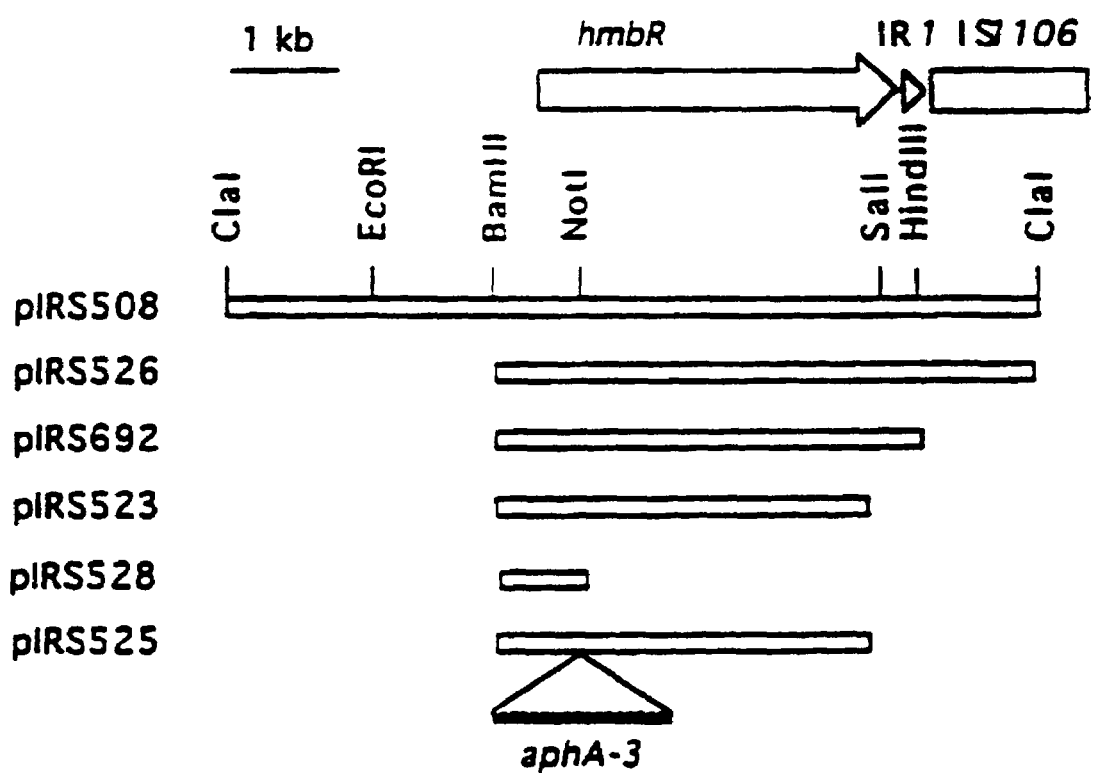

```
AGAACTAGTGGATCCAATTTGGGCGCGGCGTTTTGTTCAAACACGCCCAAAAACTCGAT         60
            BamHI
TACAAACGGCGAACACGGGCGCGGCGCCACCTCGCTCCCGCATCCCGGACGGGCCGCAAACA
                                        160
CTGGGCGCGCCCTTCGTCGAGCATCTGAACGCTTTGAACCTGACTCCCGAAGCCGAAGCGGA
                                   210
AGCCATTCAAGGGCGCGCCGAAGCCCTTGCATTCTACAAAGTCGTGTTGCGCGAAACCTT
                260
CGGCTTGGCAGCCGATGCCCCCGAAGGTATGATGCCCGAACAGGCACTAAAAAAAT         360
AATCGAACCAAATAAACAAGGTCTCGGCATAGCTGTTTGCAGGGACCCTTTAATTACACGG
                                                    410
CGCGGCTTTGTTTACATGGATTACTGTCTTATTAAATATTAATGATTATCATAAAATCTA
                                    -10      Fur-box
TTATTCGCTAACCGATGAACAATCCATACATCTTGAGTTGATAATATGAAACCATT
                                        SD        MetLysProLe
```

FIG. 2B

```
         510                                    560                                    610
ACAAATGCTCTCCCTATCGGCCCGCCTGGTCGGCAGTATTTTCGGCAATCCGGTCTTTGCGGC
 u Gln Met Leu Pro Ile Ala Ala Leu Val Gly Ser Ile Phe Gly Asn Pro Val Phe Ala Ala

AGATGAAGCTGCAACTGAAACCACACCCGTTAAGGCAGAGGTAAAAGCAGTGCGCGTTAA
 a Asp Glu Ala Ala Thr Glu Thr Thr Pro Val Lys Ala Glu Val Val Lys Ala Val Arg Val Ly
                          610                                    660

AGGCCAGCGCAATGCGCCTGCGGCTGTGGAACGCGTCAACCTTAACCGTATCAAACAAGA
 s Gly Gln Arg Asn Ala Pro Ala Ala Val Glu Arg Val Ala Asn Leu Asn Arg Ile Lys Gln Gl
                                                      710

AATGATACGCGACAACAAAGACTTGGTGCGCTATTCCACCGATGTCGGCTTGAGCGACAG
 u Met Ile Arg Asp Asn Lys Asp Leu Val Arg Tyr Ser Thr Asp Val Gly Leu Ser Asp Se
                          760

CGGCCGCCATCAAAAAGGCTTTGCTGTTCGCGGCGTGGAAGGCAACCGTGTCGGCGTGAG
 r Gly Arg His Gln Lys Gly Phe Ala Val Arg Gly Val Glu Gly Asn Arg Val Gly Val Se
                                                      810

CATAGACGGCGTAAACCTGCCTGATTCCGAAGAAAACTCGCTGTACGCCCGTTATGGCAA
 r Ile Asp Gly Val Asn Leu Pro Asp Ser Glu Glu Asn Ser Leu Tyr Ala Arg Tyr Gly As
                          860

CTTCAACAGTCGCGTCTGTCTATCGACCCCGAACTCGTGCGCAACATCGACATCGTAAAA
 n Phe Asn Ser Arg Leu Ser Ile Asp Pro Glu Leu Val Arg Asn Ile Asp Ile Val Lys
```

FIG. 2C

```
        910                                                                                    960
         |                                                                                     |
AGGGGCGGACTCTTTCAATACCGGCAGCGGCCCTTGGGCGGCCGGTGTGAATTACCAAAC
sGlyAlaAspSerPheAsnThrGlySerGlyAlaLeuGlyGlyGlyValAsnTyrGlnTh
                                                                                         1010

CCTGCAAGGACGTGACTTACTGTTGCCTGAACCGGCAGTTCGGCCGTGATGATGAAAACGG
rLeuGlnGlyArgAspLeuLeuProGluArgGlnPheGlyValMetMetLysAsnGl
                                            1060

TTACAGCACGCGTAACCGTGAATGGACAAATACCCTCGGTTTCGGCGTGAGCAACGACCG
yTyrSerThrArgAsnArgGluTrpThrAsnThrLeuGlyPheGlyValSerAsnAspAr
                                1110

CGTGGATGCCGCTTTGCTGTATTCCGCAACGGCCGGCCATGAAACTGAAAGCGCGGGCAA
gValAspAlaAlaLeuLeuTyrSerGlnArgArgGlyHisGluThrGluSerAlaGlyLy
                      1160

GCGTGGTTATCCGGTAGAGGGTGCTGGTAGCGGGAGCCGAATATCCGTGGTTCTGCCGCGG
sArgGlyTyrProValGluGlyAlaGlySerGlyAlaAsnIleArgGlySerAlaArgGl
              1210                                              1260

TATTCCTGATCCGTCCCAACACAAATACCACAGCTTCTTGGGTAAGATTGCTTATCAAAT
yIleProAspProSerGlnHisLysTyrHisSerPheLeuGlyLysIleAlaTyrGlnIl
  1210                                     1310

CAACGACAACCACCGCATCGGCGCTCAACGGTCAGCAGGGGCATAATTACACCGGT
eAsnAspAsnHisArgIleGlyAlaSerLeuAsnGlyGlnGlyHisAsnTyrThrVa
```

FIG. 2D

```
TGAAGAGTCTTACAACCTGCTTGCTTCTTATTGGCGTGAAGCTGACGATGTCAACAGACG
 GluSerTyrAsnLeuLeuAlaSerTyrTrpArgGluAlaAspValAsnArgAr
                        1410
GCGTAACACCAACCTCTTTTACGAATGGACGCCGGAATCCGACCGGTTGTCTATGGTAAA
gArgAsnThrAsnLeuPheTyrGluTrpThrProGluSerAspArgLeuSerMetValLy
              1460
AGCGGGATGTCGATTATCAAAAAAACCAAAGTATCTGCGGTCAACTACAATTYrLysGlySerPhePr
sAlaAspValAspTyrGlnLysThrLysValSerAlaValAsnTyrLysGlySerPhePr
        1510                                      1560
GATAGAGGATTCTTCCACCTTGACACGTAACTACAATCAAAAGGACTTGGATGAAATCTA
oIleGluAspSerThrLeuThrArgAsnTyrAsnGlnLysAspLeuAspGluIleTy
CAACCCGCAGTATGGATACCCCGCTTCAAACGCATTACCCTGCCGTTTGGACAGCCATCCGTT
rAsnProGlnTyrGlyTyrProAlaSerAsnArgIleThrLeuArgLeuAspSerHisProLe
                                1660
GCAACTCGGGGGGGGGCGACACCCGACGATTATTACTTCAGCGGCCGTGTTGTTCGAACCAGCAG
uGlnLeuGlyGlyGlyArgHisArgLeuSerPheLysThrPheAlaSerArgArgAspPh
                    1710
TGAAAACCTAAACCGCGACGATTATTACTTCAGCGGCCGTGTTGTTCGAACCACCAGCAG
eGluAsnLeuAsnArgAspAspTyrTyrPheSerGlyArgValValArgThrThrSerSe
```

FIG. 2E

```
                                                                                                    1760
TATCCAGCATCCGGTGAAAACCACCAACTACGGTTTCTCACTGTCTGACCAAATTCAATG
rIleGlnHisProValLysThrThrAsnTyrGlyPheSerLeuSerAspGlnIleGlnTr
       1810                                                                    1860

GAACGACGTGTTCAGTAGCCGCGCAGGTATCCGTTACGATCATACCAAAATGACGCCTCA
pAsnAspValPheSerSerArgAlaGlyIleArgTyrAspHisThrLysMETThrProGl
                                              1910

GGAATTGAATGCCGAGTGTCATGCTTGTGACAAAACACCGCCTGCAGCCAACACTTATAA
nGluLeuAsnAlaGluCysHisAlaCysAspLysThrProProAlaAlaAsnThrTyrLy
                                    1960

AGGCTGGAGCGGTTTTGTCGGCTTGGCGGCAACTGAATCAGGCTTGGCGTGTCGGTTA
sGlyTrpSerGlyPheValGlyLeuAlaGluLeuAsnGlnAlaTrpArgValGlyTyrTy
                         2010

CGACATTACTTCCGGCTACCGTGTCCCCAATGGCGTCCGAAGTGTATTTCACTTACAACCA
rAspIleThrSerGlyTyrArgValProAsnAlaSerGluValTyrPheThrTyrAsnHi
                  2060

CGGTTCGGGTAATTGGCCTGCCCAATCCCAACCTGAAAGCCGAGCGCACGACCACCACAC
sGlySerGlyAsnTrpLeuProAsnProAsnLeuLysAlaGluArgThrThrThrHisTh
       2110                                                                                       2160

CCTCTCTCTGCAAGGCCGCAGCCGGAAAAAGGTACTTTGGATGCCAACCTGTATCAAAGCAA
rLeuSerLeuGlnGlyArgSerGluLysGlyThrLeuAspAlaAsnLeuTyrGlnSerAs
```

FIG. 2F

```
TTACCGCAATTTCCTGTCTGAAGAGCAGAAGCTGACCACCAGCGGCGATGTCAGCTGTAC
 nTyrArgAsnPheLeuSerGluGluGlnLysLeuThrThrSerGlyAspValSerCysTh
                              2210
                                                        2260

TCAGATGAATTACTACTACGGTATGTGTAGCAATCCTTATTCCGAAAAACTGGAATGGCA
 rGlnMetAsnTyrTyrTyrGlyMetCysSerAsnProTyrSerGluLysLeuGluTrpGl
                              2310
                                                        2360

GATGCAAAATATCGACAAGGCCAGAATCCGCGGTATCGAGCTGACGGGCCGTCTGAATGT
 nMetGlnAsnIleAspLysAlaArgIleArgGlyIleGluLeuThrGlyArgLeuAsnVa
                              2410

GGACAAAGTAGCGTCTTTTGTTCCTGAGGGCTGGAAACTGTTCGGCTCGCTGGGTTATGC
 lAspLysValAlaSerPheValProGluGlyTrpLysLeuPheGlySerLeuGlyTyrAl
                              2460
                                                        2510

GAAAGCAAACTGTCGGGCGACAACAGCCTGCTGTCCAGCCCGTTGAAAGTGATTGCGATT
 aLysSerLysLeuSerGlyAspAsnSerLeuLeuSerThrGlnProLeuLysValIleAl
                              2510

CGGTATCGACTATGAAAGTCCGAGCGAAAAATGGGGCGTGTTCTCCCGCCTGACCTATCT
 aGlyIleAspTyrGluSerProSerGluLysTrpGlyValPheSerArgLeuThrTyrLe
                              2560

GGGCGCGAAAAAGGTCAAAGACGCGCAATACACCGTTTATGAAAACAAGGGCTGGGGTAC
 uGlyAlaLysLysValLysAspAlaGlnTyrThrValTyrGluAsnLysGlyTrpGlyTh
```

FIG. 2G

```
                          2610
GCCTTTGCAGAAAAAGGTAAAAGATTACCCGTGGCTGAACAAGTCGGCTTATGTGTTCGA
rProLeuGlnLysLysValLysAspTyrProTrpLeuAsnLysSerAlaTyrValPheAs
                              2660

TATGTACGGCTTCTACAAACCGGTGAAAAACCTGACTTTGCGTGCAGGCGTATATAATGT
pMetTyrGlyPheTyrLysProValLysAsnLeuThrLeuArgAlaGlyValTyrAsnVa
    2710                                                2760

GTTCAACCGCAAATACACCACCACTTGGGATTCCCTGCGCGGCCTGTATAGCTACAGCCAC
lPheAsnArgLysTyrThrThrThrTrpAspSerLeuArgGlyLeuTyrSerTyrSerTh
                                            2810

CAACTCGGTCGACCGCGATGGCAAAGGCTTAGACCGCTACCGCGCCCCAAGCCCGTAATTA
rAsnSerValAspArgAspGlyLysGlyLeuAspArgTyrArgAlaProSerAlaAsnTy
                    2860

CGCCGTATCGCTGGAATGGAAGTTTTAATCTGGTATTATTGAATTAATCGCCCTTGTTGAA
rAlaValSerLeuGluTrpLysPheSTOP
                    2910

AATTAAAGCCGTCCGAATTGTGTTCAAGAACTCATTCGGACGGTTTTACCGAATCTGTG

TGTGGGTTTATAGTGGATTAACAAAAATCAGGACAAGGCGACGAAGCCGCAGACAGTACA
```

FIG. 2H

```
     3010
GATAGTACGGAACCGATTCACTTGGTGAGACCTTTGCAAAATTCCTTTCCCTCCCGACAG
                              ------> IS1106                 3060
                                           3110
CCGAAACCCAAACACAGGTTTTCGGCTGTGTTTTCGCCCCAAATACCTCCTAATTCTACCCA
                                 3160
AATACCCCCCTTAATCCCTCCCCGATAACCCGATAATCAGGCATCCGGGCGCCTTTAGGCGGCA
                3210
GCGGGGCGCACTTAACCCTGTTGGCGGCTTTCAAAAGGTTCAAACACATCGCCTTCAGGTGC
                    3260
CTTTGCGCACTCACTTTAATCAGTCCGAAATAGGCCCGCGCATAGCAGAACTTACGG
       3310
TGCAGCGTACCGAAGCTT
           HindIII
```

FIG. 4A

```
TBP1M  MQQQHLFRLNILCLSLMTALPVYA---ENVQAEQAQEKQLDTIQVKAKKQ                    47
LBPA   MNKKHGFQLTLTALAVAAAFPSYAANPETAAPDAAQTQSLKEVTVRAAKV                    50
HMBR   MKPLQMLPIAALVGSIFGN-PVFAADEAATETTPVKAE-----VKAVR                      43
             *    *              *                           *  *

TBP1M  KTRRDNEVTGLGKLVKSSDTLSKEQVLNIRDLTRYDPGIAVVEQGRGASS                    97
LBPA   -GRRSKEATGLGKIAKTSETLNKEQVLGIRDLTRYDPGVAVVEQGNGASG                    99
HMBR   KGQRNA-PAAVERV--NLNRIKQEMIRDNKDLVRYSTDVGLSDSGRHQK-                    89
         *    *           *           ***

TBP1M  GYSIRGMDKNRVSLTVDGVSQIQSYTAQAALGGTRTAGSSGAINEIEYEN                   147
LBPA   GYSIRGVDKNRVAVSVDGVAQIQAFTVQGSLSGYGGRGGSGAINEIEYEN                   149
HMBR   GFAVRGVEGNRVGVSIDGVNLPDS--EENSLYARYGNFNSSRLS-IDPEL                   136
        *  ** * ***  *  **                 *           *

TBP1M  VKAVEISKGSNSSEYGNGALAGSVAFQTKTAADIIGEGKQWGIQSKTAYS                   197
LBPA   ISTVEIDKGAGSSDHGSGALGGAVAFRTKEAADLISDGKSWGIQAKTAYG                   199
HMBR   VRNIDIVKGADSFNTGSGALGGGVYNQTLQGRDLLLPERQFGVMMKNGYS                   186
            *  **    *  *** *  *    *   **          *   *

TBP1M  GKDHALTQSLALAGRSGGAEALLIYTKRRGREIHAHKDAGKGVQ-SFNRL                   246
LBPA   SKNRQFMKSLGAGFSKDGWEGLLIRTERQGRETHPHGDIADGVAYGINRL                   249
HMBR   TRNREWTNTLGFGVSNDRVDAALLYSQRRGHETESAG------------                    223
                          **                   *
```

FIG. 4B

```
TBP1M   PICRFGNNTYT-DCTPRNIGGNGYYAAVQDNVRLGRWADVGAGIRYDYRS       601
LBPA    SVCGYIETLRSRKCVPRKINGSNIHISLNDRFSIGKYFDFSLGGRYDRKN       635
HMBR    --------SSIQHPVKTTNYGFSLSDQIQWNDVFSSRAGIRYDHTK          460
                                              *   *  *****

TBP1M   THSED-------KSVSTGTHRNLSWNAGVVLKP--FTWMDLTYRASTGF        641
LBPA    FTTSE-------ELVRSGRYVDRSWNSGIVFKP--NRHFSLSYRASSGF        675
HMBR    MTPQELNAECHACDKTPPAANTYKGWSGFVGLAAQLNQAWRVGYDITSGY       510
                                              *        *

TBP1M   RLPSFAEMYGWRA-----GESLKTLDLKPEKSFNREAGIVFKGDFGNLEAS      687
LBPA    RTPSFQELFGIDIYHDYPKGWQRPALKSEKAANREIGLQWKGDFGFLEIS       725
HMBR    RVPNASEVY-FTYNHGSGNWLPNPNLKAERTTTHTLSLQGRSEKGTLDAN       559
         *  *                              *    *

TBP1M   YFNNAYRDLIAFGYET---RTQNGQTSASGDPGYR-------------         719
LBPA    SFRNRYTDMIAVADHKTKLPNQAGQLTEIDIRDYY-------------         760
HMBR    LYQSNYRNFLS---EEQKLTT-SGDVSCTQMNYYYGMCSNPYSEKLEWQM       605
              *

TBP1M   -NAQNARIAGINILGKIDWHGVWGGLPDG--LYSTLAYNRIKVKDADIRA       766
LBPA    -NAQNMSLQGVNILGKIDWNGVYGKLPEG--LYTTLAYNRIKPKSVSNRP       807
HMBR    QNIDKARIRGIELTGRLNVDKVASFVPEGWKLFGSLGYAKSKLSG----         650
         *                               *
```

FIG. 4C

```
TBP1M   DRTFVTSYLFDAVQPSRYVLGLGYDHPDGIWGINTMFTYSKAKSVDE---  813
LBPA    GLSL-RSYALDAVQPSRYVLGFGYDQPEGKWGANIMLTYSKGKNPDE---  853
HMBR    DNSLLST-----QPLKVIAGIDYESPSEKWGVFSRLTYLGAKKVKDAQY   694
                *     *   .       * . .       *

TBP1M   -LLGSQALLNGNANAKKAASRRTRPWYVTDVSGYYNIKKHLTLRAGVYNL   862
LBPA    -L----AYLAGDQK-RYSTKRASSSWSTADVSAYLNLKKRLTLRAAIYNI   897
HMBR    TVYENKGWGTPLQKKVKDYPWLNKSAYVFDMYGFYKPVKNLTLRAGVYNV   744
              *                 .            **  .* **  *

TBP1M   LNYRYVTWENVRQ--TAGGAVNQHKNVGVYNRYAAPGRNYTFSLEMKF    908
LBPA    GNYRYVTWESLRQ--TAESTANRHGGDSNYGRYAAPGRNFSLALEMKF    943
HMBR    FNRKYTTWDSLRGLYSYSTTNSVDRDGKGLDRYRAPSRNYAVSLEWKF    792
         *  ***  .        .          **  .*  *  * ***
```

FIG. 7A

```
ATG AAA CCA TTA CAA ATG CCC CCT ATC GCC GCG CTG CTC GGC AGT ATT      48
Met Lys Pro Leu Gln Met Pro Pro Ile Ala Ala Leu Leu Gly Ser Ile
 1               5                  10                  15

TTC GGC AAT CCG GTC TTT GCG GCA GAT GCA ACT GAA GCT GCA ACC ACA      96
Phe Gly Asn Pro Val Phe Ala Ala Asp Ala Thr Glu Ala Ala Thr Thr
            20                  25                  30

CCC GTT AAG GCA GAG GTA AAA GCA GTG CGC GTT AAA GGT CAG CGC AAT     144
Pro Val Lys Ala Glu Val Lys Ala Val Arg Val Lys Gly Gln Arg Asn
        35                  40                  45

GCG CCT GCG GCT GTG GAA CGC GTC AAC CTT AAC CGT ATC AAA CAA GAA     192
Ala Pro Ala Ala Val Glu Arg Val Asn Leu Asn Arg Ile Lys Gln Glu
    50                  55                  60

ATG ATA CGC GAC AAT AAA GAC TTG GTG CGC TAT TCC ACC GAT GTC GGC     240
Met Ile Arg Asp Asn Lys Asp Leu Val Arg Tyr Ser Thr Asp Val Gly
65                  70                  75                  80

TTG AGC GAC AGG AGC CGT CAT CAA AAA GGC TTT GCC ATT CGC GGC GTG     288
Leu Ser Asp Arg Ser Arg His Gln Lys Gly Phe Ala Ile Arg Gly Val
            85                  90                  95
```

FIG. 7B

```
GAA GGC GAC CGT GTC GGC GTT AGT ATT GAC GGC GTA AAC CTG CCT GAT
Glu Gly Asp Arg Val Gly Val Ser Ile Asp Gly Val Asn Leu Pro Asp       336
        100                     105                     110

TCC GAA GAA AAC TCG CTG TAC GCC CGT TAT GGC AAC TTC AAC AGC TCG
Ser Glu Glu Asn Ser Leu Tyr Ala Arg Tyr Gly Asn Phe Asn Ser Ser       384
        115                     120                     125

CGT CTG TCT ATC GAC CCC GAA CTC GTG CGC AAC ATC GAC ATC GTA AAA
Arg Leu Ser Ile Asp Pro Glu Leu Val Arg Asn Ile Asp Ile Val Lys       432
    130                     135                     140

GGG GCG GAC TCT TTC AAT ACC GGC AGC GGC GCC TTG GGC GGT GTG
Gly Ala Asp Ser Phe Asn Thr Gly Ser Gly Ala Leu Gly Gly Val           480
145                     150                     155         160

AAT TAC CAA ACC CTG CAA GGA CGT GAC TTA CTG TTG CCT GAA CGG CAG
Asn Tyr Gln Thr Leu Gln Gly Arg Asp Leu Leu Leu Pro Glu Arg Gln       528
        165                     170                     175

TTC GGC GTG ATG ATG AAA AAC GGT TAC AGC ACG CGT AAC CGT GAA TGG
Phe Gly Val Met Met Lys Asn Gly Tyr Ser Thr Arg Asn Arg Glu Trp       576
        180                     185                     190
```

FIG. 7C

```
ACA AAT ACC CTC GGT TTC GGC GTG AGC AAC GAC CGC GTG GAT GCC GCT    624
Thr Asn Thr Leu Gly Phe Gly Val Ser Asn Asp Arg Val Asp Ala Ala
195                 200                 205

TTG CTG TAT TCG CAA CGG CGC CAT GAA ACT GAA AGC GCG GGC AAG        672
Leu Leu Tyr Ser Gln Arg Arg His Glu Thr Glu Ser Ala Gly Lys
210                 215                 220

CGT GGT TAT CCG GTA GAG GGT GCT GGT AGC GGA GCG AAT ATC CGT GGT    720
Arg Gly Tyr Pro Val Glu Gly Ala Gly Ser Gly Ala Asn Ile Arg Gly
225                 230                 235                 240

TCT GCG CGC GGT ATT CCT GAT CCG TCC CAA CAC AAA TAC CAC AGC TTC    768
Ser Ala Arg Gly Ile Pro Asp Pro Ser Gln His Lys Tyr His Ser Phe
            245                 250                 255

TTG GGT AAG ATT GCT TAT CAA ATC AAC GAC AAC CAC CGC ATC GGC GCA    816
Leu Gly Lys Ile Ala Tyr Gln Ile Asn Asp Asn His Arg Ile Gly Ala
        260                 265                 270

TCG CTC AAC GGT CAG CAG GGG CAT AAT TAC ACG GTT GAA GAG TCT TAC    864
Ser Leu Asn Gly Gln Gln Gly His Asn Tyr Thr Val Glu Glu Ser Tyr
275                 280                 285
```

FIG. 7D

```
AAC CTG CTT GCT TCT TAT TGG CGT GAA GCT GAC GAT GTC AAC AGA CGG    912
Asn Leu Leu Ala Ser Tyr Trp Arg Glu Ala Asp Asp Val Asn Arg Arg
        290             295             300

CGT AAC ACC AAC CTC TTT TAC GAA TGG ACG CCG GAA TCC GAC CGG TTG    960
Arg Asn Thr Asn Leu Phe Tyr Glu Trp Thr Pro Glu Ser Asp Arg Leu
305             310             315             320

TCT ATG GTA AAA GCG GAT GTC GAT TAT CAA AAA ACC AAA GTA TCT GCG   1008
Ser Met Val Lys Ala Asp Val Asp Tyr Gln Lys Thr Lys Val Ser Ala
        325             330             335

GTC AAC TAC AAA GGT TCG TTC CCG ACG AAT TAC ACC ACA TGG GAA ACC   1056
Val Asn Tyr Lys Gly Ser Phe Pro Thr Asn Tyr Thr Thr Trp Glu Thr
340             345             350

GAG TAC CAT AAA GAA GTT GGC GAA ATC TAT AAC CGC AGC ATG GAT       1104
Glu Tyr His Lys Glu Val Gly Glu Ile Tyr Asn Arg Ser Met Asp
        355             360             365

ACA ACC TTC AAA CGT ATT ACG CTG CGT ATG GAC AGC CAT CCG TTG CAA   1152
Thr Thr Phe Lys Arg Ile Thr Leu Arg Met Asp Ser His Pro Leu Gln
370             375             380
```

FIG. 7E

| | | | | | | | | | | | | | | | | |
|---|---|---|---|---|---|---|---|---|---|---|---|---|---|---|---|---|
CTC | GGG | GGG | CGA | CAC | CGC | CTG | TCG | TTC | AAA | ACC | TTT | GCC | GGG | CAG | | | 1200
Leu | Gly | Gly | Arg | His | Arg | Leu | Ser | Phe | Lys | Thr | Phe | Ala | Gly | Gln
385 | | | | | 390 | | | | 395 | | | | | 400

CGT | GAT | TTT | GAA | AAC | TTA | AAC | CGC | GAC | GAT | TAC | TAC | TTC | AGC | GGC | CGT | 1248
Arg | Asp | Phe | Glu | Asn | Leu | Asn | Arg | Asp | Asp | Tyr | Tyr | Phe | Ser | Gly | Arg
| | | | 405 | | | | | 410 | | | | | 415

GTT | GTT | CGA | ACC | ACC | AAC | AGT | ATC | CAG | CAT | CCG | GTG | AAA | ACC | ACC | AAC | 1296
Val | Val | Arg | Thr | Thr | Asn | Ser | Ile | Gln | His | Pro | Val | Lys | Thr | Thr | Asn
| | 420 | | | | | 425 | | | | | 430

TAC | GGT | TTC | TCG | CTG | TCC | GAC | CAA | ATC | CAA | TGG | AAC | GAC | GTG | TTC | AGT | 1344
Tyr | Gly | Phe | Ser | Leu | Ser | Asp | Gln | Ile | Gln | Trp | Asn | Asp | Val | Phe | Ser
| | 435 | | | | | 440 | | | | | 445

AGC | CGC | GCA | GGT | ATC | CGT | TAC | GAC | CAC | ACC | AAA | ATG | ACG | CCT | CAG | GAA | 1392
Ser | Arg | Ala | Gly | Ile | Arg | Tyr | Asp | His | Thr | Lys | Met | Thr | Pro | Gln | Glu
450 | | | | | 455 | | | | | 460

TTG | AAT | GCC | GAC | TGT | CAT | GCT | TGT | GAC | AAA | ACA | CCG | CCT | GCA | GCC | AAC | 1440
Leu | Asn | Ala | Asp | Cys | His | Ala | Cys | Asp | Lys | Thr | Pro | Pro | Ala | Ala | Asn
465 | | | | 470 | | | | | 475 | | | | | 480

FIG. 7F

```
ACT TAT AAA GGC TGG AGC GGA TTT GTC GGC TTG GCG CAG CTG AGC     1488
Thr Tyr Lys Gly Trp Ser Gly Phe Val Gly Leu Ala Gln Leu Ser
        485                 490                 495

CAA ACA TGG CGT TTG GGT TAC GAT GTG ACC TCA GGT TTC CGC GTG CCG     1536
Gln Thr Trp Arg Leu Gly Tyr Asp Val Thr Ser Gly Phe Arg Val Pro
            500                 505                 510

AAT GCG TCT GAA GTG TAT TTC ACT TAC AAC CAC GGT TCG GGC ACT TGG     1584
Asn Ala Ser Glu Val Tyr Phe Thr Tyr Asn His Gly Ser Gly Thr Trp
        515                 520                 525

AAG CCT AAT CCT AAT TTG AAG GCA GAA CGC AGC ACC ACC CAC ACC CTG     1632
Lys Pro Asn Pro Asn Leu Lys Ala Glu Arg Ser Thr Thr His Thr Leu
    530                 535                 540

TCC TTG CAG GGG CGC GGC GAC AAA GGG ACA CTG GAT GCC AAC CTG TAT     1680
Ser Leu Gln Gly Arg Gly Asp Lys Gly Thr Leu Asp Ala Asn Leu Tyr
545                 550                 555                 560

CAA AGC AAT TAC CGA AAC TTC CTG TCG GAA GAG CAG AAT CTG ACT GTC     1728
Gln Ser Asn Tyr Arg Asn Phe Leu Ser Glu Glu Gln Asn Leu Thr Val
            565                 570                 575
```

FIG. 7G

```
AGC GGC ACA CCC GGC TGT ACT GAG GAT GCT TAC TAC TAT AGA TGC
Ser Gly Thr Pro Gly Cys Thr Glu Asp Ala Tyr Tyr Tyr Arg Cys    1776
            580                 585                 590

AGC GAC CCC TAC AAA GAA AAA CTG GAT TGG CAG ATG AAA AAT ATC GAC
Ser Asp Pro Tyr Lys Glu Lys Leu Asp Trp Gln Met Lys Asn Ile Asp    1824
            595                 600                 605

AAG GCC AGA ATC CGC GGT ATC GAG TTG ACA GGC CGT AAT GTG GAC
Lys Ala Arg Ile Arg Gly Ile Glu Leu Thr Gly Arg Asn Val Asp    1872
            610                 615                 620

AAA GTA GCG TCT TTT GTT CCT GAG GGT TGG AAA CTG TTC GGC TCG CTG
Lys Val Ala Ser Phe Val Pro Glu Gly Trp Lys Leu Phe Gly Ser Leu    1920
            625                 630                 635                 640

AAA AGC CTG AAA AGC GGC GAC AAC AGC CTG CTG TCC ACA
Lys Ser Leu Lys Ser Gly Asp Asn Ser Leu Leu Ser Thr    1968
            645                 650                 655

GGT TAT GCG CCG CTG AAA GTG ATT GCC GGT ATC GAC TAT GAA AGT CCG AGC GAA
Gly Tyr Ala Pro Leu Lys Val Ile Ala Gly Ile Asp Tyr Glu Ser Pro Ser Glu    2016
            660                 665                 670
```

FIG. 7H

```
AAA TGG GGC GTA TTC TCC CGC CTG ACC TAT CTA GGC GCG AAA AAG GTC    2064
Lys Trp Gly Val Phe Ser Arg Leu Thr Tyr Leu Gly Ala Lys Lys Val
            675                 680                 685

AAA GAC GCG CAA TAC ACC GTT TAT GAA AAC AAG GGC TGG GGT ACG CCT    2112
Lys Asp Ala Gln Tyr Thr Val Tyr Glu Asn Lys Gly Trp Gly Thr Pro
            690                 695                 700

TTG CAG AAA AAG GTA AAA GAT TAC CCG TGG CTG AAC AAG TCG GCT TAT    2160
Leu Gln Lys Lys Val Lys Asp Tyr Pro Trp Leu Asn Lys Ser Ala Tyr
            705                 710                 715                 720

GTG TTT GAT ATG TAC GGC TTC TAC AAA CCG GCT AAA AAC CTG ACT TTG    2208
Val Phe Asp Met Tyr Gly Phe Tyr Lys Pro Ala Lys Asn Leu Thr Leu
            725                 730                 735

CGT GCA GGC GTG TAC AAC CTG TTC AAC CGC AAA TAC ACC ACT TGG GAT    2256
Arg Ala Gly Val Tyr Asn Leu Phe Asn Arg Lys Tyr Thr Thr Trp Asp
            740                 745                 750

TCC CTG CGC GGT TTA TAT AGC TAC AGC ACC AAT GCG GTC GAC CGC        2304
Ser Leu Arg Gly Leu Tyr Ser Tyr Ser Thr Asn Ala Val Asp Arg
            755                 760                 765
```

FIG. 7I

```
                                                                              2352
GAT GGC AAA GGC TTA GAC CGC TAC CGC GCC CCA GGC CGC AAT TAC GCC
Asp Gly Lys Gly Leu Asp Arg Tyr Arg Ala Pro Gly Arg Asn Tyr Ala
770                     775                 780

2375
GTA TCG CTG GAA TGG AAG TTT TAA
Val Ser Leu Glu Trp Lys Phe *
785                 790
```

FIG. 8A

```
ATG AAA CCA TTA CAA ATG CTC CCT ATC GCC GCG CTG GTC GGC AGT ATT    48
Met Lys Pro Leu Gln Met Leu Pro Ile Ala Ala Leu Val Gly Ser Ile
 1               5                  10                  15

TTC GGC AAT CCG GTC TTT GCG GCA GAT GAA GCT GCA ACT GAA ACC ACA    96
Phe Gly Asn Pro Val Phe Ala Ala Asp Glu Ala Ala Thr Glu Thr Thr
            20                  25                  30

CCC GTT AAG GCA GAG GTA AAA GCA GTG CGC GTT AAA GGC CAG CGC AAT   144
Pro Val Lys Ala Glu Val Lys Ala Val Arg Val Lys Gly Gln Arg Asn
        35                  40                  45

GCG CCT GCG GCT GTG GAA CGC GTC AAC CTT AAC CGT ATC AAA CAA GAA   192
Ala Pro Ala Ala Val Glu Arg Val Asn Leu Asn Arg Ile Lys Gln Glu
    50                  55                  60

ATG ATA CGC GAC AAC AAA GAC TTG GTG CGC TAT TCC ACC GAT GTC GGC   240
Met Ile Arg Asp Asn Lys Asp Leu Val Arg Tyr Ser Thr Asp Val Gly
65                  70                  75                  80

TTG AGC GAC AGC GGC CGC CAT CAA AAA GGC TTT GCT GTT CGC GGC GTG   288
Leu Ser Asp Ser Gly Arg His Gln Lys Gly Phe Ala Val Arg Gly Val
            85                  90                  95
```

FIG. 8B

```
GAA GGC AAC CGT GTC GGC GTG AGC ATA GAC GGC GTA AAC CTG CCT GAT    336
Glu Gly Asn Arg Val Gly Val Ser Ile Asp Gly Val Asn Leu Pro Asp
                100                 105                 110

TCC GAA GAA AAC TCG CTG TAC GCC CGT TAT GGC AAC TTC AAC AGC TCG    384
Ser Glu Glu Asn Ser Leu Tyr Ala Arg Tyr Gly Asn Phe Asn Ser Ser
            115                 120                 125

CGT CTG TCT ATC GAC CCC GAA CTC GTG CGC AAC ATC GAC ATC GTA AAA    432
Arg Leu Ser Ile Asp Pro Glu Leu Val Arg Asn Ile Asp Ile Val Lys
        130                 135                 140

GGG GCG GAC TCT TTC AAT ACC GGC AGC GGC GCC TTG GGC GGT GTG        480
Gly Ala Asp Ser Phe Asn Thr Gly Ser Gly Ala Leu Gly Gly Val
    145                 150                 155             160

AAT TAC CAA ACC CTG CAA GGA CGT GAC TTA CTG CCT GAA CGG CAG        528
Asn Tyr Gln Thr Leu Gln Gly Arg Asp Leu Leu Pro Glu Arg Gln
                165                 170                 175

TTC GGC GTG ATG ATG AAA AAC GGT TAC AGC ACG CGT AAC CGT GAA TGG    576
Phe Gly Val Met Met Lys Asn Gly Tyr Ser Thr Arg Asn Arg Glu Trp
            180                 185                 190
```

FIG. 8C

```
ACA AAT ACC CTC GGT TTC GGC GTG AGC AAC GAC CGC GTG GAT GCC GCT    624
Thr Asn Thr Leu Gly Phe Gly Val Ser Asn Asp Arg Val Asp Ala Ala
            195                 200                 205

TTG CTG TAT TCG CAA CGG CGC CAT GAA ACT GAA AGC GCG GGC AAG        672
Leu Leu Tyr Ser Gln Arg Arg His Glu Thr Glu Ser Ala Gly Lys
    210                 215                 220

CGT GGT TAT CCG GTA GAG GTT GCT GGT AGC GGA GCG AAT ATC CGT GGT    720
Arg Gly Tyr Pro Val Glu Val Ala Gly Ser Gly Ala Asn Ile Arg Gly
225                 230                 235                 240

TCT GCG CGC GGT ATT CCT GAT CCG TCC CAA CAC CAC AAA TAC CAC AGC TTC 768
Ser Ala Arg Gly Ile Pro Asp Pro Ser Gln His His Lys Tyr His Ser Phe
            245                 250                 255

TTG GGT AAG ATT GCT TAT CAA ATC AAC GAC AAC CAC CGC ATC GGC GCA    816
Leu Gly Lys Ile Ala Tyr Gln Ile Asn Asp Asn His Arg Ile Gly Ala
    260                 265                 270

TCG CTC AAC GGT CAG CAG GGG CAT AAT TAC ACG GTT GAA GAG TCT TAC    864
Ser Leu Asn Gly Gln Gln Gly His Asn Tyr Thr Val Glu Glu Ser Tyr
275                 280                 285
```

FIG. 8D

```
AAC CTG CTT GCT TCT TAT TGG CGT GAA GCT GAC GAT GTC AAC AGA CGG       911
Asn Leu Leu Ala Ser Tyr Trp Arg Glu Ala Asp Asp Val Asn Arg Arg
    290                 295                 300

CGT AAC ACC AAC CTC TTT TAC GAA TGG ACG CCG GAA TCC GAC CGG TTG       960
Arg Asn Thr Asn Leu Phe Tyr Glu Trp Thr Pro Glu Ser Asp Arg Leu
305                 310                 315                 320

TCT ATG GTA AAA GCG GAT GTC GAT TAT CAA AAA ACC AAA GTA TCT GCG      1008
Ser Met Val Lys Ala Asp Val Asp Tyr Gln Lys Thr Lys Val Ser Ala
                325                 330                 335

GTC AAC TAC AAA GGT TCG TTC CCG ATA GAG GAT TCT TCC ACC TTG ACA      1056
Val Asn Tyr Lys Gly Ser Phe Pro Ile Glu Asp Ser Ser Thr Leu Thr
340                 345                 350

CGT AAC TAC AAT CAA AAG GAC TTG GAT GAA ATC TAC AAC CGC AGT ATG      1104
Arg Asn Tyr Asn Gln Lys Asp Leu Asp Glu Ile Tyr Asn Arg Ser Met
            355                 360                 365

GAT ACC CGC TTC AAA CGC ATT ACC CTG CGT TTG GAC AGC CAT CCG TTG      1152
Asp Thr Arg Phe Lys Arg Ile Thr Leu Arg Leu Asp Ser His Pro Leu
370                 375                 380
```

FIG. 8E

```
CAA CTC GGG GGG CGA CAC CGC CTG TCG TTT AAA ACT TTC GCC AGC      1200
Gln Leu Gly Gly Arg His Arg Leu Ser Phe Lys Thr Phe Ala Ser
385                 390                 395                 400

CGC CGT GAT TTT GAA CTA AAC CGC GAC TAT TAC TTC AGC GGC          1248
Arg Arg Asp Phe Glu Leu Asn Arg Asp Tyr Tyr Phe Ser Gly
            405                 410                 415

CGT GTT CGA ACC ACC AGC AGT ATC CAG CAT CCG GTG AAA ACC ACC      1296
Arg Val Val Arg Thr Thr Ser Ser Ile Gln His Pro Val Lys Thr Thr
    420                 425                 430

AAC TAC GGT TTC TCA CTG TCT GAC CAA ATT CAA TGG AAC GAC GTG TTC  1344
Asn Tyr Gly Phe Ser Leu Ser Asp Gln Ile Gln Trp Asn Asp Val Phe
        435                 440                 445

AGT AGC CGC GCA GGT ATC CGT TAC GAT CAT ACC AAA ATG ACG CCT CAG  1392
Ser Ser Arg Ala Gly Ile Arg Tyr Asp His Thr Lys Met Thr Pro Gln
450                 455                 460

GAA TTG AAT GCC GAG TGT CAT GCT TGT GAC AAA ACA CCG CCT GCA GCC  1440
Glu Leu Asn Ala Glu Cys His Ala Cys Asp Lys Thr Pro Pro Ala Ala
465                 470                 475                 480
```

FIG. 8F

```
AAC ACT TAT AAA GGC TGG AGC GGT TTT GTC GGC TTG GCG GCG CAA CTG    1488
Asn Thr Tyr Lys Gly Trp Ser Gly Phe Val Gly Leu Ala Ala Gln Leu
        485             490             495

AAT CAG GCT TGG CGT GTC GGT TAC GAC ATT ACT TCC GGC TAC CGT GTC    1536
Asn Gln Ala Trp Arg Val Gly Tyr Asp Ile Thr Ser Gly Tyr Arg Val
        500             505             510

CCC AAT GCG TCC GAA GTG TAT TTC TAC AAC CAC GGT TCG GGT AAT         1584
Pro Asn Ala Ser Glu Val Tyr Phe Tyr Asn His Gly Ser Gly Asn
        515             520             525

TGG CTG CCC AAT CCC AAC CTG AAA GCC GAG CGC ACG ACC ACC CAC ACC    1632
Trp Leu Pro Asn Pro Asn Leu Lys Ala Glu Arg Thr Thr Thr His Thr
        530             535             540

CTC TCT CTG CAA GGC CGC AGC GAA AAA GGT ACT TTG GAT GCC AAC CTG    1680
Leu Ser Leu Gln Gly Arg Ser Glu Lys Gly Thr Leu Asp Ala Asn Leu
        545             550             555             560

TAT CAA AGC AAT TAC CGC AAT TTC CTG TCT GAA GAG CAG AAG CTG ACC    1728
Tyr Gln Ser Asn Tyr Arg Asn Phe Leu Ser Glu Glu Gln Lys Leu Thr
        565             570             575
```

FIG. 8G

```
ACC AGC GGC GAT GTC AGC TGT ACT CAG ATG AAT TAC TAC TAC GGT ATG    1776
Thr Ser Gly Asp Val Ser Cys Thr Gln Met Asn Tyr Tyr Tyr Gly Met
            580                 585                 590

TGT AGC AAT CCT TAT TCC GAA AAA CTG GAA TGG CAG ATG CAA AAT ATC    1824
Cys Ser Asn Pro Tyr Ser Glu Lys Leu Glu Trp Gln Met Gln Asn Ile
            595                 600                 605

GAC AAG GCC AGA ATC CGC GGT ATC GAG CTG ACG GGC CGT CTG AAT GTG    1872
Asp Lys Ala Arg Ile Arg Gly Ile Glu Leu Thr Gly Arg Leu Asn Val
            610                 615                 620

GAC AAA GTA GCG TCT TTT GTT CCT GAG GGC TGG AAA CTG TTC GGC TCG    1920
Asp Lys Val Ala Ser Phe Val Pro Glu Gly Trp Lys Leu Phe Gly Ser
    625                 630                 635                 640

CTG GGT TAT GCG AAA AGC AAA CTG TCG GAC AAC AGC CTG CTG TCC        1968
Leu Gly Tyr Ala Lys Ser Lys Leu Ser Asp Asn Ser Leu Leu Ser
            645                 650                 655

ACC CAG CCG TTG AAA GTG ATT GCC GGT ATC GAC TAT GAA AGT CCG AGC    2016
Thr Gln Pro Leu Lys Val Ile Ala Gly Ile Asp Tyr Glu Ser Pro Ser
            660                 665                 670
```

FIG. 8H

| | | | | | | | | | | | | | | | |
|---|---|---|---|---|---|---|---|---|---|---|---|---|---|---|---|
| GAA | AAA | TGG | GGC | GTG | TTC | TCC | CGC | CTG | ACC | TAT | CTG | GGC | GCG | AAA | AAG |
| Glu | Lys | Trp | Gly | Val | Phe | Ser | Arg | Leu | Thr | Tyr | Leu | Gly | Ala | Lys | Lys |
| | 675 | | | | | 680 | | | | 685 | | | | | |

2064

| | | | | | | | | | | | | | | | |
|---|---|---|---|---|---|---|---|---|---|---|---|---|---|---|---|
| GTC | AAA | GAC | GCG | CAA | TAC | ACC | GTT | TAT | GAA | AAC | AAG | GGC | TGG | GGT | ACG |
| Val | Lys | Asp | Ala | Gln | Tyr | Thr | Val | Tyr | Glu | Asn | Lys | Gly | Trp | Gly | Thr |
| | 690 | | | | 695 | | | | | 700 | | | | | |

2112

| | | | | | | | | | | | | | | | |
|---|---|---|---|---|---|---|---|---|---|---|---|---|---|---|---|
| CCT | TTG | CAG | AAA | AAG | GTA | GTG | AAA | GAT | TAC | CCG | TGG | CTG | AAC | AAG | TCG | GCT |
| Pro | Leu | Gln | Lys | Lys | Val | Val | Lys | Asp | Tyr | Pro | Trp | Leu | Asn | Lys | Ser | Ala |
| 705 | | | | | 710 | | | | | 715 | | | | | | 720 |

2160

| | | | | | | | | | | | | | | | |
|---|---|---|---|---|---|---|---|---|---|---|---|---|---|---|---|
| TAT | GTG | TTC | GAT | ATG | TAC | ATG | TAC | GGC | TTC | TAC | AAA | CCG | GTG | AAA | AAC | CTG | ACT |
| Tyr | Val | Phe | Asp | Met | Tyr | Met | Tyr | Gly | Phe | Tyr | Lys | Pro | Val | Lys | Asn | Leu | Thr |
| | | | | 725 | | | | | | 730 | | | | | | | 735 |

2208

| | | | | | | | | | | | | | | | |
|---|---|---|---|---|---|---|---|---|---|---|---|---|---|---|---|
| TTG | CGT | GCA | GGC | GTA | TAT | AAT | GTG | TTC | AAC | CGC | AAA | TAC | ACC | ACT | TGG |
| Leu | Arg | Ala | Gly | Val | Tyr | Asn | Val | Phe | Asn | Arg | Lys | Tyr | Thr | Thr | Trp |
| | | 740 | | | | | 745 | | | | | 750 | | | |

2256

| | | | | | | | | | | | | | | | |
|---|---|---|---|---|---|---|---|---|---|---|---|---|---|---|---|
| GAT | TCC | CTG | CGC | GGC | CTG | TAT | AGC | TAC | AGC | ACC | AAC | TCG | GTC | GAC |
| Asp | Ser | Leu | Arg | Gly | Leu | Tyr | Ser | Tyr | Ser | Thr | Asn | Ser | Val | Asp |
| 755 | | | | | | 760 | | | | | 765 | | | | |

2304

FIG. 8I

```
                                                                              2352
CGC GAT GGC AAA GGC TTA GAC CGC TAC CGC GCC CCA AGC CGT AAT TAC
Arg Asp Gly Lys Gly Leu Asp Arg Tyr Arg Ala Pro Ser Arg Asn Tyr
    770                 775                 780

2379
GCC GTA TCG CTG GAA TGG AAG TTT TAA
Ala Val Ser Leu Glu Trp Lys Phe  *
785                 790
```

FIG. 9A

```
ATG AAA CCA TTA CAC ATG CTT CCT ATT GCC GCG CTG GTC GGC AGT ATT      48
Met Lys Pro Leu His Met Leu Pro Ile Ala Ala Leu Val Gly Ser Ile
1                 5                  10                  15

TTC GGC AAT CCG GTC TTG GCA GCG GAT GAA GCT GCA ACC GAA ACC ACA      96
Phe Gly Asn Pro Val Leu Ala Ala Asp Glu Ala Ala Thr Glu Thr Thr
         20                  25                  30

CCC GTT AAA GCA GAG ATA AAA GAA GTT AAA GAC CAG CTT AAT             144
Pro Val Lys Ala Glu Ile Lys Glu Val Lys Asp Gln Leu Asn
     35                  40                  45

GCG CCT GCA ACC GTG GAA CGT GTC AAC CTC GGC CGC ATT CAA CAG GAA     192
Ala Pro Ala Thr Val Glu Arg Val Asn Leu Gly Arg Ile Gln Gln Glu
50                  55                  60

ATG ATA CGC GAC AAC AAA GAC TTG GTG CGT TAC TCC ACC GAC GTC GGC     240
Met Ile Arg Asp Asn Lys Asp Leu Val Arg Tyr Ser Thr Asp Val Gly
65                  70                  75                  80

TTG AGC GAT AGC GGC CGC CAT CAA AAA GGC TTT GCT GTG CGC GGC GTG     288
Leu Ser Asp Ser Gly Arg His Gln Lys Gly Phe Ala Val Arg Gly Val
         85                  90                  95
```

FIG. 9B

```
GAA GGC AAC CGT GTC GGT GTC AGC ATT GAC GGC GTG AGC CTG CCT GAT      336
Glu Gly Asn Arg Val Gly Val Ser Ile Asp Gly Val Ser Leu Pro Asp
            100                 105                 110

TCG GAA GAA AAC TCA CTG TAT GCA CGT TAT GGC AAC TTC AAC AGC TCG      384
Ser Glu Glu Asn Ser Leu Tyr Ala Arg Tyr Gly Asn Phe Asn Ser Ser
        115                 120                 125

CGC CTG TCT ATC GkC CCC GAA CTC GTG CGC AAC ATC GAA ATC GCG AAG      432
Arg Leu Ser Ile Asp Pro Glu Leu Val Arg Asn Ile Glu Ile Ala Lys
    130                 135                 140

GGC GCT GAC TCT TTC AAT ACC GGT AGC GGT GCA TTG GGT GGC GGC GTG      480
Gly Ala Asp Ser Phe Asn Thr Gly Ser Gly Ala Leu Gly Gly Gly Val
145                 150                 155                 160

AAT TAC CAA ACC CTG CAA GGA CAT GAT TTG GAC TTG GAC GAC AGG CAA      528
Asn Tyr Gln Thr Leu Gln Gly His Asp Leu Leu Leu Asp Asp Arg Gln
        165                 170                 175

TTC GGC GTG ATG ATG AAA AAC GGT TAC AGC CGC AAC AGC CGC AAC CGC AAC CGC TGG      576
Phe Gly Val Met Met Lys Asn Gly Tyr Ser Ser Arg Asn Arg Glu Trp
    180                 185                 190
```

FIG. 9C

```
ACA AAT ACA CTC GGT TTC GGT GTG AGC AAC GAC CGC GTG GAT GCC GCT    624
Thr Asn Thr Leu Gly Phe Gly Val Ser Asn Asp Arg Val Asp Ala Ala
        195                 200                 205

TTG CTG TAT TCG CAA CGT CGC GGT CAT GAG ACC GAA AGC GCG GGC GAG    672
Leu Leu Tyr Ser Gln Arg Arg Gly His Glu Thr Glu Ser Ala Gly Glu
210                 215                 220

CGT GGC TAT CCG GTA GAG GGT GCT GGC AGC GGA GCA ATT ATC CGT GGT    720
Arg Gly Tyr Pro Val Glu Gly Ala Gly Ser Gly Ala Ile Ile Arg Gly
225                 230                 235                 240

TCG TCA CGC GGT ATC CCT GAT CCG TCC AAA CAC AAA TAC CAC AAC TTC    768
Ser Ser Arg Gly Ile Pro Asp Pro Ser Lys His Lys Tyr His Asn Phe
        245                 250                 255

TTG GGT AAG ATT GCT TAT CAA ATC AAC GAC AAG CAC CGC ATC GGC CCA    816
Leu Gly Lys Ile Ala Tyr Gln Ile Asn Asp Lys His Arg Ile Gly Pro
260                 265                 270

TCG TTT AAC GGC CAG CAG GGG CAT AAT TAC ACG ATT GAA GAG TCT TAT    864
Ser Phe Asn Gly Gln Gln Gly His Asn Tyr Thr Ile Glu Glu Ser Tyr
275                 280                 285
```

FIG. 9D

```
AAC CTG ACC GCT TCT TCC TGG CGC GAA GCC GAT GAC GTA AAC AGA CGG    912
Asn Leu Thr Ala Ser Ser Trp Arg Glu Ala Asp Asp Val Asn Arg Arg
290                 295                 300

CGC AAT GCC AAC CTC TTT TAC GAA TGG ACG CCT GAT TCA AAT TGG CTG    960
Arg Asn Ala Asn Leu Phe Tyr Glu Trp Thr Pro Asp Ser Asn Trp Leu
305                 310                 315                 320

TCG TCT TTG AAG GCG GAC TTC GAT TAT CAG ACA ACC AAA GTG GCG GCG   1008
Ser Ser Leu Lys Ala Asp Phe Asp Tyr Gln Thr Thr Lys Val Ala Ala
        325                 330                 335

GTT AAC AAC AAA GGC TCG TTC CCG ACG GAT TAT TCC ACC TGG ACG CGC   1056
Val Asn Asn Lys Gly Ser Phe Pro Thr Asp Tyr Ser Thr Trp Thr Arg
340                 345                 350

AAC TAT AAT CAG AAG GAT TTG GAG AAT ATA TAC AAC CGC AGC ATG GAC   1104
Asn Tyr Asn Gln Lys Asp Leu Glu Asn Ile Tyr Asn Arg Ser Met Asp
        355                 360                 365

ACC CGA TTC AAA CGT TTT ACT TTG CGT ATG GAC AGC CAA CCG TTG CAA   1152
Thr Arg Phe Lys Arg Phe Thr Leu Arg Met Asp Ser Gln Pro Leu Gln
370                 375                 380
```

FIG. 9E

```
CTG GGC GGC CAA CAT CGC TTG TCG CTT AAA ACT TTC GCC AGT CGG CGT    1200
Leu Gly Gly Gln His Arg Leu Ser Leu Lys Thr Phe Ala Ser Arg Arg
385                     390                 395                 400

GAG TTT GAA AAC TTA CGC GAC GAT TAT TAC TTC AGC GAA AGA GTA        1248
Glu Phe Glu Asn Leu Arg Asp Asp Tyr Tyr Phe Ser Glu Arg Val
        405                 410                 415

TCC CGT ACT ACC AGC ATT CAA CAC CCC GTG AAA ACC ACT AAT TAT        1296
Ser Arg Thr Thr Ser Ile Gln His Pro Val Lys Thr Thr Asn Tyr
    420                 425                 430

GGT TTC TCA CTG TCT GAT CAA ATC CAA TGG AAC GAC GTG TTC AGC AGC    1344
Gly Phe Ser Leu Ser Asp Gln Ile Gln Trp Asn Asp Val Phe Ser Ser
435                 440                 445

CGT GCA GAT ATC CGT TAC GAT CAT ACC AAA ATG ACG CCT CAG GAA TTG    1392
Arg Ala Asp Ile Arg Tyr Asp His Thr Lys Met Thr Pro Gln Glu Leu
450                 455                 460

AAT GCC GAG TGT CAT GCT TGT GAC AAA ACA CCG CCT GCA GCC AAT ACT    1440
Asn Ala Glu Cys His Ala Cys Asp Lys Thr Pro Pro Ala Ala Asn Thr
465                 470                 475                 480
```

FIG. 9F

| TAT | AAA | GGC | TGG | AGC | GGA | TTT | GTC | GGT | TTG | GCG | GCG | CAA | CTG | AAT | CAG | 1488 |
|---|---|---|---|---|---|---|---|---|---|---|---|---|---|---|---|---|
| Tyr | Lys | Gly | Trp | Ser | Gly | Phe | Val | Gly | Leu | Ala | Ala | Gln | Leu | Asn | Gln | |
| | | | | 485 | | | | 490 | | | | | 495 | | | |

| GCT | TGG | CAT | GTC | GGT | TAC | GAC | ATT | ACT | TCC | GGC | TAC | CGT | GTC | CCC | AAT | 1536 |
|---|---|---|---|---|---|---|---|---|---|---|---|---|---|---|---|---|
| Ala | Trp | His | Val | Gly | Tyr | Asp | Ile | Thr | Ser | Gly | Tyr | Arg | Val | Pro | Asn | |
| | | | 500 | | | | | 505 | | | | 510 | | | | |

| GCG | TCC | GAA | GTG | TAT | TTC | ACT | TAC | AAC | CAC | GGT | TCG | GGT | AAT | TGG | CTG | 1584 |
|---|---|---|---|---|---|---|---|---|---|---|---|---|---|---|---|---|
| Ala | Ser | Glu | Val | Tyr | Phe | Thr | Tyr | Asn | His | Gly | Ser | Gly | Asn | Trp | Leu | |
| | | 515 | | | | | 520 | | | | 525 | | | | | |

| CCC | AAT | CCC | AAC | CTG | AAA | GCC | GAG | CGC | AGC | ACC | ACC | CAC | ACC | CTG | TCT | 1632 |
|---|---|---|---|---|---|---|---|---|---|---|---|---|---|---|---|---|
| Pro | Asn | Pro | Asn | Leu | Lys | Ala | Glu | Arg | Ser | Thr | Thr | His | Thr | Leu | Ser | |
| | 530 | | | | | 535 | | | | 540 | | | | | | |

| CTG | CAA | GGC | CGC | AGC | GAA | AAA | GGT | ACT | TTG | GAT | GCC | AAC | CTG | TAT | CAA | 1680 |
|---|---|---|---|---|---|---|---|---|---|---|---|---|---|---|---|---|
| Leu | Gln | Gly | Arg | Ser | Glu | Lys | Gly | Thr | Leu | Asp | Ala | Asn | Leu | Tyr | Gln | |
| 545 | | | | | 550 | | | | | 555 | | | | | 560 | |

| AAC | AAT | TAC | CGC | AAC | TTC | TTG | TCT | GAA | GAG | CAG | AAG | CTG | ACC | ACC | AGC | 1728 |
|---|---|---|---|---|---|---|---|---|---|---|---|---|---|---|---|---|
| Asn | Asn | Tyr | Arg | Asn | Phe | Leu | Ser | Glu | Glu | Gln | Lys | Leu | Thr | Thr | Ser | |
| | | | 565 | | | | | 570 | | | | | 575 | | | |

FIG. 9G

```
GGC GAT GTC GGC TGT ACT CAG ATG AAT TAC TAC TAC GGT ATG TGT AGC    1776
Gly Asp Val Gly Cys Thr Gln Met Asn Tyr Tyr Tyr Gly Met Cys Ser
        580                 585                 590

AAT CCT TAT TCC GAA AAA CCG GAA TGG CAG ATG CAA AAT ATC GAT AAG    1824
Asn Pro Tyr Ser Glu Lys Pro Glu Trp Gln Met Gln Asn Ile Asp Lys
        595                 600                 605

GCC CGA ATC CGT GGT CTT GAG CTG ACA GGC CGT CTG AAT GTG ACA AAA    1872
Ala Arg Ile Arg Gly Leu Glu Leu Thr Gly Arg Leu Asn Val Thr Lys
        610                 615                 620

GTA GCG TCT TTT GTT CCT GAG GGC TGG AAA TTG TTC GGC TCG CTG GGT    1920
Val Ala Ser Phe Val Pro Glu Gly Trp Lys Leu Phe Gly Ser Leu Gly
        625                 630                 635                 640

TAT GCG AAA AGC AAA CTG TCG GGC GAC AAC AGC CTG CTG TCC ACA CAG    1968
Tyr Ala Lys Ser Lys Leu Ser Gly Asp Asn Ser Leu Leu Ser Thr Gln
        645                 650                 655

CCG CCG AAA GTG ATT GCC GGT GTC GAC TAC GAA AGC CCG AGC GAA AAA    2016
Pro Pro Lys Val Ile Ala Gly Val Asp Tyr Glu Ser Pro Ser Glu Lys
        660                 665                 670
```

FIG. 9H

```
TGG GGT GTG TTC TCC CGC CTG ACT TAT CTG GGT GCG AAA AAG GCC AAA         2064
Trp Gly Val Phe Ser Arg Leu Thr Tyr Leu Gly Ala Lys Lys Ala Lys
675                 680                 685

GAC GCG CAA TAC ACC GTT TAT GAA AAC AAG GGC CGG GGT ACG CCT TTG         2112
Asp Ala Gln Tyr Thr Val Tyr Glu Asn Lys Gly Arg Gly Thr Pro Leu
690                 695                 700

CAG AAA AAG GTA AAA GAT TAC CCG TGG CTG AAC TCG GCT TAT GTG             2160
Gln Lys Lys Val Lys Asp Tyr Pro Trp Leu Asn Ser Ala Tyr Val
705                 710                 715                 720

TTT GAT ATG TAC GGC TTC TAC AAA CTG GCT AAA AAC CTG ACT TTG CGT         2208
Phe Asp Met Tyr Gly Phe Tyr Lys Leu Ala Lys Asn Leu Thr Leu Arg
725                 730                 735

GCA GGC GTA TAT AAT GTG TTC AAC CGC AGG TAC ACC ACT TGG GAT TCC         2256
Ala Gly Val Tyr Asn Val Phe Asn Arg Lys Tyr Thr Thr Trp Asp Ser
740                 745                 750

CTG CGC GGT TTG TAT AGC TAC AGC TAC ACC AAC GCG GTC GAC CGA GAT         2304
Leu Arg Gly Leu Tyr Ser Tyr Ser Tyr Thr Asn Ala Val Asp Arg Asp
755                 760                 765
```

FIG. 9I

```
                                                                              2352
GGC AAA GGC TTA GAC CGC TAC CGC GCC TCA GGC CGT AAT TAC GCC GTA
Gly Lys Gly Leu Asp Arg Tyr Arg Ala Ser Gly Arg Asn Tyr Ala Val
        770                 775                 780

2378
TCG CTG GAT TGG AAG TTT TGA ATTCC
Ser Leu Asp Trp Lys Phe  *
        785             790
```

FIG. 11A

```
HMBRA     MKPLQMLPIAALVGSIFGNPVLAADEAATETTPVKAEIKAVRVKGQRNAP  50
HMBRB     MKPLQMPPIAALLGSIFGNPVFAXDEAATETTPVKAEVKAVRVKGQRNAP  50
HMBRC     MKPLQMLPIAALVGSIFGNPVFAADEAATETTPVKAEVKAVRVKGQRNAP  50
HMBRMS11  MKPLHMLPIAALVGSIFGNPVLAADEAATETTPVKAEIKEVRVKDQLNAP  50
          ****. *****.********: *******************:*. *  ***

HMBRA     AAVERVNLNRIKQEMIRDNKDLVRYSTDVGLSDSGRHQKGFAVRGVEGNR  100
HMBRB     AAVERVNLNRIKQEMIRDNKDLVRYSTDVGLSDSDRSRHQKGFAIRGVEGDR  100
HMBRC     AAVERVNLNRIKQEMIRDNKDLVRYSTDVGLSDSGRHQKGFAVRGVEGNR  100
HMBRMS11  ATVERVNLGRIQQEMIRDNKDLVRYSTDVGLSDSGRHQKGFAVRGVEGNR  100
          *.******. **:*******************.. ******:*****.

HMBRA     VGVSIDGVNLPDSEENSLYARYGNFNSSRLSIDPELVRNIEIVKGADSFN  150
HMBRB     VGVSIDGVNLPDSEENSLYARYGNFNSSRLSIDPELVRNIDIVKGADSFN  150
HMBRC     VGVSIDGVNLPDSEENSLYARYGNFNSSRLSIDPELVRNIDIVKGADSFN  150
HMBRMS11  VGVSIDGVSLPDSEENSLYARYGNFNSSRLSIDPELVRNIEIAKGADSFN  150
          ********. ***************************** *.*******

HMBRA     TGSGALGGGVNYQTLQGRDLLLDDRQFGVMMKNGYSTRNREWTNTLGFGV  200
HMBRB     TGSGALGGGVNYQTLQGRDLLLPERQFGVMMKNGYSTRNREWTNTLGFGV  200
HMBRC     TGSGALGGGVNYQTLQGRDLLLPERQFGVMMKNGYSTRNREWTNTLGFGV  200
HMBRMS11  TGSGALGGGVNYQTLQGHDLLLDDRQFGVMMKNGYSSRNREWTNTLGFGV  200
          *****************.*** ************:*************
```

FIG. 11B

```
HMBRA      SNDRVDAALLYSQRRGHETESAGNRGYPVEGAGKETNIRGSARGIPDPSK  250
HMBRB      SNDRVDAALLYSQRRGHETESAGKRGYPVEGAGSGANIRGSARGIPDPSQ  250
HMBRC      SNDRVDAALLYSQRRGHETESAGKRGYPVEGAGSGANIRGSARGIPDPSQ  250
HMBRMS11   SNDRVDAALLYSQRRGHETESAGERGYPVEGAGSGAIIRGSSRGIPDPSK  250
           ****************************.**************.******.

HMBRA      HKYHNFLGKIAYQINDNHRIGASLNGQQGHNYTVEESYNLTASSWREADD  300
HMBRB      HKYHSFLGKIAYQINDNHRIGASLNGQQGHNYTVEESYNLLASYWREADD  300
HMBRC      HKYHSFLGKIAYQINDNHRIGASLNGQQGHNYTVEESYNLLASYWREADD  300
HMBRMS11   HKYHNFLGKIAYQINDKHRIGPSFNGQQGHNYTIEESYNLTASSWREADD  300
           ****.***********.****.*.*********.*****.**.******

HMBRA      VNRRRNANLFYEWMPDSNWLSSLKADFDYQKTKVAAIN-KGSFPT-NYTT  348
HMBRB      VNRRRNTNLFYEWTPESDRLSMVKADVDYQKTKVSAVNYKGSFPT-NYTT  349
HMBRC      VNRRRNTNLFYEWTPESDRLSMVKADVDYQKTKVSAVNYKGSFPIEDSST  350
HMBRMS11   VNRRRNANLFYEWTPDSNWLSSLKADFDYQTTKVAAVNNKGSFPTD-YST  349
           ******.****** *:*:: *:****.***.:**:*:* *****  : *

HMBRA      WETEYHKKEVGEIYNRSMDTRFKRFTLRLDSHPLQLGGGRHRLSFKTFAS  398
HMBRB      WETEYHKKEVGEIYNRSMDTRFKRITLRMDSHPLQLGGGRHRLSFKTFAG  399
HMBRC      LTRNYNQKDLDEIYNRSMDTTFKRITLRMDSHPLQLGGGRHRLSFKTFAS  400
HMBRMS11   WTRNYNQKDLENIYNRSMDTRFKRFTLRMDSQPLQLGG-RHRLSLKTFAS  398
           :  *..*: :.:*******.***.***:** *******  ****:****.
```

FIG. 11C

```
HMBRA      RRDFENLNRDDYFSGRVVRTTSSIQHPVKTTNYGFSLSDQIQWNDVFSS    448
HMBRB      QRDFENLNRDDYFSGRVVRTTNSIQHPVKTTNYGFSLSDQIQWNDVFSS    449
HMBRC      RRDFENLNRDDYFSGRVVRTTSSIQHPVKTTNYGFSLSDQIQWNDVFSS    450
HMBRMS11   RREFENLNRDDYFSERVSRTTSSIQHPVKTTNYGFSLSDQIQWNDVFSS    448
           .*.*************.** .** **********************

HMBRA      RAGIRYDHTKMTPQELNAECHACDKTPPAANTYKGWSGFVGLAAQLNQAW   498
HMBRB      RAGIRYDHTKMTPQELNADCHACDKTPPAANTYKGWSGFVGLAAQLSQTW   499
HMBRC      RAGIRYDHTKMTPQELNAECHACDKTPPAANTYKGWSGFVGLAAQLNQAW   500
HMBRMS11   RADIRYDHTKMTPQELNADCHACDKTPPAANTYKGWSGFVGLAAQLNQAW   498
           **.***************.*********************** . *

HMBRA      RVGYDITSGYRVPNASEVYFTYNHGSGNWLPNPNLKAERSTTHTLSLQGR   548
HMBRB      RVGYDVTSGFRVPNASEVYFTYNHGSGTWKPNPNLKAERSTTHTLSLQGR   549
HMBRC      RVGYDITSGYRVPNASEVYFTYNHGSGNWLPNPNLKAERTTHTLSLQGR    550
HMBRMS11   HVGYDITSGYRVPNASEVYFTYNHGSGNWLPNPNLKAERSTTHTLSLQGR   548
            .***.***.*****************.* ********.*********

HMBRA      SEKGMLDANLYQSNYRNFLSEEQKLTTSGTPGCTEENAYYSICSDPYKEK   598
HMBRB      GDKGTLDANLYQSNYRNFLSEEQNLTVSGTPGCTEEDAYYRCSDPYKEK    599
HMBRC      SEKGTLDANLYQSNYRNFLSEEQKLTTSGDVSCTQMNYYYGMCSNPYSEK   600
HMBRMS11   SEKGTLDANLYQNNYRNFLSEEQNLTTSGDVGCTQMNYYYGMCSNPYSEK   598
           ..** ******* *********. **.**.. **. .** .* ***.**
```

FIG. 11D

```
HMBRA     LDWQMKNIDKARIRGIELTGRLNVDKVASFVPEGWKLFGSLGYAKSKLSG   648
HMBRB     LDWQMKNIDKARIRGIELTGRLNVDKVASFVPEGWKLFGSLGYAKSKLSG   649
HMBRC     LDWQMQNIDKARIRGLELTGRLNVDKVASFVPEGWKLFGSLGYAKSKLSG   650
HMBRMS11  PEWQMQNIDKARIRGLELTGRLNVTKVASFVPEGWKLFGSLGYAKSKLSG   648
          ..*****:******* ******.******************:********

HMBRA     DNSLLSTQPLKVIAGIDYESPSEKWGVFSRLTYLGAKKVKDAQYTVYENK   698
HMBRB     DNSLLSTQPLKVIAGIDYESPSEKWGVFSRLTYLGAKKVKDAQYTVYENK   699
HMBRC     DNSLLSTQPLKVIAGIDYESPSEKWGVFSRLTYLGAKKVKDAQYTVYENK   700
HMBRMS11  DNSLLSTQPPKVIAGVDYESPSEKWGVFSRLTYLGAKKAKDAQYTVYENK   698
          ********* *****:*********************.************

HMBRA     GWGTPLQKKVVKDYPWLNKSAYVFDMYGFYKPVKNLTLRAGVYNLFNRKYT   748
HMBRB     GWGTPLQKKVVKDYPWLNKSAYVFDMYGFYKPVKNLTLRAGVYNLFNRKYT   749
HMBRC     GWGTPLQKKVVKDYPWLNKSAYVFDMYGFYKPAKNLTLRAGVYNLFNRKYT   750
HMBRMS11  GRGTPLQKKVVKDYPWLNKSAYVFDMYGFYKLAKNLTLRAGVYNVFNRKYT   748
          * ****************************  .*********** *****

HMBRA     TWDSLRGLYSYSTTNAVDRDGKGLDRYRAPGRNYAVSLEWKF   790
HMBRB     TWDSLRGLYSYSTTNAVDRDGKGLDRYRAPGRNYAVSLEWKF   791
HMBRC     TWDSLRGLYSYSTTNSVDRDGKGLDRYRAPSRNYAVSLEWKF   792
HMBRMS11  TWDSLRGLYSYSTTNAVDRDGKGLDRYRASGRNYAVSLDWKF   790
          ***************.*************.  ******:***
```

BACTERIAL HEMOGLOBIN RECEPTOR GENES

This application is a continuation of U.S. Ser. No. 08/537,361, filed Oct. 2, 1995, now U.S. Pat. No. 6,121,037, issued Sep. 19, 2000, which is a continuation-in-part of U.S. Ser. No. 08/326,670, filed Oct. 18, 1994, now U.S. Pat. No. 5,698,438, issued Dec. 16, 1997. The disclosures of each of these prior applications are considered as being part of the disclosure of the application and are explicitly incorporated by reference herein.

BACKGROUND OF THE INVENTION

1. Field of the Invention

This invention relates to hemoglobin receptor genes and the proteins encoded therefrom of certain bacterial species, particularly species of *Neisseria* bacteria. More particularly, this invention relates to hemoglobin receptor genes, polypeptides and peptides useful for preparing vaccines and antibodies against *Neisseria*, and methods and means for producing such peptides and polypeptides in vitro. Also provided are diagnostic and therapeutic methods and reagents useful in detecting and treating *Neisseria* infection and methods for developing novel and effective anti-*Neisseria* agents.

2. Background of the Invention

The *Neisseriae* comprise a genus of bacteria that includes two gram-negative species of pyogenic cocci pathogenic for humans: *Neisseria meningitidis* and *Neisseria gonorrhoeae*. *N. meningitidis* is a major cause of bacterial meningitis in humans, especially children. The disease characteristically proceeds from asymptomatic carriage of the bacterium in the nasopharynx to invasion of the bloodstream and cerebrospinal fluid in susceptible individuals.

*Neisseria meningitidis* is one of the leading causes of bacterial meningitis in children and healthy adults in the world. The severity of the disease is evidenced by the ability of meningococci to cause the death of previously healthy individuals in less than 24 hours. *N. meningitidis* has a polysaccharide capsule whose diversity of component antigenic polysaccharide molecules has resulted in the classification of ten different serogroups. Of these, group A strains are the classic epidemic strains; group B and C are generally endemic strains, but C occasionally causes an epidemic outbreak. All known group A strains have the same protein antigens on their outer membranes, while group B strains have a dozen serotypes or groupings based on the presence of principal outer membrane protein antigens (as opposed to polysaccharides).

Survival of a pathogen such as *N. meningitidis* in a host depends on its ability to overcome a battery of host defense mechanisms. One nonspecific host defense mechanism against microbial intruders is to limit the availability of iron in tissues (Weinberg, 1984, *Physiological. Rev.* 64: 65–102), because iron is a necessary nutrient for most microbial pathogens. The vast majority of iron in the human adult is located intracellularly in the form of hemoglobin (76%) or ferritin (23%). The remainder can be found extracellularly bound to host iron-binding proteins such as transferrin and lactoferrin (Otto et al., 1992, *Crit. Rev. Microbiol.* 18: 217–233).

Pathogenic bacteria have adapted to this iron-limiting environment by developing highly specific and effective iron assimilation systems. A large number of these bacteria secrete siderophores, small, non-protein iron chelators which, due to their extremely high affinity for iron (III), scavenge trace amounts of iron(III) from the environment and shuttle the iron back to the bacterial cell (Baggs and Neilands, 1987, *Microbiol. Rev.* 51: 509–518; Braun and Hantke, 1991, in Winkelmann (ed.), *Handbook of Microbial Iron Chelates*, CRC Press: Boca Raton, Fla., pp. 107–138.).

Alternatively, some bacterial pathogens, like *Neisseriae* species (Archibald and DeVoe, 1979, *FEMS Microbiol. Lett.* 6: 159–162; Mickelson et al., 1982, *Infect. Immun.* 35: 915–920; Dyer et al., 1987, *Infect. Immun.* 55: 2171–2175), *Haemophilus influenzae* (Coulton and Pang, 1983, *Curr. Microbiol.* 9: 93–98; Schryvers, 1988, *Mol. Microbiol.* 2: 467–472; Jarosik et al., 1994, *Infect. Immun.* 62: 2470–2477), *Vibrio cholerae* (Stoebner and Payne, 1988, *Infect. Immun.* 56: 2891–2895; Henderson and Payne, 1994, *J. Bacteriol.* 176: 3269–3277), *Yersiniae* (Stojiljkovic and Hantke, 1992, *EMBO J.* 11: 4359–4367) and *Actinobacillus pleuropneumoniae* (Gerlach et al., 1992, *Infect. Immun.* 60: 3253–3261) have evolved more sophisticated mechanisms to sequester iron from the host. These pathogens can directly bind host's iron-binding proteins such as lactoferrin, transferrin, and heme-containing compounds, and use them as sole sources of iron.

The importance of iron in the virulence of *N. meningitidis* was demonstrated by in vivo studies using mice as the animal model system (Calver et al., 1976, *Can. J. Microbiol.* 22: 832–838; Holbien et al., 1981, *Infect. Immun.* 34: 120–125). Specific iron-regulated outer membrane receptors have been shown to be involved in the binding and the utilization of lactoferrin- and transferrin-iron in *Neisseriae* (Schryvers and Morris, 1988, *Infect. Immun.* 56: 1144–1149 and *Mol. Microbiol.* 2: 281–288; Legrain et al., 1993, *Gene* 130: 81–90; Pettersson et al., 1993, *Infect. Immun.* 61: 4724–4733 and 1994, *J. Bacteriol.* 176: 1764–1766). These receptors share significant amino acid similarity and, most probably, also the mechanism of iron internalization, with receptors for siderophores and vitamin B12 of other Gram-negative bacteria (Cornelissen et al., 1993, *J. Bacteriol.* 174: 5788–5797). In contrast, the mechanism by which *Neisseriae* utilize hemoglobin- and hemin-iron as well as the components involved have so far not been described.

Recently, several proteins with hemoglobin-binding and/or hemin-binding activities have been identified in total membranes of iron-limited *N. meningitidis* and *N. gonorrhoeae*.

Lee and Hill, 1992, *J. gen. Microbiol.* 138: 2647–2656 disclose the specific hemoglobin binding by isolated outer membranes of *N. meningitidis*.

Martek and Lee, 1994, *Infect. Immun.* 62: 700–703 disclosed that acquisition of heme iron by *N. meningitidis* does not involve meningococcal transferrin-binding proteins.

Lee, 1994, *Microbiol.* 140: 1473–1480 describes the biochemical isolation and characterization of hemin binding proteins from *N. meningitidis*.

The precise role of these proteins in hemin and/or hemoglobin utilization remains unclear at present, although these proteins are likely to be components of a hemin-utilization system in *N. meningitidis*.

The dependence on host iron stores for *Neisseria* growth is a potentially useful route towards the development of novel and effective therapeutic intervention strategies. Historically, infections of both *N. meningitidis* and *N. gonorrhoeae* were treated chemoprophylactically with sulfonamide drugs. However, with the development of sulfonamide-resistant strains came the necessity of using alternative modes of therapy such as antibiotic treatment. More recently, the drug treatment of choice includes the administration of high grade penicillin. However, the success of antimicrobial treatment is decreased if therapy is not initiated early after infection.

Gonococcal infection has also been treated with penicillin, ampicillin, or amoxicillin, tetracycline hydrochloride, and spectinomycin. Unfortunately, because the incidence of infections due to penicillinase-producing bacteria has increased, several new, more expensive β-lactam antibiotics have been used in treatment. Despite the fact that existing antibiotics have decreased the serious consequences of gonorrhea, their use has not lowered the incidence of the infection in the general population.

Prevention of meningococcal disease has been attempted by chemoprophylaxis and immunoprophylaxis. At present, rifampin and minocycline are used, but only for humans in close contact with an infected person as this treatment has a number of disadvantages. The only commercially available vaccine against meningococcal meningitis has as its major component the bacterial polysaccharide capsule. In adults this vaccine protects against serogroups A, C, Y and W135. It is not effective against serogroup B, and is ineffective in children against serogroup C. Thus far, immunoprophylatic preventive treatment has not been available for *N. gonorrhoeae*.

Thus, what is needed are better preventative therapies for meningococcal meningitis and gonorrhea including more effective, longer lasting vaccines which protect across all of the serogroups of *N. meningitidis* and all the serotypes of *N. gonorrhoeae*. In addition, better methods are need to treat meningococcal and gonococcal infection.

SUMMARY OF THE INVENTION

The present invention relates to the cloning, expression and functional characterization of genes encoding bacterial hemoglobin receptor proteins. Specifically, the invention relates to genes encoding hemoglobin receptor proteins from *Neisseria* species, in particular *Neisseria meningitidis* and *N. gonorrhoeae*. The invention comprises species of nucleic acids having a nucleotide sequence encoding novel bacterial hemoglobin receptor proteins. Also provided by this invention is the deduced amino acid sequence of the cognate hemoglobin receptor proteins of these bacterial genes.

The invention provides nucleic acids, nucleic acid hybridization probes, recombinant expression constructs capable of expressing the hemoglobin receptor protein of the invention in cultures of transformed cells, preferably bacterial cells, and such cultures of transformed bacterial cells that express the hemoglobin receptor proteins of the invention. The invention also provides gene knockout vectors for inactivating the hemoglobin receptor protein gene in cells, particularly cells of *Neisseria* species, via, for example, homologous recombination and other mechanisms, and cultures of such hemoglobin receptor protein null mutant cells.

The invention also provides homogeneous preparations of the bacterial hemoglobin receptor proteins of the invention, as well as antibodies against and epitopes of the hemoglobin receptor protein. Methods for characterizing this receptor protein and methods for using the protein in the development of agents having pharmacological uses related to this receptor, particularly bactericidal and bacteriostatic uses, are also provided by the invention.

In other embodiments of this invention are provided diagnostic methods and reagents encompassing the use of the anti-*Neisseria* hemoglobin receptor protein antibodies of the invention. Still further embodiments provided herein include therapeutic methods and reagents encompassing the use of the anti-*Neisseria* hemoglobin receptor protein antibodies of the invention. Even more embodiments include diagnostic methods and reagents encompassing the use of the *Neisseria* hemoglobin receptor protein-encoding nucleic acids of the invention, as sensitive probes for the presence of *Neisseria* infection using nucleic acid hybridization techniques and/or in vitro amplification methodologies. Yet additional embodiments of the invention include therapeutic methods and reagents encompassing the use of the *Neisseria* hemoglobin receptor protein-encoding nucleic acids of the invention, comprising recombinant expression constructs engineered to produce antisense transcripts of the *Neisseria* hemoglobin receptor gene and fragments thereof, as well as recombinant knockout vectors of the invention. The invention also provides the *Neisseria* hemoglobin receptor protein and epitopes thereof as components of vaccines for the development of non-disease associated immunity to pathological infection with bacteria of *Neisseria* species.

In a first aspect, the invention provides a nucleic acid having a nucleotide sequence encoding a bacterial hemoglobin receptor protein gene. In a preferred embodiment, the bacterial hemoglobin receptor protein gene is isolated from bacteria of *Neisseria* species. In a particularly preferred embodiment, the hemoglobin receptor protein gene is isolated from *Neisseria meningitidis*, serotype C. In a particular example of this embodiment, the nucleic acid comprises a 3.3 kilobase (kb) BamHI/HindIII fragment of *N. meningitidis* genomic DNA. In this embodiment, the nucleotide sequence comprises an open reading frame of 2376 nucleotides of *N. meningitidis* genomic DNA encoding 792 amino acids comprising the hemoglobin receptor gene. In this embodiment of the invention, the nucleotide sequence of the *N. meningitidis* hemoglobin receptor gene is the sequence depicted in FIGS. 2A–2H (SEQ ID No:1). It will be understood that the *N. meningitidis* gene as disclosed herein is defined, insofar as is necessary, by the amino acid sequence of the protein encoded therein, said amino acid sequence being represented in FIGS. 2A–2H (SEQ ID No.:2). Thus, it will be understood that the particular nucleotide sequence depicted in FIGS. 2A–2H (SEQ ID No.:1) is but one of a number of equivalent nucleotide sequences that encode the hemoglobin receptor protein, due to the degeneracy of the genetic code, and that all such alternative, equivalent nucleotide sequences are hereby explicitly encompassed within the disclosed nucleotide sequences of the invention. Also included herein are any mutant or allelic variations of this nucleotide sequence, either naturally occurring or the product of in vitro chemical or genetic modification. Each such variant will be understood to have essentially the same nucleotide sequence as the nucleotide sequence of the corresponding *N. meningitidis* hemoglobin receptor protein disclosed herein.

In another particularly preferred embodiment of this aspect of the invention, the hemoglobin receptor protein gene is isolated from *Neisseria meningitidis*, serotype A. In a particular example of this embodiment, the nucleic acid comprises a 2373 basepair (bp) polymerase chain reaction-amplified fragment of *N. meningitidis*, serotype A genomic DNA. In this embodiment, the nucleotide sequence comprises an open reading frame of 2373 nucleotides of *N. meningitidis* genomic DNA encoding 790 amino acids comprising the hemoglobin receptor gene. In this embodiment of the invention, the nucleotide sequence of the *N. meningitidis* hemoglobin receptor gene is the sequence depicted in FIGS. 7A–7I (SEQ ID No:3). It will be understood that the *N. meningitidis* gene as disclosed herein is defined, insofar as is necessary, by the amino acid sequence of the protein encoded therein, said amino acid sequence being represented in FIGS. 7A–7I (SEQ. ID No.:4). Thus, it will be understood that the particular nucleotide sequence depicted in FIGS. 7A–7I (SEQ. ID. No.:3) is but one of a number of equivalent nucleotide sequences that encode the hemoglobin receptor protein, due to the degeneracy of the genetic code, and that all such alternative, equivalent nucleotide sequences are hereby explicitly encompassed within the disclosed nucleotide sequences of the invention. Also included herein are any mutant or allelic variations of this nucleotide sequence, either naturally occurring or the product of in vitro chemical or genetic modification. Each such variant will be understood to have essentially the same nucleotide sequence as the nucleotide sequence of the corresponding *N. meningitidis* hemoglobin receptor protein disclosed herein.

In another particularly preferred embodiment of this aspect of the invention, the hemoglobin receptor protein gene is isolated from *Neisseria meningitidis*, serotype B. In a particular example of this embodiment, the nucleic acid comprises a 2376 basepair (bp) polymerase chain reaction-amplified fragment of *N. meningitidis*, serotype A genomic DNA. In this embodiment, the nucleotide sequence comprises an open reading frame of 2373 nucleotides of *N. meningitidis* genomic DNA encoding 791 amino acids comprising the hemoglobin receptor gene. In this embodiment of the invention, the nucleotide sequence of the *N. meningitidis* hemoglobin receptor gene is the sequence depicted in FIGS. 8A–8I (SEQ ID No:5). It will be understood that the *N. meningitidis* gene as disclosed herein is defined, insofar as is necessary, by the amino acid sequence of the protein encoded therein, said amino acid sequence being represented in FIGS. 8A–8I (SEQ. ID. No.:6). Thus, it will be understood that the particular nucleotide sequence depicted in FIGS. 8A–8I (SEQ. ID. No.:5) is but one of a number of equivalent nucleotide sequences that encode the hemoglobin receptor protein, due to the degeneracy of the genetic code, and that all such alternative, equivalent nucleotide sequences are hereby explicitly encompassed within the disclosed nucleotide sequences of the invention. Also included herein are any mutant or allelic variations of this nucleotide sequence, either naturally occurring or the product of in vitro chemical or genetic modification. Each such variant will be understood to have essentially the same nucleotide sequence as the nucleotide sequence of the corresponding *N. meningitidis* hemoglobin receptor protein disclosed herein.

In yet other preferred embodiments, the invention provides nucleic acid encoding a hemoglobin receptor protein gene isolated from *Neisseria gonorrhoeae*. In a particular example of this embodiment, the nucleic acid comprises a 2378 basepair (bp) polymerase chain reaction-amplified fragment of *N. gonorrhoeae* genomic DNA. In this embodiment, the nucleotide sequence comprises an open reading frame of 2373 nucleotides of *N. gonorrhoeae* genomic DNA encoding 791 amino acids comprising the hemoglobin receptor gene. In this embodiment of the invention, the nucleotide sequence of the *N. gonorrhoeae* hemoglobin receptor gene is the sequence depicted in FIGS. 9A–9I (SEQ ID No:7). It will be understood that the *N. gonorrhoeae* gene as disclosed herein is defined, insofar as is necessary, by the amino acid sequence of the protein encoded therein, said amino acid sequence being represented in FIGS. 9A–9I (SEQ. ID. No.:8). Thus, it will be understood that the particular nucleotide sequence depicted in FIGS. 9A–9I (SEQ. ID. No.:7) is but one of a number of equivalent nucleotide sequences that encode the hemoglobin receptor protein, due to the degeneracy of the genetic code, and that all such alternative, equivalent nucleotide sequences are hereby explicitly encompassed within the disclosed nucleotide sequences of the invention. Also included herein are any mutant or allelic variations of this nucleotide sequence, either naturally occurring or the product of in vitro chemical or genetic modification. Each such variant will be understood to have essentially the same nucleotide sequence as the nucleotide sequence of the corresponding *N. gonorrhoeae* hemoglobin receptor protein disclosed herein.

The invention also provides bacterial hemoglobin receptor proteins. In a preferred embodiment, the bacterial hemoglobin receptor protein is isolated from bacteria of *Neisseria* species. In a particularly preferred embodiment, the hemoglobin receptor protein is isolated from *Neisseria meningitidis*. In a particular example of this embodiment, the protein is derived from *N. meningitidis*, serotype C and comprises an amino acid sequence of 792 amino acids. In this embodiment of the invention, the amino acid sequence of the *N. meningitidis*, serotype C hemoglobin receptor protein is the sequence depicted in FIGS. 2A–2H (SEQ ID No:2).

In another example of this embodiment, the protein is derived from *N. meningitidis*, serotype A and comprises an amino acid sequence of 790 amino acids. In this embodiment of the invention, the amino acid sequence of the *N. meningitidis*, serotype A hemoglobin receptor protein is the sequence depicted in FIGS. 7A–7I (SEQ ID No:4). In yet another example of this embodiment, the protein is derived from *N. meningitidis*, serotype B and comprises an amino acid sequence of 791 amino acids. In this embodiment of the invention, the amino acid sequence of the *N. meningitidis*, serotype B hemoglobin receptor protein is the sequence depicted in FIGS. 8A–8I (SEQ ID No:6). The invention also provides hemoglobin receptor protein derived from *N. gonorrhoeae*. In this embodiment of the invention, the protein comprises an amino acid sequence of 791 amino acids, and the amino acid sequence of the *N. gonorrhoeae* hemoglobin receptor protein is the sequence depicted in FIGS. 9A–9I (SEQ ID No:8). Also explicitly encompassed within the scope of this invention are related bacterial hemoglobin receptor proteins, particularly such proteins isolated from *Neisseria* species, having essentially the same amino acid sequence and substantially the same biological properties as the hemoglobin receptor protein encoded by the *N. meningitidis* and *N. gonorrhoeae* nucleotide sequences described herein.

In another aspect, the invention provides a homogeneous preparation of an approximately 85.5 kiloDalton (kD) bacterial hemoglobin receptor protein or derivative thereof, said size being understood to be the size of the protein before any post-translational modifications thereof. Also provided is a 90 kD embodiment of the receptor as determined by sodium dodecyl sulfate/polyacrylamide gel electrophoresis under reducing conditions. In a preferred embodiment, the bacterial hemoglobin receptor protein is isolated from bacteria of *Neisseria* species. In a particularly preferred embodiment, the hemoglobin receptor protein is isolated from *Neisseria meningitidis*. In one embodiment of this aspect of the invention, the protein is isolated from *N. meningitidis*, serotype C and the amino acid sequence of the bacterial hemoglobin receptor protein or derivative thereof preferably is the amino acid sequence of the hemoglobin receptor protein shown in FIGS. 2A–2H (SEQ ID No:2). In a second embodiment of this aspect of the invention, the protein is isolated from *N. meningitidis*, serotype A and the amino acid sequence of the bacterial hemoglobin receptor protein or derivative thereof preferably is the amino acid sequence of the hemoglobin receptor protein shown in FIGS. 7A–7I (SEQ ID No:4). In a third embodiment of this aspect of the invention, the protein is isolated from *N. meningitidis*, serotype B and the amino acid sequence of the bacterial hemoglobin receptor protein or derivative thereof preferably is the amino acid sequence of the hemoglobin receptor protein shown in FIGS. 8A–8I (SEQ ID No:6). The invention also provides a homogeneous preparation of a bacterial hemoglobin receptor protein isolated from *N. gonorrhoeae*. In a preferred embodiment, the amino acid sequence of the bacterial hemoglobin receptor protein or derivative thereof preferably is the amino acid sequence of the hemoglobin receptor protein shown in FIGS. 9A–9I (SEQ ID No:8).

This invention provides nucleotide probes derived from the nucleotide sequences herein provided. The invention includes probes isolated from either complementary DNA (cDNA) copies of bacterial messenger RNA (mRNA) or bacterial genomic DNA (gDNA), as well as probes made synthetically or by in vitro amplification methods using the sequence information provided herein. The invention specifically includes but is not limited to oligonucleotide, nick-translated, random primed, or in vitro amplified probes made using cDNA or genomic clones embodying the invention, and oligonucleotide and other synthetic probes synthesized chemically using the nucleotide sequence information of cDNA or genomic clone embodiments of the invention.

It is a further object of this invention to provide such nucleic acid hybridization probes to detect the presence of bacteria of *Neisseria* species, particularly *N. meningitidis* and *N. gonorrhoeae*, in a biological sample in the diagnosis of a *Neisseria* infection in a human. Such a biological sample preferably includes blood, urine, semen, mucus, cerebrospinal fluid, peritoneal fluid and ascites fluids, as well as cell scrapings from the epithelium of the mouth, urethra, anus and rectum, and other organs.

The present invention also includes peptides encoded by the nucleotide sequences comprising the nucleic acid embodiments of the invention. The invention includes either naturally occurring or synthetic peptides which may be used as antigens for the production of hemoglobin receptor protein-specific antibodies. The invention also comprises such antibodies, preferably monoclonal antibodies, and cells and cultures of cells producing such antibodies.

Thus, the invention also provides antibodies against and epitopes of bacterial hemoglobin receptor proteins of the invention. It is an object of the present invention to provide antibodies that are immunologically reactive to the bacterial hemoglobin receptor proteins of the invention. It is a particular object to provide monoclonal antibodies against these bacterial hemoglobin receptor proteins. In a preferred embodiment, antibodies provided are raised against bacterial hemoglobin receptor protein isolated from bacteria of *Neisseria* species. In a particularly preferred embodiment, such antibodies are specific for the hemoglobin receptor protein isolated from *Neisseria meningitidis* serotypes A, B or C. In additional particularly preferred embodiment, such antibodies are specific for the hemoglobin receptor protein isolated from *Neisseria gonorrhoeae*.

Hybridoma cell lines producing such antibodies are also objects of the invention. It is envisioned that such hybridoma cell lines may be produced as the result of fusion between a non-immunoglobulin producing mouse myeloma cell lines and spleen cells derived from a mouse immunized with purified hemoglobin receptor protein or a cell expressing antigens or epitopes of bacterial hemoglobin receptor proteins of the invention. The present invention also provides hybridoma cell lines that produce such antibodies, and can be injected into a living mouse to provide an ascites fluid from the mouse that is comprised of such antibodies. In a preferred embodiment, antibodies provided are raised against bacterial hemoglobin receptor protein isolated from bacteria of *Neisseria* species. In a particularly preferred embodiment, such antibodies are specific for the hemoglobin receptor protein isolated from *Neisseria meningitidis*, serotypes A, B or C. In additional particularly preferred embodiment, such antibodies are specific for the hemoglobin receptor protein isolated from *Neisseria gonorrhoeae*.

It is a further object of the invention to provide immunologically-active epitopes of the bacterial hemoglobin receptor proteins of the invention. Chimeric antibodies immunologically reactive against the bacterial hemoglobin receptor proteins of the invention are also within the scope of this invention. In a preferred embodiment, antibodies and epitopes provided are raised against or derived from bacterial hemoglobin receptor protein isolated from bacteria of *Neisseria* species. In a particularly preferred embodiment, such antibodies and epitopes are specific for the hemoglobin receptor protein isolated from *Neisseria meningitidis*, serotypes A, B or C. In additional particularly preferred embodiment, such antibodies and epitopes are specific for the hemoglobin receptor protein isolated from *Neisseria gonorrhoeae*.

The present invention provides recombinant expression constructs comprising a nucleic acid encoding a bacteria hemoglobin receptor protein wherein the construct is capable of expressing the encoded hemoglobin receptor protein in cultures of cells transformed with the construct. Preferred embodiments of such constructs comprise the *N. meningitidis*, serotype C hemoglobin receptor gene depicted in FIGS. 2A–2H (SEQ ID No.:1), such constructs being capable of expressing the bacterial hemoglobin receptor protein encoded therein in cells transformed with the construct. Additional preferred embodiments of such constructs comprise the *N. meningitidis*, serotype A hemoglobin receptor gene depicted in FIGS. 7A–7I (SEQ ID No.:3), such constructs being capable of expressing the bacterial hemoglobin receptor protein encoded therein in cells transformed with the construct. Further additional preferred embodiments of such constructs comprise the *N. meningitidis*, serotype B hemoglobin receptor gene depicted in FIGS. 8A–8I (SEQ ID No.:5), such constructs being capable of expressing the bacterial hemoglobin receptor protein encoded therein in cells transformed with the construct. The invention also provides recombinant expression constructs encoding a hemoglobin receptor protein gene isolted from *ZN. gonorrhoeae*. In a particularly preferred embodiment, such constructs comprise the *N. gonorrhoeae* hemoglobin receptor gene depicted in FIGS. 9A–9I (SEQ ID No.:7), the constructs being capable of expressing the bacterial hemoglobin receptor protein encoded therein in cells transformed with the construct.

The invention also provides cultures of cells, preferably bacterial cells, having been transformed with the recombinant expression constructs of the invention, such cultures being capable of and in fact expressing the bacterial hemoglobin receptor protein encoded in the transforming construct.

The present invention also includes within its scope protein preparations of prokaryotic cell membranes containing the bacterial hemoglobin receptor protein of the invention, derived from cultures of prokaryotic cells transformed with the recombinant expression constructs of the invention.

The invention also provides diagnostic reagents and methods for using such reagents for detecting the existence of an infection in a human, with bacteria of a *Neisseria* species. In preferred embodiments, such diagnostic reagents comprise antibodies that are immunologically reactive with a bacterial hemoglobin receptor protein. In a preferred embodiment, such antibodies are raised against a bacterial hemoglobin receptor protein isolated from bacteria of *Neisseria* species. In a particularly preferred embodiment, such antibodies are specific for the hemoglobin receptor protein isolated from *Neisseria meningitidis*, serotypes A, B or C. In additional particularly preferred embodiments, such antibodies are specific for the hemoglobin receptor protein isolated from *Neisseria gonorrhoeae*.

In yet another embodiment of this aspect of the invention are provided diagnostic reagents and methods for using such reagents wherein said reagents are nucleic acid hybridization probes comprising a bacterial hemoglobin receptor gene. In a preferred embodiment, the bacterial hemoglobin receptor protein gene is isolated from bacteria of *Neisseria* species. In a particularly preferred embodiment, the hemoglobin receptor protein gene is isolated from *Neisseria meningitidis*. In particular examples of this embodiment of the invention, the nucleic acid probes comprise a specifically-hybridizing fragment of a 3.3 kilobase (kb) BamHI/HindIII fragment of *N. meningitidis*, serotype C genomic DNA. In this embodiment, the nucleotide sequence comprises all or a specifically-hybridizing fragment of an open reading frame of 2376 nucleotides of *N. meningitidis*, serotype C genomic DNA encoding 792 amino acids comprising the hemoglobin receptor gene. In this embodiment of the invention, the nucleotide sequence of the *N. meningitidis*, serotype C hemoglobin receptor gene is the sequence depicted in FIGS. 2A–2H (SEQ ID No:1). In another example of this embodiment of the invention, the nucleic acid probes comprise a specifically-hybridizing fragment of a 2373 bp, polymerase chain reaction-amplified fragment of *N. meningitidis*, serotype A genomic DNA. In this embodiment, the nucleotide sequence comprises all or a specifically-hybridizing fragment of an open reading frame of 2370 nucleotides of *N. meningitidis*, serotype A genomic DNA encoding 790 amino acids comprising the hemoglobin receptor gene. In this embodiment of the invention, the nucleotide sequence of the *N. meningitidis*, serotype A hemoglobin receptor gene is the sequence depicted in FIGS. 7A–7I (SEQ ID No:3). In yet another example of this embodiment of the invention, the nucleic acid probes comprise a specifically-hybridizing fragment of a 2376 bp, polymerase chain reaction-amplified fragment of *N. meningitidis*, serotype B genomic DNA. In this embodiment, the nucleotide sequence comprises all or a specifically-hybridizing fragment of an open reading frame of 2373 nucleotides of *N. meningitidis*, serotype B genomic DNA encoding 791 amino acids comprising the hemoglobin receptor gene. In this embodiment of the invention, the nucleotide sequence of the *N. meningitidis*, serotype B hemoglobin receptor gene is the sequence depicted in FIGS. 8A–8I (SEQ ID No:5). The invention also provides nucleic acid hybridization probes comprising a bacterial hemoglobin receptor gene isolated from *N. gonorrhoeae*. In a preferred embodiment of this aspect of the invention, the nucleic acid probes comprise a specifically-hybridizing fragment of a 2378 bp, polymerase chain reaction-amplified fragment of *N. gonorrhoeae* genomic DNA. In this embodiment, the nucleotide sequence comprises all or a specifically-hybridizing fragment of an open reading frame of 2373 nucleotides of *N. gonorrhoeae* genomic DNA encoding 791 amino acids comprising the hemoglobin receptor gene. In this embodiment of the invention, the nucleotide sequence of the *N. gonorrhoeae* hemoglobin receptor gene is the sequence depicted in FIGS. 9A–9I (SEQ ID No:7). It will be understood that the term "specifically-hybridizing" when used to describe a fragment of a nucleic acid encoding a bacterial hemoglobin receptor gene is intended to mean that nucleic acid hybridization of such a fragment is stable under high stringency conditions of hybridization and washing as the term "high stringency" would be understood by those having skill in the molecular biological arts.

Also provided by the invention are therapeutic agents and methods for using such agents for treating the an infection in a human with bacteria of a *Neisseria* species. In preferred embodiments, such agents comprise antibodies that are immunologically reactive with a bacterial hemoglobin receptor protein. In a preferred embodiment, such antibodies are raised against a bacterial hemoglobin receptor protein isolated from bacteria of *Neisseria* species. In a particularly preferred embodiment, such antibodies are specific for the hemoglobin receptor protein isolated from *Neisseria meningitidis*, serotypes A, B or C. In additional preferred embodiments, such antibodies are specific for the hemoglobin receptor protein isolated from *Neisseria gonorrhoeae*. Therapeutic agents provided in this aspect of the invention comprise such antibodies in a pharmaceutically-acceptable carrier, along with appropriate adjuvants and the like. In additional embodiments, such antibodies are covalently conjugated to a bactericidal or bacteriostatic agent effective against bacteria of *Neisseria* species, preferably *N. meningitidis* and *N. gonorrhoeae*.

In yet another embodiment of this aspect of the invention are provided therapeutic reagents and methods for using such reagents wherein said reagents comprise recombinant expression constructs of the invention, or a homologue thereof that expresses the nucleic acid encoding a hemoglobin receptor in an antisense orientation. In a preferred embodiment, the bacterial hemoglobin receptor protein gene is isolated from bacteria of *Neisseria* species. In a particularly preferred embodiment, the hemoglobin receptor protein gene is isolated from *Neisseria meningitidis*. In particular examples of this embodiment of the invention, the nucleic acids comprise a specifically-hybridizing fragment of a 3.3 kilobase (kb) BamHI/HindIII fragment of *N. meningitidis*, serotype C genomic DNA. In this embodiment, the nucleotide sequence comprises all or a specifically-hybridizing fragment of an open reading frame of 2376 nucleotides of *N. meningitidis*, serotype C genomic DNA encoding 792 amino acids comprising the hemoglobin receptor gene. In this embodiment of the invention, the nucleotide sequence of the *N. meningitidis*, serotype C hemoglobin receptor gene is the sequence depicted in FIGS. 2A–2H (SEQ ID No:1). In another example of this embodiment of the invention, the nucleic acid probes comprise a specifically-hybridizing fragment of a 2373 bp, polymerase chain reaction-amplified fragment of *N. meningitidis*, serotype A genomic DNA. In this embodiment, the nucleotide sequence comprises all or a specifically-hybridizing fragment of an open reading frame of 2370 nucleotides of *N. meningitidis*, serotype A genomic DNA encoding 790 amino acids comprising the hemoglobin receptor gene. In this embodiment of the invention, the nucleotide sequence of the *N. meningitidis*, serotype A hemoglobin receptor gene is the sequence depicted in FIGS. 7A–7I (SEQ ID No:3). In yet another example of this embodiment of the invention, the nucleic acid probes comprise a specifically-hybridizing fragment of a 2376 bp, polymerase chain reaction-amplified fragment of *N. meningitidis*, serotype B genomic DNA. In this embodiment, the nucleotide sequence comprises all or a specifically-hybridizing fragment of an open reading frame of 2373 nucleotides of *N. meningitidis*, serotype B genomic DNA encoding 791 amino acids comprising the hemoglobin receptor gene. In this embodiment of the invention, the nucleotide sequence of the *N. meningitidis*, serotype B hemoglobin receptor gene is the sequence depicted in FIGS. 8A–8I (SEQ ID No:5). The invention also provides recombinant expression constructs of the invention, or a homologue thereof that expresses the nucleic acid encoding a hemoglobin receptor in an antisense orientation, wherein the nucleic acid encodes a bacterial hemoglobin receptor gene isolated from *N. gonorrhoeae*. In a preferred embodiment of this aspect of the invention, the nucleic acid probes comprise a specifically-hybridizing fragment of a 2378 bp, polymerase chain reaction-amplified fragment of *N. gonorrhoeae* genomic DNA. In this embodiment, the nucleotide sequence comprises all or a specifically-hybridizing fragment of an open reading frame of 2373 nucleotides of *N. gonorrhoeae* genomic DNA encoding 791 amino acids comprising the hemoglobin receptor gene. In this embodiment of the invention, the nucleotide sequence of the *N. gonorrhoeae* hemoglobin receptor gene is the sequence depicted in FIGS. 9A–9I (SEQ ID No:7).

The invention also provides a method for screening compounds for their ability to inhibit, facilitate or modulate the biochemical activity of a bacterial hemoglobin receptor protein of the invention, for use in the in vitro screening of novel agonist and antagonist compounds and novel bactericidal and bacteriostatic agents specific for the hemoglobin receptor protein. In preferred embodiments, cells transformed with a recombinant expression construct of the invention are contacted with such a compound, and the binding capacity of the compounds, as well as the effect of the compound on binding of other, known hemoglobin receptor agonists, such as hemoglobin and hemin, and antagonists, is assayed. Additional preferred embodiments comprise quantitative analyses of such effects.

The present invention is also useful for the detection of bactericidal and/or bacteriostatic analogues, agonists or antagonists, recognized or unrecognized, of a bacterial hemoglobin receptor protein, preferably derived from bacteria of *Neisseria* species, most preferably isolated from *N. meningitidis*, wherein such compounds are either naturally occurring or embodied as a drug.

The invention also provides vaccines for immunizing a human against infection with pathogenic bacteria of *Neisseria* species, the vaccines comprising the hemoglobin binding proteins of the invention or antigenic fragments thereof. In a preferred embodiment, the vaccines of the invention comprise cells expressing a hemoglobin receptor binding protein of the invention, or an antigenic fragment thereof, preferably wherein said cells are attenuated varieties of cells adapted for growth in humans, i.e., wherein such cells are non-pathogenic and do not cause bactermia, endotoxemia or sepsis. Examples of such attenuated varieties of cells include attenuated strains of *Salmonella* species, for example *Salmonella typhi* and *Salmonella typhimurium*, as well as other attenuated bacterial species. Also provided by the invention are recombinant expression constructs as disclosed herein useful per se as vaccines, for introduction into an animal and production of an immunologic response to bacterial hemoglobin receptor protein antigens encoded therein.

Specific preferred embodiments of the present invention will become evident from the following more detailed description of certain preferred embodiments and the claims.

DESCRIPTION OF THE DRAWINGS

The foregoing and other objects of the present invention, the various features thereof, as well as the invention itself may be more fully understood from the following description, when read together with the accompanying drawings in which:

FIG. 1 is a schematic drawing of the restriction enzyme digestion map of a *N. meningitidis* cosmid clone and subclones thereof derived as described in Example 2.

FIGS. 2A–2H illustrates the nucleotide (SEQ ID No.:1) and deduced amino acid (SEQ ID No.:2) sequences of the *N. meningitidis* hemoglobin receptor protein encoded in a 3.3 kb BamHI/HindIII DNA fragment.

FIG. 3 presents a photograph of a stained SDS/ 10% PAGE electrophoresis gel showing the results of in vitro expression of the *N. meningitidis* hemoglobin receptor gene product as an approximately 90 kilodalton protein, and β-lactamase protein having a molecular weight of about 30.0 kilodaltons used as a molecular weight marker.

FIGS. 4A–4C presents an amino acid sequence comparison between portions of the *N. meningitidis* transferrin receptor Tbp1 (SEQ ID No.:9), the *N. meningitidis* lactoferrin receptor LbpA (SEQ ID No.:10), and *N. meningitidis* hemoglobin receptor HmbR (SEQ ID No.:2).

FIG. 5 illustrates Southern hybridization analysis of chromosomal DNA from *N. meningitidis* 8013 and the MC8013hmbR mutant using a BamHI-SalI fragment of the hmb gene as probe labeled using a DIG nonradioactive DNA labelling and detection kit (Boehringer Mannheim Biochemicals, Indianapolis, Ind.). Lane 1 contains DNA from *N. meningitidis* strain MC8013, digested with ClaI; lane 2 is MC8031hmbR DNA digested with ClaI; lane 3, is MC8013 DNA digested with BamHI and SalI; and lane 4 is MC8013hmbR DNA digested with BamHI and SalI.

FIG. 6 is a graph describing the course of infection using *N. meningitidis* wild type (MC8013) and hmbR mutant strains in an in vivo rat infant infection model. Each strain was injected intraperitoneally ($2\times10^6$ CFU) into three infant inbred Lewis rats. The results represent the average of two similarly-performed experiments.

FIGS. 7A–7I illustrates the nucleotide (SEQ ID No.:3) and deduced amino acid (SEQ ID No.:4) sequences of the *N. meningitidis*, serotype A hemoglobin receptor protein encoded on a 2373 bp polymerase chain reaction-amplified DNA fragment.

FIGS. 8A–8I illustrates the nucleotide (SEQ ID No.:5) and deduced amino acid (SEQ ID No.:6) sequences of the *N. meningitidis*, serotype B hemoglobin receptor protein encoded on a 2376 bp polymerase chain reaction-amplified DNA fragment.

FIGS. 9A–9I illustrates the nucleotide (SEQ ID No.:7) and deduced amino acid (SEQ ID No.:8) sequences of the *N. gonorrhoeae* hemoglobin receptor protein encoded on a 2376 bp polymerase chain reaction-amplified DNA fragment.

FIG. 10 represents a schematic of a nucleic acid sequence comparison between the hemoglobin receptor proteins derived from *N. meningitidis*, serotypes A (SEQ ID No.:3), B (SEQ ID No.:5) and C (SEQ ID No.:1) and from *N. gonorrhoeae* (SEQ ID No.:7), wherein the direction of trascription of the genes is in the direction of the arrow, and the following abbreviations refer to restriction endonuclease sites: H represents HindIII; N represents NotI; Bg represents BglI; Bs represents BssHI; Nr represents NruI; Cl represents ClaI; P represents PstI; Sa represents SacI; Av represents AvaI; B represents BamHI; S represents SalI; EV represents EcoRV; Sh represents SphI; and Sy represents StyI.

FIGS. 11A–11D presents an amino acid sequence comparison between the hemoglobin receptor proteins derived from *N. meningitidis*, serotypes A (SEQ ID No.:4), B (SEQ ID No.:6) and C (SEQ ID No.:2) and from *N. gonorrhoeae* (SEQ ID No.:8).

DETAILED DESCRIPTION OF THE PREFERRED EMBODIMENTS

The term "bacterial hemoglobin receptor" as used herein refers to bacterial proteins comprising the outer membrane of Gram negative bacteria, which specifically mediate transit of hemoglobin-derived hemin, as well as hemin from other sources, through the outer membrane of such bacteria and into the periplasmic space. The bacterial hemoglobin receptor proteins of the invention are characterized by first, an amino acid sequence that is essentially the sequence depicted in FIGS. 2A–2H (SEQ ID No.:2), FIGS. 7A–7I (SEQ ID No.:4), FIGS. 8A–8I (SEQ ID No.:6) and FIGS. 9A–9I (SEQ ID No.:8). The bacterial hemoglobin receptor proteins of the invention are further characterized by having substantially the same biological activity as a protein having the amino acid sequence depicted in FIGS. 2A–2H (SEQ ID No.:2), FIGS. 7A–7I (SEQ ID No.:4), FIGS. 8A–8I (SEQ ID No.:6) and FIGS. 9A–9I (SEQ ID No.:8). This definition is intended to encompass naturally-occurring variants and mutant proteins, as well as genetically engineered variants made by man.

Cloned, isolated and purified nucleic acid provided by the present invention may encode a bacterial hemoglobin receptor protein of any *Neisseria* species of origin, including, most preferably, *Neisseria meningitidis* species and serotypes thereof and *Neisseria gonorhoeae* species.

The nucleic acid hybridization probes provided by the invention comprise DNA or RNA having all or a specifically-hybridizing fragment of the nucleotide sequence of the hemoglobin receptor protein as depicted in FIGS. 2A–2H (SEQ ID No.:1), FIGS. 7A–7I (SEQ ID No.:3), FIGS. 8A–8I (SEQ ID No.:5) and FIGS. 9A–9I (SEQ ID No.:7), or any portion thereof effective in nucleic acid hybridization. Mixtures of such nucleic acid hybridization probes are also within the scope of this embodiment of the invention. Nucleic acid probes as provided herein are useful for detecting the presence of a bacteria, inter alia, in a human as the result of an infection, in contaminated biological samples and specimens, in foodstuffs and water supplies, or in any substance that may come in to contact with the human. Specific hybridization will be understood to mean that the nucleic acid probes of the invention are capable of forming stable, specific hybridization to bacterially-derived DNA or RNA under conditions of high stringency, as the term "high stringency" would be understood by those with skill in the art (see, for example, Sambrook et al., 1989, *Molecular Cloning: A Laboratory Manual*, Cold Spring Harbor Laboratory Press, Cold Spring Harbor, N.Y. and Hames and Higgins, eds., 1985, *Nucleic Acid Hybridization*, IRL Press, Oxford, U.K.). Hybridization will be understood to be accomplished using well-established techniques, including but not limited to Southern blot hybridization, Northern blot hybridization, in situ hybridization and Southern hybridization to polymerase chain reaction product DNAs. The invention will thus be understood to provide oligonucleotides, specifically, pairs of oligonucleotides, for use as primers in support of in vitro amplification of bacterial hemoglobin receptor genes and mRNA transcripts.

The production of proteins such as bacterial hemoglobin receptor proteins from cloned genes by genetic engineering means is well known in this art. The discussion which follows is accordingly intended as an overview of this field, and is not intended to reflect the full state of the art. It will be understood from the following discussion that the hemoglobin receptor protein genes of this invention are particularly advantageous, since expression of such proteins by bacteria, including non-*Neisseria* species of bacteria, can complement certain auxotrophic mutants of said transformed bacteria otherwise unable to subsist absent supplementation of the growth media with iron (III).

DNA encoding a bacterial hemoglobin receptor protein, can be prepared in view of the instant disclosure, by chemical synthesis, by screening reverse transcripts of mRNA from appropriate cells, by screening genomic libraries from appropriate cells, or by combinations of these procedures, as illustrated below. Screening of mRNA or genomic DNA may be carried out with oligonucleotide probes generated from the nucleic acid sequence information from the bacterial hemoglobin receptor protein disclosed herein. Probes may be labeled with a detectable group such as a fluorescent group, a radioactive atom or a chemiluminescent group in accordance with know procedures and used in conventional hybridization assays, as described in greater detail in the Examples below. In the alternative, bacterial hemoglobin receptor protein-encoding nucleic acids may be obtained by use of the polymerase chain reaction (PCR) procedure, using appropriate pairs of PCR oligonucleotide primers corresponding to nucleic acid sequence information derived from a bacterial hemoglobin receptor protein as provided herein. See U.S. Pat. No. 4,683,195 to Mullis et al. and U.S. Pat. No. 4,683,202 to Mullis, as specifically disclosed herein in Example 9 below. In another alternative, such bacterial hemoglobin receptor protein-encoding nucleic acids may be isolated from auxotrophic cells transformed with a bacterial hemoglobin receptor protein gene, thereby relieved of the nutritional requirement for uncomplexed iron (III).

Any bacterial hemoglobin receptor protein of the invention may be synthesized in host cells transformed with a recombinant expression construct comprising a nucleic acid encoding the bacterial hemoglobin receptor protein. Such recombinant expression constructs can also be comprised of a vector that is a replicable DNA construct. Vectors are used herein either to amplify DNA encoding a bacterial hemoglobin receptor protein and/or to express DNA encoding a bacterial hemoglobin receptor protein. For the purposes of this invention, a recombinant expression construct is a replicable DNA construct in which a nucleic acid encoding a bacterial hemoglobin receptor protein is operably linked to suitable control sequences capable of effecting the expression of the bacterial hemoglobin receptor protein in a suitable host cell.

The need for such control sequences will vary depending upon the host cell selected and the transformation method chosen. Generally, bacterial control sequences include a transcriptional promoter, an optional operator sequence to control transcription, a sequence encoding suitable mRNA ribosomal binding sites (the Shine-Delgarno sequence), and sequences which control the termination of transcription and translation. Amplification vectors do not require expression control domains. All that is needed is the ability to replicate in a host, usually conferred by an origin of replication, and a selection gene to facilitate recognition of transformants. See, Sambrook et al., 1989, ibid.

Vectors useful for practicing the present invention include plasmids and virus-derived constructs, including phage and particularly bacteriophage, and integratable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. A preferred vector is pLAFR2 (see Riboli et al., 1991, *Microb. Pathogen.* 10: 393–403).

Transformed host cells are cells which have been transformed or transfected with recombinant expression constructs made using recombinant DNA techniques and comprising nucleic acid encoding a bacterial hemoglobin receptor protein. Preferred host cells are cells of *Neisseria* species, particularly *N. meningitidis*, as well as *Salmonella typhi* and *Salmonella typhimurium* species, and *Escherichia coli* auxotrophic mutant cells (hemA aroB). Transformed host cells may express the bacterial hemoglobin receptor protein, but host cells transformed for purposes of cloning or amplifying nucleic acid hybridization probe DNA need not express the receptor protein. When expressed, the bacterial hemoglobin receptor protein of the invention will typically be located in the host cell outer membrane. See, Sambrook et al., ibid.

Cultures of bacterial cells, particularly cells of *Neisseria* species, and certain *E. coli* mutants, are a desirable host for recombinant bacterial hemoglobin receptor protein synthesis. In principal, any bacterial cell auxotrophic for uncomplexed iron (III) is useful for selectively growing bacterial hemoglobin receptor protein-transformed cells. However, for this purpose, well-characterized auxotrophs, such as *E. coli* hemA aroB mutants are preferred.

The invention provides homogeneous compositions of a bacterial hemoglobin receptor protein produced by transformed cells as provided herein. Each such homogeneous composition is intended to be comprised of a bacterial hemoglobin receptor protein that comprises at least 90% of the protein in such a homogenous composition. The invention also provides membrane preparations from cells expressing a bacterial hemoglobin receptor protein as the result of transformation with a recombinant expression construct of the invention, as described herein.

Bacterial hemoglobin receptor proteins, peptide fragments thereof and membranes derived from cells expressing such proteins in accordance with the present invention may be used for the production of vaccines effective against bacterial infections in a human, with pathogenic microorganisms expressing such bacterial hemoglobin receptor proteins. Such vaccines preferably would be effective in raising an immunological response against bacteria of *Neisseria* species, most preferably *N. meningitidis* and *N. gonorhoeae*. Also encompassed within the vaccines provided by the invention are recombinant expression constructs as disclosed herein useful per se as vaccines, for introduction into an animal and production of an immunologic response to bacterial hemoglobin receptor protein antigens encoded therein.

Preparation of vaccines which contain polypeptide or polynucleotide sequences as active ingredients is well understood in the art. Typically, such vaccines are prepared as injectables, either as liquid solutions or suspensions. However, solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccine. The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1 to 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain 10% to 95% of active ingredient, preferably 25 to 70%.

The polypeptides of the invention may be formulated into the vaccine as neutral or salt forms. Pharmaceutically acceptable salts include the acid additional salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In another embodiment, such vaccines are provided wherein the bacterial hemoglobin receptor proteins or peptide fragments thereof are present in the intact cell membranes of cells expressing such proteins in accordance with the present invention. In preferred embodiments, cells useful in these embodiments include attenuated varieties of cells adapted to growth in humans. Most preferably, said cells are attenuated varieties of cells adapted for growth in humans, i.e., wherein such cells do not cause frank disease or other pathological conditions, such as bactermia, endotoxemia or sepsis. For the purposes of this invention, "attenuated" cells will be understood to encompass prokaryotic and eukaryotic cells that do not cause infection, disease, septicemia, endotoxic shock, pyrogenic shock, or other serious and adverse reactions to administration of vaccines to an animal, most preferably a human, when such cells are introduced into the animal, whether such cells are viable, living, heat-, chemically- or genetically attenuated or inactivated, or dead. It will be appreciated by those with skill in this art that certain minor side-effects of vaccination, such as short-term fever, muscle discomfort, general malaise, and other well-known reactions to vaccination using a variety of different types of vaccines, can be anticipated as accompanying vaccination of an animal, preferably a human, using the vaccines of the invention. Such acute, short-term and non-life-threatening side effects are encompassed in the instant definition of the vaccines of the invention, and vaccines causing such side-effects falls within the definition of "attenuated" presented herein. Preferred examples of such attenuated cells include attenuated varieties of *Salmonella* species, preferably *Salmonella typhi* and *Salmonella typhimurium*, as well as other attenuated bacterial species. It will be specifically understood that these embodiments of the vaccines of the invention encompass so-called "live" attenuated cell preparations as well as heat- or chemically-inactivated cell preparations.

In other embodiments of the invention are provided vaccines that are DNA vaccines, comprising the nucleic acids of the invention in recombinant expression constructs competant to direct expression of hemoglobin receptor proteins when introduced into an animal. In preferred embodiments, such DNA vaccines comprise recombinant expression constructs wherein the hemoglobin receptor-encoding nucleic acids of the invention are operably linked to promoter elements, most preferably the early gene promoter of cytomegalovirus or the early gene promoter of simian virus 40. DNA vaccines of the invention are preferably administered by intramuscular injection, but any appropriate route of administration, including oral, transdermal, rectal, nasal, aerosol administration into lung, or any other clinically-acceptable route of administration can be used by those with skill in the art.

In general, the vaccines of the invention are administered in a manner compatible with the dosage formulation, and in such amount as will be therapeutically effective and immunogenic. The quantity to be administered depends on the subject to be treated, capacity of the subject's immune system to synthesize antibodies, and the degree of protection desired. Precise amounts of active ingredient required to be administered depend on the judgment of the practitioner and are peculiar to each individual. However, suitable dosage ranges are of the order of several hundred micrograms active ingredient per individual. Suitable regimes for initial administration and booster shots are also variable, but are typified by an initial administration followed in one or two week intervals by a subsequent injection or other administration.

The recombinant expression constructs of the present invention are also useful in molecular biology to transform bacterial cells which do not ordinarily express a hemoglobin receptor protein to thereafter express this receptor. Such cells are useful, inter alia, as intermediates for making cell membrane preparations useful for receptor binding activity assays, vaccine production, and the like, and in certain embodiments may themselves be used, inter alia, as vaccines or components of vaccines, as described above. The recombinant expression constructs of the present invention thus provide a method for screening potentially useful bactericidal and bacteriostatic drugs at advantageously lower cost than conventional screening protocols. While not completely eliminating the need for ultimate in vivo activity and toxicology assays, the constructs and cultures of the invention provide an important first screening step for the vast number of potentially useful bactericidal and bacteriostatic drugs synthesized, discovered or extracted from natural sources each year. In addition, such bactericidal or bacteriostatic drugs would be selected to utilize a nutritional pathway associated with infectious virulence in these types of bacteria, as disclosed in more detail below, thus selectively targeting bacteria associated with the development of serious infections in vivo.

Also, the invention provides both functional bacterial hemoglobin receptor proteins, membranes comprising such proteins, cells expressing such proteins, and the amino acid sequences of such proteins. This invention thereby provides sufficient structural and functional activity information to enable rational drug design of novel therapeutically-active antibacterial drugs using currently-available techniques (see Walters, "Computer-Assisted Modeling of Drugs", in Klegerman & Groves, eds., 1993, *Pharmaceutical Biotechnology*, Interpharm Press: Buffalo Grove, Ill., pp. 165–174).

Nucleic acids and oligonucleotides of the present invention are useful as diagnostic tools for detecting the existence of a bacterial infection in a human, caused by a hemoglobin receptor protein-expressing pathological organism of *Neisseria* species. Such diagnostic reagents comprise nucleic acid hybridization probes of the invention and encompass paired oligonucleotide PCR primers, as described above. Methods provided by the invention include blot hybridization, in situ hybridization and in vitro amplification techniques for detecting the presence of pathogenic bacteria in a biological sample. Appropriate biological samples advantageously screened using the methods described herein include plasma, serum, lymph, cerebrospinal fluid, seminal fluid, mucosal tissue samples, biopsy samples, and other potential sites of bacterial infection. It is also envisioned that the methods of the invention may be used to screen water, foodstuffs, pharmaceuticals, and other potential sources of infection.

The invention also provides antibodies that are immunologically reactive to a bacterial hemoglobin receptor protein or epitopes thereof provided by the invention. The antibodies provided by the invention may be raised, using methods well known in the art, in animals by inoculation with cells that express a bacterial hemoglobin receptor protein or epitopes thereof, cell membranes from such cells, whether crude membrane preparations or membranes purified using methods well known in the art, or purified preparations of proteins, including fusion proteins, particularly fusion proteins comprising epitopes of a bacterial hemoglobin receptor protein of the invention fused to heterologous proteins and expressed using genetic engineering means in bacterial, yeast or eukaryotic cells, said proteins being isolated from such cells to varying degrees of homogeneity using conventional biochemical means. Synthetic peptides made using established synthetic means in vitro and optionally conjugated with heterologous sequences of amino acids, are also encompassed in these methods to produce the antibodies of the invention. Animals that are used for such inoculations include individuals from species comprising cows, sheep, pigs, mice, rats, rabbits, hamsters, goats and primates. Preferred animals for inoculation are rodents (including mice, rats, hamsters) and rabbits. The most preferred animal is the mouse.

Cells that can be used for such inoculations, or for any of the other means used in the invention, include any cell that naturally expresses a bacterial hemoglobin receptor protein as provided by the invention, or any cell or cell line that expresses a bacterial hemoglobin receptor protein of the invention, or any epitope thereof, as a result of molecular or genetic engineering, or that has been treated to increase the expression of an endogenous or heterologous bacterial hemoglobin receptor protein by physical, biochemical or genetic means. Preferred cells are *E. coli* auxotrophic mutant hemA aroB cells transformed with a recombinant expression construct of the invention and grown in media supplemented with hemin or hemoglobin as the sole iron (III) source, and cells of *Neisseria* species.

The present invention also provides monoclonal antibodies that are immunologically reactive with an epitope of a bacterial hemoglobin receptor protein of the invention, or fragment thereof, present on the surface of such cells, preferably *E. coli* cells. Such antibodies are made using methods and techniques well known to those of skill in the art. Monoclonal antibodies provided by the present invention are produced by hybridoma cell lines, that are also provided by the invention and that are made by methods well known in the art (see Harlow and Lane, 1988, *Antibodies: A Laboratory Manual*, Cold Spring Harbor Laboratory Press, Cold Spring Harbor, N.Y.).

Hybridoma cell lines are made by fusing individual cells of a myeloma cell line with spleen cells derived from animals immunized with a homogeneous preparation of a bacterial hemoglobin receptor protein, membranes comprised thereof, cells expressing such protein, or epitopes of a bacterial hemoglobin receptor protein, used per se or comprising a heterologous or fusion protein construct, as described above. The myeloma cell lines used in the invention include lines derived from myelomas of mice, rats, hamsters, primates and humans. Preferred myloma cell lines are from mouse, and the most preferred mouse myloma cell line is P3X63-Ag8.653. Preferred animals from whom spleens are obtained after immunization are rats, mice and hamsters, preferably mice, most preferably Balb/c mice. Spleen cells and myloma cells are fused using a number of methods well known in the art, including but not limited to incubation with inactivated Sendai virus and incubation in the presence of polyethylene glycole (PEG). The most preferred method for cell fusion is incubation in the presence of a solution of 45% (w/v) PEG-1450. Monoclonal antibodies produced by hybridoma cell lines can be harvested from cell culture supernatant fluids from in vitro cell growth; alternatively, hybridoma cells can be injected subcutaneously and/or into the peritoneal cavity of an animal, most preferably a mouse, and the monoclonal antibodies obtained from blood and/or ascites fluid.

Monoclonal antibodies provided by the present invention are also produced by recombinant genetic methods well known to those of skill in the art, and the present invention encompasses antibodies made by such methods that are immunologically reactive with an epitope of a bacterial hemoglobin receptor protein of the invention. The present invention also encompasses fragments, including but not limited to F(ab) and F(ab)$'_2$ fragments, of such antibody. Fragments are produced by any number of methods, including but not limited to proteolytic cleavage, chemical synthesis or preparation of such fragments by means of genetic engineering technology. The present invention also encompasses single-chain antibodies that are immunologically reactive with an epitope of a bacterial hemoglobin receptor protein, made by methods known to those of skill in the art.

The antibodies and fragments used herein can be labeled preferably with radioactive labels, by a variety of techniques. For example, the biologically active molecules can be labeled with a radionucleotide via conjugation with the cyclic anhydride of diethylenetriamine penta-acetic acid (DPTA) or bromoacetyl aminobenzyl ethylamine diamine tetra-acidic acid (BABE). See Hnatowich et al. (1983, Science 220: 613–615) and Meares et al. (1984, Anal. Biochem. 142: 68–78, both references incorporated by reference) for further description of labeling techniques.

The present invention also encompasses an epitope of a bacterial hemoglobin receptor protein of the invention, comprised of sequences and/or a conformation of sequences present in the receptor molecule. This epitope may be naturally occurring, or may be the result of proteolytic cleavage of a receptor molecule and isolation of an epitope-containing peptide or may be obtained by synthesis of an epitope-containing peptide using methods well known to those skilled in the art. The present invention also encompasses epitope peptides produced as a result of genetic engineering technology and synthesized by genetically engineered prokaryotic or eukaryotic cells.

The invention also includes chimeric antibodies, comprised of light chain and heavy chain peptides immunologically reactive to a bacterial hemoglobin receptor protein-derived epitope. The chimeric antibodies embodied in the present invention include those that are derived from naturally occurring antibodies as well as chimeric antibodies made by means of genetic engineering technology well known to those of skill in the art.

Also provided by the present invention are diagnostic and therapeutic methods of detecting and treating an infection in a human, by pathogenic organisms expressing a bacterial hemoglobin receptor protein. Diagnostic reagents for use in such methods include the antibodies, most preferably monoclonal antibodies, of the invention. Such antibodies are used in conventional immunological techniques, including but not limited to enzyme-linked immunosorbent assay (ELISA), radioimmune assay (RIA), Western blot assay, immunological titration assays, immunological diffusion assays (such as the Ouchterlony assay), and others known to those of skill in the art. Also provided are epitopes derived from a bacterial hemoglobin receptor protein of the invention and immunologically cross-reactive to said antibodies, for use in any of the immunological techniques described herein.

Additional diagnostic assays include nucleic acid hybridization assays, using the nucleic acids of the invention or specifically-hybridizing fragments thereof, for sensitive detection of bacterial genomic DNA and/or mRNA. Such assays include various blot assays, such as Southern blots, Northern blots, dot blots, slot blots and the like, as well as in vitro amplification assays, such as the polymerase chain reaction assay (PCR), reverse transcriptase-polymerase chain reaction assay (RT-PCR), ligase chain reaction assay (LCR), and others known to those skilled in the art. Specific restriction endonuclease digestion of diagnostic fragments detected using any of the methods of the invention, analogous to restriction fragment linked polymorphism assays (RFLP) are also within the scope of this invention.

The invention also provides therapeutic methods and reagents for use in treating infections in a human, cause by a microorganism expressing a bacterial hemoglobin receptor protein of the invention, most preferably a bacteria of Neisseria species. Therapeutic reagents for use in such methods include the antibodies, most preferably monoclonal antibodies, of the invention, either per se or conjugated to bactericidal or bacteriostatic drugs or other antibiotic compounds effective against the infectious microorganism. In such embodiments, the antibodies of the invention comprise pharmaceutical compositions, additionally comprising appropriate pharmaceutically-acceptable carriers and adjuvants or other ancillary components where necessary. Suitable carriers are, for example, water, saline, dextrose, glycerol, ethanol, or the like and combinations thereof. In addition, if desired, the pharmaceutical formulation may contain minor amounts of auxiliary substances such as wetting or emulsifying agents, pH buffering agents, or other compounds which enhance the effectiveness of the antibody. In these embodiments, it will be understood that the therapeutic agents of the invention serve to target the infectious bacteria, either by immunologically "tagging" the bacteria with an antibody of the invention for recognition by cytotoxic cells of a human's immune system, or by specifically delivering an antimicrobial drug to the infectious microorganism via the bacterial hemoglobin receptor protein.

Additional therapeutic reagents include the nucleic acids of the invention or fragments thereof, specifically antisense embodiments of such nucleic acids. Such antisense nucleic acids may be used themselves or embodied in a recombinant expression construct specific for antisense expression, wherein said construct is genetically engineered to co-opt a portion of the genome of a bacterial virus, preferably a bacteriophage, infectious for the bacterial pathogen responsible for the infection. In these embodiments, introduction of the antisense nucleic acids of the invention into the bacterial cell inhibits, attentuates or abolishes expression of the bacterial hemoglobin receptor, thereby reducing the virulence of the bacterial infection and enabling more effective antibacterial interventions. In additional embodiments, bacteriophage are provided bearing "knockout" copies of a bacterial hemoglobin receptor gene, whereby the phage achieves genetic mutation of the endogenous hemoglobin receptor gene in the infectious bacteria via, for example, homologous recombination of the exogenous knockout copy of the bacterial hemoglobin receptor gene with the endogenous hemoglobin receptor gene in the infectious microorganism.

The Examples which follow are illustrative of specific embodiments of the invention, and various uses thereof. They set forth for explanatory purposes only, and are not to be taken as limiting the invention.

EXAMPLE 1

Plasmids, Bacteria, and Media

Plasmids and bacteria used herein are listed on Table 1. *E. coli* strains were routinely grown in Luria-Bertani (LB) broth supplemented with 5-aminolevulinic acid and 50 mg/L hemin chloride as necessary. *N. meningitidis* 8013 is a serogroup C clinical isolate (Nassif et al., 1993, *Mol. Microbiol.* 8: 719–725). The meningococci were routinely grown on GCB agar (Difco) supplemented as described by Kellogg et al. (1963, *J. Bacteriol* 85: 1274–1279), and incubated at 37° C. under a 5% $CO_2$ atmosphere. Transformation of meningococci was performed as described by Nassif et al. (1992, *Mol. Microbiol.* 6: 591–597). When necessary, the following antibiotics were used with *E. coli*: rifampicin, 100 mg/L; tetracycline, 15 mg/L; kanamycin, 30 mg/L; chloramphenicol, 20 mg/L; carbenicillin, 100 mg/L. For *Neisseriae*, kanamycin at 100 mg/L was used when needed.

EXAMPLE 2

Auxotroph Complementation Cloning of a Hemoglobin Receptor Gene from *Neisseria meningitidis*

In order to identify *N. meningitidis* outer membrane receptor(s) involved in the uptake of hemin and/or hemoglobin iron, an auxotroph complementation cloning strategy was used, similar to the approach previously taken to identify the *Y. enterocolitica* and *V. cholerae* hemin receptors (see Stojiljkovic and Hantke, 1992, *EMBO J.* 11: 4359–4367; Henderson and Payne, 1994, *J. Bacteriol.* 176: 3269–3277). This strategy is based on the fact that the outer membrane of Gram-negative bacteria is impermeable to hemin (McConville and Charles, 1979, *J. Microbiol.* 113: 165–168) and therefore *E. coli* porphyrin biosynthesis mutants cannot grow on exogenously supplied hemin. If provided with the *N. meningitidis* outer membrane hemin receptor gene, the *E. coli* porphyrin mutant would be able to use exogenously supplied hemin as its porphyrin source.

A cosmid bank of *N. meningitidis* 8013 clone 6 DNA was prepared using conventional cosmid cloning methodologies (Sambrook et al., 1989, ibid.). *N. meningitidis* bacterial DNA was partially digested by MboI, size fractionated on sucrose gradients and cloned into the BamHI site of the cosmid vector pLAFR2 (Riboli et al., 1991, *Microb. Pathogen.* 10: 393–403). This cosmid bank was mobilized into the *E. coli* hemA aroB Rif$^r$ recipient strain by triparental matings using a conjugal plasmid pRK2013::Tn9. The mating mixture was plated on selective plates containing hemin chloride (50 mg/L), 0.1 mM 2,2'-dypyridil and rifampicin (100 mg/L). Several clones growing on exogenously supplied hemin were isolated after an overnight incubation.

The hemin utilization phenotype of these transformants was tested by re-introduction of the cosmids into naive *E. coli* hemA aroB cells and by monitoring the growth on hemin-supplemented plates. The ability of *E. coli* strains to utilize heme or hemoglobin as the sole iron source was tested as previously described (Stojiljkovic and Hantke, 1992, ibid.). Cells were grown on LB agar supplemented with 50 μM deferoxamine mesylate (an iron chelating agent, obtained from Sigma Chemical Co., St. Louis, Mo.). Filter discs (¼ inches, Schleichner & Schuell, Inc., Keene, N.H.) impregnated with the test compounds (20 μL of 5 mg/ml stock solutions unless otherwise stated) were placed on these plates. After overnight growth at 37° C.

TABLE I

| STRAIN | GENOTYPE |
|---|---|
| *E. coli* K12 | |
| EB53 | hemA, aroB, rpoB |
| KP1041 | MC4100tonB::Km$^r$ |
| H1388 | exbB::Tn10 Δlac pro |
| TSM348 | endA, hsdR, pro, supF, pRK2013::Tn9 |
| IR754 | EB53, tonB::Km$^r$ |
| IR736 | EB53, exbB::Tn10 |
| DH5α | recA, gyrB |
| *N. meningitidis* | |
| ATCC 13077 | Serotype A |
| — | Serotype B* |
| MC8013 | clone 6, wild type |
| MChmbR | hmbR::aphA-3 |
| *N. gonorrhoeae* MS11A | |
| | PLASMIDS |
| pSUSK | pA15 replicon, chloramphenicol$^r$ |
| pHEM22 | pLAFR2, hemoglobin-utilizing cosmid |
| pHEM44 | pLAFR2, hemin-utilizing cosmid |
| pIRS508 | 6 kb ClaI, pSUSK |
| pIRS523 | 3 kb BamHI/SalI, pUC19 |
| pIRS525 | 1.2 kb aphA-3, in NotI site of pIRS523 |
| pIRS527 | 4 kb BamHI/ClaI, pBluescript |
| pIRS528 | 0.7 kb NotI/BamHI, pBluescript |
| pIRS692 | 3.3 kb BamHI/HindIII, SU(SK) |

*Laboratory collection with 5% $CO_2$, zones of growth around the discs were monitored. The iron-bound proteins tested in this assay (all obtained from Sigma Chemical Co.) were hemoglobin from human, baboon, bovine and mouse sources, bovine hemin, human lactoferrin (90% iron saturated), and human transferrin (90% iron saturated, obtained from Boehringer Mannheim Biochemicals, Indianapolis, Ind.). A total of six hemin utilization positive cosmids were obtained using this protocol. Results using such assays are shown in Table II.

EXAMPLE 3

Restriction Enzyme Digestion Mapping of Hemin Utilization Positive Cosmids

Cosmid DNA from six hemin-utilization positive cosmids obtained as described in Example 2 were digested with ClaI, and the resulting fragments were cloned into ClaI-digested pSU(SK) vector (obtained from Stratagene, LaJolla, Calif.). One subclone, containing a 6 kb ClaI fragment from cosmid cos22 (the resultant plasmid was designated pIRS508), was determined to allow utilization of hemin and hemoglobin by *E. coli* hemA aroB assayed as described in Example 2. Another such clone, containing an 11 kb ClaI fragment from cos44 was also determined to allow hemin utilization in these auxotrophic mutant cells. Restriction analysis and Southern hybridization indicated that the DNA fragments originating from cos22 and cos44 are unrelated.

The deduced restriction enzyme digestion map of cosmid clone pIRS508 is shown in FIG. 1. Plasmid pIRS508 enabled *E. coli* hemA aroB to use both hemin and bovine hemoglobin as iron sources although growth on hemoglobin was somewhat weaker than on hemin (Table II). Further subcloning localized the hemin/hemoglobin utilization locus to the BamHI/HindIII fragment of the insert. In addition to sequences encoding the hemoglobin receptor gene (designated hmbR), sequences for a *Neisseria* insertion element (IS1106) and a portion of a *Neisseria* small repetitive element (IR1) are also represented in the Figure.

TABLE II

| STRAIN | φ-TYPE | HEMIN IRON | PORPHYRIN | Hb IRON |
|---|---|---|---|---|
| *N. meningitidis* | | | | |
| MC8013 | wild type | +++ | N.T. | +++ |
| MChmbR | Hb$^R$ mutant | +++ | N.T. | – |
| *E. coli* | | | | |
| EB53 | iron utilization$^-$ | – | – | – |
| EB53 (pIRS508) | tonB$^+$, exbB$^+$, hmbR$^+$ | +++ | +++ | + |
| IR754 (pIRS508) | tonB$^-$, exbB$^+$, hmbR$^+$ | – | – | – |
| IR736 (pIRS508) | tonB$^+$, exbB$^-$, hmbR$^+$ | – | – | – |

N.T. - not tested. Use of hemin/hemoglobin as a porphyrin source was tested by scoring for growth of strains around hemin (5 mg/mL) or hemoglobin (for *E. coli*, 10 mg/mL; for *N. meningitidis*, 5 mg/mL) discs on LB plates. The use of the hemin/hemoglobin as an iron source was tested similarly except NBD plates supplemented with 50 µL of 5 g/L delta-aminolevulinic acid were used (GCB plates supplemented with the 50 µM Desferal in the case of *N. meningitidis*).
– indicates no growth;
+ less then 100 mm of growth zone around the disc:
+++ ±15 mm of growth zone around the disc.

EXAMPLE 4

Nucleotide Sequence Analysis of a Cosmid Clone Encoding a *Neisseria* Hemoglobin Receptor Gene The nucleotide sequence of the 3.3 kb BamHI-HindIII DNA fragment carrying the hmbR gene and its promoter region was determined using the dideoxy chain termination method using a Sequenase 2.0 kit (obtained from U.S. Biochemicals, Cleveland, Ohio) and analyzed using a Bio-Rad electrophoresis system, an AutoRead kit (obtained from Pharmacia, Uppsala, SE) and an ALF-370 automatic sequenator (Pharmacia, Uppsala, Sweden). Plasmid subclones for sequencing were produced by a nested deletion approach using Erase-a-Base kit (obtained from Promega Biotech, Madison, Wis.) using different restriction sites in the hmbR gene. The nucleotide and predicted amino acid sequences of the hmbR gene are shown in FIGS. 2A–2H.

An open reading frame (ORF) encoding the *N. meningitidis*, serotype C hemoglobin receptor protein begins at position 470 of the sequence and encodes a protein having an amino acid sequence of 792 amino acids, with a calculated molecular weight of 85.5 kDa. A Shine-Delgarno sequence (SD) is found at position 460. The HmbR receptor protein contains a signal peptidase I recognition sequence at residues 22 to 24 of the protein (underlined), consistent with the fact that it is an outer membrane protein.

A typical Fur binding nucleotide sequence (designated "Fur box") was found in the promoter region of the hmbR gene (FIGS. 2A–2H). Like hemin utilization in *Yersiniae* and *Vibrio*, hemin and hemoglobin utilization in *Neisseria* are known to be iron-inducible phenotypes (West and Sparling, 1985, *Infect. Immun.* 47: 388–394; Dyer et al., 1987, *Infect. Immun.* 55: 2171–2175). In Gram-negative bacteria, conditional expression of many iron utilization genes is regulated by the Fur repressor, which recognizes a 19 bp imperfect dyad repeat (Fur-box) in the promoter regions of Fur-repressed genes. Recently, a genetic screen (FURTA) for the identification of Fur-regulated genes from different Gram-negative bacteria was described (Stojiljkovic et al., 1994, *J. Mol. Biol.* 236: 531–545), and this assay was used to test whether hmbR expression was controlled in this way. Briefly, a plasmid carrying a Fur-box sequence is transformed into an *E. coli* strain (H1717) which possesses a Fur-regulated lac fusion in the chromosome. Expression of this Fur-regulated lac fusion is normally repressed. Introduction of a multicopy Fur-box sequence on the plasmid titrates the available Fur repressor thus allowing expression of the Fur-regulated lac fusion (this phenotype is termed FURTA positive). Using this screen, the smallest insert fragment from cosmid pIRS508 that produced a FURTA positive result was a 0.7 kb BamHI-NotI DNA fragment carried on plasmid pIRS528 (see FIG. 1). This result indicated that the 0.7 kb BamHI-NotI fragment carries a Fur-box and that gene expression from the hmbR promoter is controlled by a Fur-Type operon.

Figure 3:
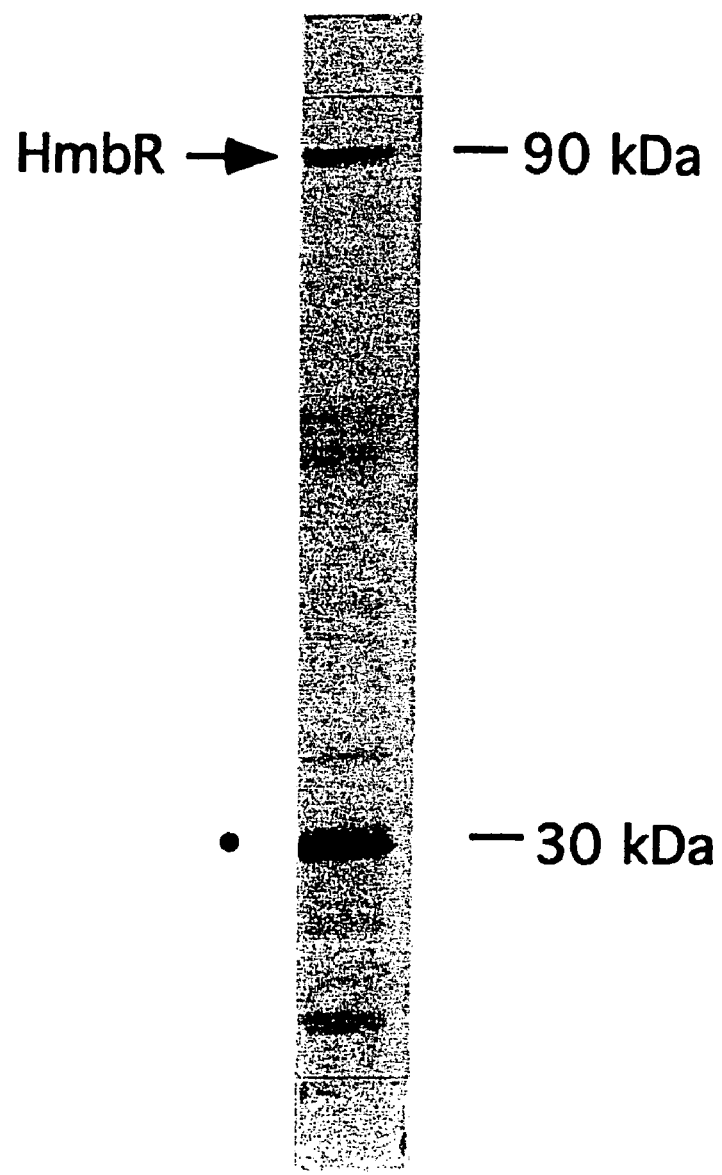

*N. meningitidis*, serotype C hemoglobin receptor protein was expressed in vitro using an *E. coli* S30 extract system from Promega Biotech (Madison, Wis.). The 3.3 kb BamHI-HindIII fragment, expressed in vitro, encoded a 90 kDa protein which corresponds in size to the predicted molecular weight of the unprocessed HmbR receptor. SDS/ 10% PAGE analysis showing the observed $M_r$ of 90K is shown in FIG. 3.

Immediately downstream of the hmbR gene (at positions 2955 to 3000 bp in FIGS. 2A–2H) was found a short nucleotide sequence that is 99% identical to the flanking sequence of the PIII gene of *N. gonorrhoeae* (Gotschlich et al., 1987, *J. Exp. Med.* 165: 471–482). The first 26 bp of this sequence represents one half of the inverted repeat (IR1) of the *N. gonorrhoeae* small repetitive element. This element is found in approximately 20 copies in both *N. gonorrhoeae* and *N. meningitidis* (Correia et al., 1988, *J. Biol. Chem.* 263: 12194–12198). The analysis of the nucleotide sequence from position 3027 to the ClaI (3984) restriction site (only the nucleotide sequence from BamHI (1) to HindIII (3370) is shown in FIGS. 2A–2H) indicated the presence of an IS1106 element (Knight et al., 1992, *Mol. Microbiol.* 6: 1565–1573). Interestingly, no nucleotide sequence similar to the IS1106 inverted repeat was found between the IR1 element and the beginning of the homology to IS1106.

These results were consistent with the cloning and identification of a novel hemoglobin receptor protein gene from *N. meningitidis*, embodied in a 3.3 kb BamHI/HindIII fragment of *N. meningitidis* genomic DNA.

EXAMPLE 5

Amino Acid Sequence Comparison of the *N. meningitidis* Hemoglobin Receptor Protein and *Neisseria* Lactoferrin and Transferrin Receptor Proteins A comparison of the transferrin (Tbp1; Legrain et al., 1993, *Gene* 130: 81–90), lactoferrin (LbpA; Pettersson et al., 1993, *Infect. Immun.* 61: 4724–4733, and 1994, *J. Bacteriol.* 176: 1764–1766) and hemoglobin receptors (HmbR) from *N. meningitidis* is shown in FIGS. 4A–4C. The comparison was done with the CLASTAL program from the PC/GENE program package (Intelligenetics, Palo Alto, Calif.). Only the amino-terminal and carboxyl terminal segments of the proteins are shown. An asterisk indicates identity and a point indicates similarity at the amino acid level. Lactoferrin and transferrin receptors were found to share 44.4% identity in amino acid sequence. In contrast, homology between these proteins and the hemoglobin receptor disclosed herein was found to be significantly weaker (22% amino acid sequence identity with lactoferrin and 21% with transferrin receptor).

EXAMPLE 6

TonB/ExbBD-Dependence of Hemin Transport by the *N. meningitidis* Hemoglobin Receptor It was known that the transport of iron-containing siderophores, some colicins and vitamin B12 across the outer membrane of *E. coli* depends on three cytoplasmic membrane proteins: TonB, ExbB and ExbD (Postle, 1990, *Mol. Microbiol.* 133: 891–898; Braun and Hantke, 1991, in Winkelmann, (ed.), *Handbook of Microbial Iron Chelates*, CRC Press, Boca Raton, Fla., pp. 107–138). In *Yersinia* and *Hemophilus*, hemin uptake was shown to be a TonB-dependent process (Stojiljkovic and Hantke, 1992, ibid.; Jarosik et al., 1994, *Infect, Immun.* 62: 2470–2477). Through direct interaction between the outer membrane receptors and the TonB cytoplasmic machinery, the substrate bound to the receptor is internalized into the periplasm (Heller et al., 1988, *Gene* 64: 147–153; Schoffler and Braun, 1989, *Molec. Gen. Genet.* 217: 378–383). This direct interaction has been associated with a particular amino acid sequence in membrane proteins associated with the TonB machinery.

All TonB-dependent receptors in Gram-negative bacteria contain several regions of high homology in their primary structures (Lundrigan and Kadner, 1986, *J. Biol. Chem.* 261: 10797–10801). In the amino acid sequence comparison described in Example 5, putative TonB-boxes of all three proteins are underlined. The carboxyl terminal end of the HmbR receptor contains the highly conserved terminal phenylalanine and position 782 arginine residues thought to be part of an outer membrane localization signal (Struyve et al., 1991, *J. Mol. Biol.* 218: 141–148; Koebnik, 1993, *Trends Microbiol.* 1: 201). At residue 6 of the mature HmbR protein, an amino acid sequence—ETTPVKA—is similar in sequence to the so called TonB-boxes of several Gram-negative receptors (Heller et al., 1988, ibid.). Interestingly, the putative TonB-box of HmbR has more homology to the TonB-box of the *N. gonorrhoeae* transferrin receptor (Cornelissen et al., 1992, *J. Bacteriol.* 174: 5788–5797) than to the TonB-boxes of *E. coli* siderophore receptors. When the sequence of the HmbR receptor was compared with other TonB-dependent receptors, the highest similarity was found with *Y. enterocolitica* HemR receptor although the similarity was not as high as to the *Neisseria* receptors.

In order to prove the TonB-dependent nature of the *N. meningitidis*, serotype C hemoglobin receptor, hmbR was introduced into exbB and tonB mutants of *E. coli* EB53, and the ability of the strains to utilize hemin and hemoglobin as porphyrin and iron sources was assessed. In these assays, both mutants of *E. coli* EB53 were unable to use hemin either as a porphyrin source or as an iron source in the presence of a functional hmbR (Table II). The usage of hemoglobin as an iron source was also affected (Table II). These results are consistent with the notion that the hmbR gene product, the *N. meningitidis* hemoglobin receptor protein of the invention, is TonB-dependent, since expression of this gene in TonB wild type *E. coli* supported the use of hemin and hemoglobin as sole iron source in the experiments disclosed in Example 2.

EXAMPLE 7

Functional Demonstration that the hmbR Gene Product is the Hemoglobin Receptor Protein in *N. meningitidis*

Figure 5:
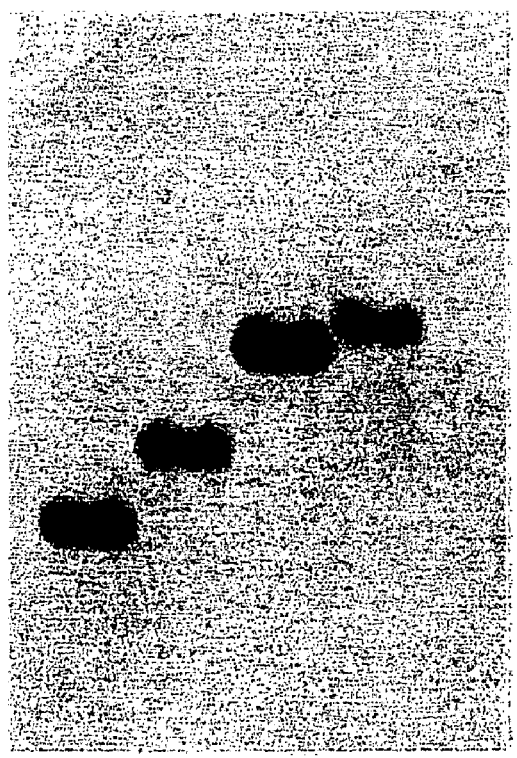

As shown in the data presented in Table II, hmbR mediated both hemin and hemoglobin utilization when expressed in *E. coli*, but hemoglobin utilization was less vigorous than hemin utilization. To determine if the HmbR receptor has the same specificity in *N. meningitidis*, hmbR was inactivated with a 1.2 kb kanamycin cassette (aphA-3; Nassif et al., 1991, ibid.) and transformed into wild-type *N. meningitidis* 8013 clone 6 (serotype C) cells. The inactivation of the chromosomal hmbR copy of the Km-resistant transformants was confirmed by Southern hybridization, as shown in FIG. 5. As can be seen from FIG. 5, wild-type *N. meningitidis* genomic DNA contains only one copy of the hmbR gene (lanes 1 and 3). In the Km$^r$ transformants, the size of the DNA fragments containing the wild-type gene has increased by 1.2 kb, which is the size of the Kan cassette (FIG. 5, lanes 2 and 4). When tested for its ability to utilize different iron-containing compounds, these mutant cells were found to be unable to use hemoglobin-bound iron, regardless of the source (human, bovine, baboon, mouse). The ability of the mutant to utilize hemoglobin-heptoglobin was not tested because the wild-type *N. meningitidis* strain is unable to use haptoglobin-haemoglobin complex as an iron source. However, the mutant was still able to use hemin iron, lactoferrin- and transferrin-bound iron as well as citrate-iron (Table II). As the iron-containing component of hemoglobin is hemin, a hemoglobin receptor would be expected to be capable of transporting hemin into the periplasm. Indeed, the cloning strategy disclosed herein depended on the ability of the cloned meningococcal receptor to transport hemin into the periplasm of *E. coli*. These results strongly suggest that *N. meningitidis* has at least two functional receptors that are involved in the internalization of hemin-containing compounds. One is the hemoglobin receptor described herein, which allows the utilization of both hemin and hemoglobin as iron sources. The other putative receptor in *N. meningitidis* is a hemin receptor which allows utilization of only hemin. This schema is also consistent with the isolation of several cosmid clones that allow *E. coli* EB53 to utilize hemin. DNAs from these cosmids do not hybridize with the hmbR probe, indicating that these clones encode a structurally-distinct receptor protein capable of transporting hemin into the periplasm of *N. meningitidis* cells.

EXAMPLE 8

Attenuation of Virulence in hmbR Mutant *N. meningitidis* Cells In Vivo

In order to test the importance of hemoglobin and hemin scavenging systems of *N. meningitidis* in vivo, the hmbR-mutant and the wild type strain of *N. meningitidis*, serotype C were inoculated into 5 day old infant rats and the numbers of bacteria recovered from blood and cerebrospinal fluid were followed. In these experiments, the method for the assessing *N. meningitidis*, serotype C virulence potential was essentially the same as described by Nassif et al. (1992, ibid.) using infant inbred Lewis rats (Charles River, Saint Aubin les Elbeufs, France). Inbred rats were used to minimize individual variations. Briefly, the 8013 strain was reactivated by 3 animal passages. After the third passage, bacteria were kept frozen in aliquots at −80° C. To avoid the possibility that modifications in the course of infection could result from selection of one spontaneous avirulent variant, one aliquot from the animal-passed frozen stock of 8013 was transformed with chromosomal DNA from the hmbR mutant, the resultant Kan$^r$ transformants were pooled without further purification and kept frozen at −80° C. For each experiment, all infant rats were from the same litter. $N.$ $meningitidis$ 8013 was grown overnight and 2×10$^6$ bacteria injected intraperitoneally into the infant rat. Three rats were used for each meningococcal strain. The course of infection was followed over a 24 hours time period with blood collected at the indicated times. At the 24 h time period, the rats were sacrificed, the cerebrospinal fluid (CSF) collected and the number of colony-forming units (CFU) determined. Each experiment was performed in replicate; similar results were obtained both times.

Figure 6:
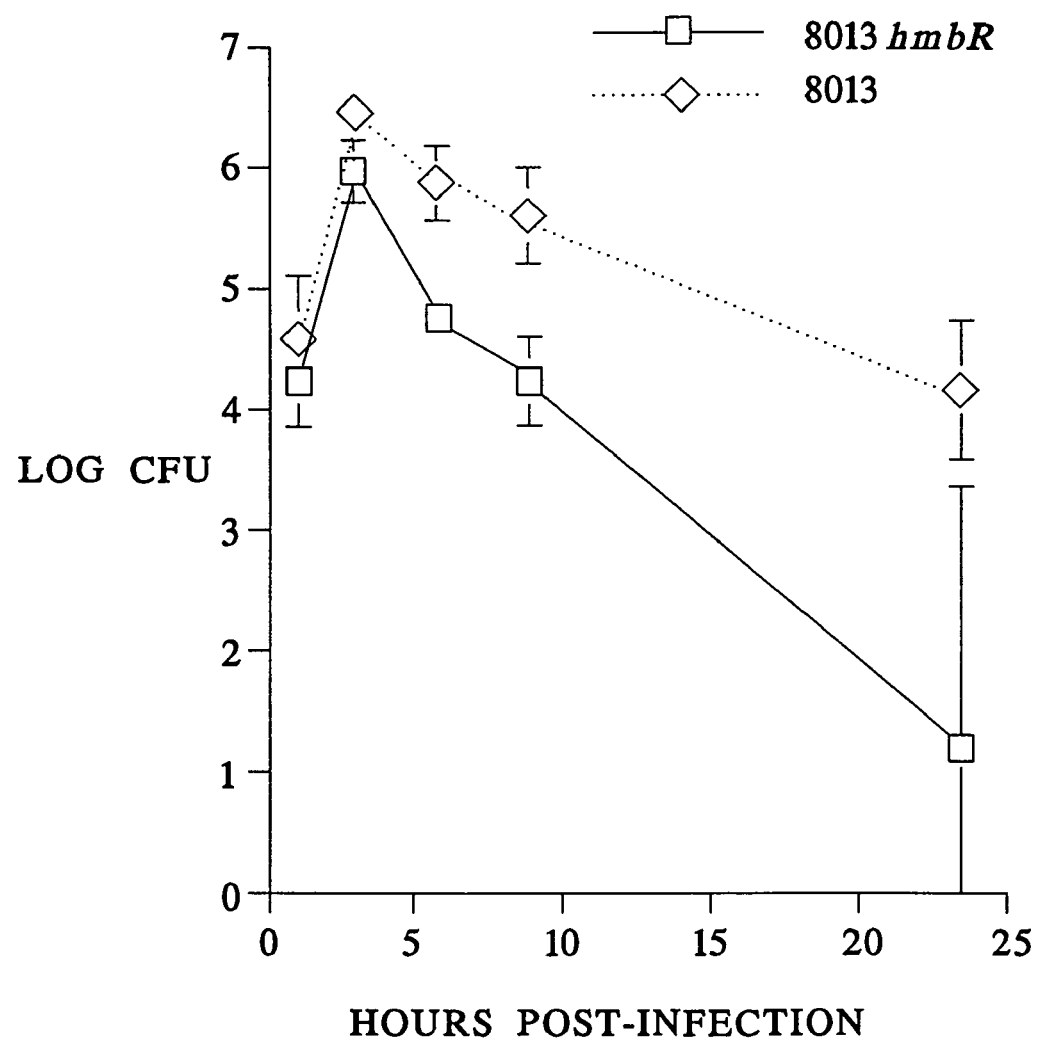

The results of these experiments are shown in FIG. 6. The hmbR$^−$ strain, which is unable to use hemoglobin as an iron source, was recovered from the blood of infected animals in significantly lower numbers when compared with the wild type strain. Both the mutant and the wild type strain were still able to cross the blood-brain barrier as indicated by the isolation of bacteria from the cerebrospinal fluid. These results indicate that hemoglobin represents an important iron source for $N.$ $meningitidis$ during growth in vivo.

EXAMPLE 9

Polymerase Chain Reaction Amplification of Hemoglobin Receptor Genes from $N.$ $meningitidis$ Serotypes and $N.$ $gonorrhoeae$ From the nucleotide sequence of the 3.3 kb BamHI-HindIII DNA fragment carrying the hmbR gene and its promoter region was determined specific oligonucleotide promers for in vitro amplification of the homologous hemoglobin receptor protein genes from $N.$ $meningitidis$ serotypes A and B and $N.$ $gonorrhoeae$ MS11A as follows.

The following oligonucleotide primers were developed for in vitro amplificaiton reactions using the polymerase chain reaction (PCR; Saiki et al., 1988, $Science$ 230: 1350–1354):

5'-AAACAGGTCTCGGCATAG-3' (sense primer) (SEQ ID No.:11)

5'-CGCGAATTCAAACAGGTCTCGGCATAG-3' (antisense primer) (SEQ ID No.:12) for amplifying the hemoglobin receptor protein from $N.$ $meningitidis$, serotype A;

5'-CGCGAATTCAAAAACTTCCATTCCAGCGATACG-3' (sense primer) (SEQ ID No.:13)

5'-TAAAACTTCCATTCCAGCGATACG-3' (antisense primer) (SEQ ID No.:14) for amplifying the hemoglobin receptor protein from $N.$ $meningitidis$, serotype B;

5'-AAACAGGTCTCGGCATAG-3' (sense primer) (SEQ ID No.:15)

or

5'-CGCGAATTCAAACAGGTCTCGGCATAG-3' (sense primer) (SEQ ID No.:16)

and

5' CGCGAATTCAAAAACTTCCATTCCAGCGATACG-3' (SEQ ID No.:17) (antisense primer)

or

5'-TAAAACTTCCATTCCAGCGATACG-3' (antisense primer) (SEQ ID No.:18) for amplifying the hemoglobin receptor protein from $N.$ $gonorrhoeae$ MS11A.

Genomic DNA from $N.$ $meningitidis$ serotype A or B or $N.$ $gonorrhoeae$ species was prepared using standard techniques (see Sambrook, et al., ibid.), including enzymatic degradation of bacterial cell walls, protoplast lysis, protease and RNase digestion, extraction with organic solvents such as phenol and/or chloroform, and ethanol precipitation. Crude DNA preparations were also used. An amount (typically, about 0.1 µg) of genomic DNA was used for each amplification reaction. A PCR amplification reaction consisted of Pfu polymerase (Stratagene, LaJolla, Calif.) and/or Taq polymerase (Boehringer Mannheim, Germany) in the appropriate buffer including about 20 picomoles of each amplificaiton primer and 200 nanomoles of each deoxynucleoside triphosphate. Amplification reactions were performed according to the following scheme:

| First cycle | 5 min at 95° C. |
| --- | --- |
| | 2 min at 51° C. |
| | 6 min at 72° C. |
| Cycles 2–13 | 45 sec at 95° C. |
| | 35 sec at 49° C. |
| | 10 min at 72° C. |
| Cycles 14–30 | 25 sec at 95° C. |
| | 35 sec at 47° C. |
| | 10 min at 72° C. |

Upon completion of the amplification reaction, DNA fragments were cloned either blunt-ended or, after EcoRI digestion, into EcoRI digested pSUKS or pWKS30 vectors and transformed into bacteria. Positively-selected clones were then analyzed for the presence of recombinant inserts, which were sequenced as described above in Example 4.

As a result of these experiments, three clones encoding the hemoglobin receptor genes from $N.$ $meningitidis$ serotypes A and B and $N.$ $gonorrhoeae$ MS11A were cloned and the sequence of these genes determined. The nucleic acid sequence for each of these genes are shown in FIGS. 7A–7I ($N.$ $meningitidis$, serotype A), FIGS. 8A–8I ($N.$ $meningitidis$, serotype A) and FIGS. 9A–9I ($N.$ $gonorrhoeae$ MS11A).

Figure 10:
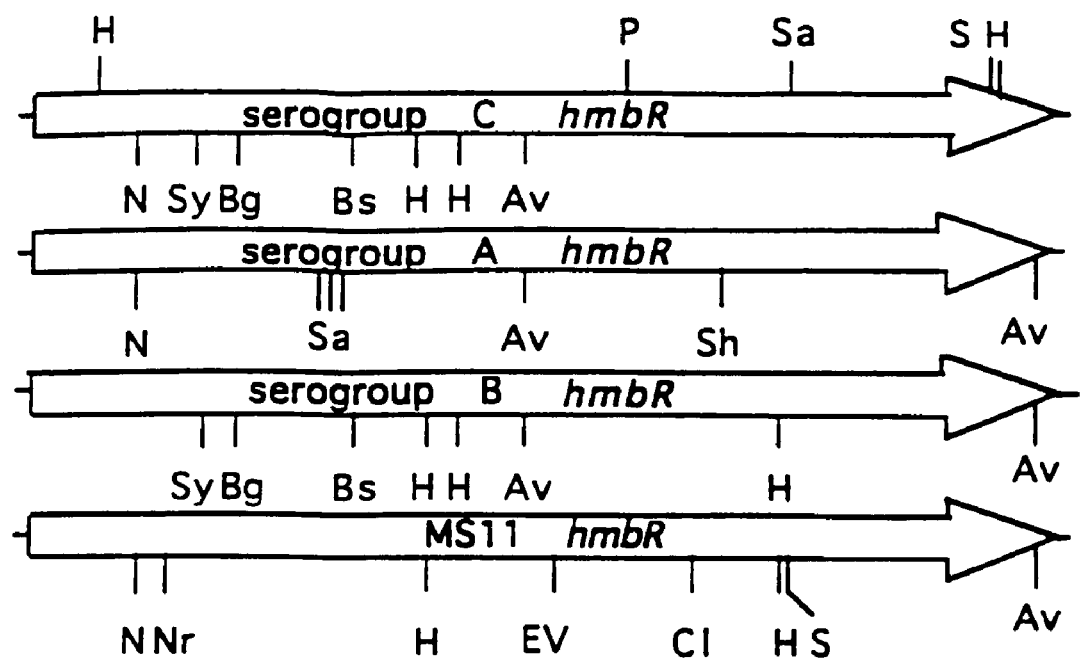

The degree of homology between the cloned hemoglobin receptors from the different $N.$ $meningitidis$ serotypes and $N.$ $gonorrhoeae$ MS11A was assessed by nucleic acid and amino acid sequence comparison, as described in Example 5 above. The results of these comparisons are shown in FIG. 10 and FIGS. 11A–11D, respectively. Hemoglobin receptor genes from the three $N.$ $meningitidis$ serotypes and $N.$ $gonorrhoeae$ MS11A were found to be from 86.5% to 93.4% homologous; the most homologous nucleic acids were $N.$ $meningitidis$ serotypes B and C, and the most divergent nucleic acids were $N.$ $meningitidis$ serotype B and $N.$ $gonorrhoeae$ MS11A (FIG. 10 and Table III). Homoglobin receptor proteins from all four $Neisseria$ species showed a high degree of homology to the other members of the group, ranging from 87% homology between the hemoglobin receptor proteins from *N. gonorrhoeae* MS11A and *N. meningitidis* serotype B to 93% homology between hemoglobin receptor proteins from *N. meningitidis* serotypes A and B (FIGS. 11A–11D). In this comparison, all four receptors were found to share 84.7% amino acid sequence identity, and up to 11.6% sequence similarity (i.e., chemically-related amino acid residues at homologous sites within the amino acid sequence). The non-conserved amino acids were found clustered in the regions of the amino acid sequence corresponding to the external loops in the predicted topographical structure of the hemoglobin receptor proteins.

TABLE III

|   | A | B | C | MS11 |
|---|---|---|---|------|
| A | X | 92.2% | 93.0% | 90.4% |
| B | 93.3% | X | 93.4% | 86.5% |
| C | 93.2% | 93% | X | 90.4% |
| MS11 | 91.1% | 86.8% | 91.4% | X |

*The numbers in the upper quadrant of the Table (in boldface) represent nucleic acid sequence homology between the different hemoglobin receptor genes of the invention, while the numbers in the lower quadrant of the Table represent amino acid sequence homology between the different hemoglobin receptor proteins It should be understood that the foregoing disclosure emphasizes certain specific embodiments of the invention and that all modifications or alternatives equivalent thereto are within the spirit and scope of the invention as set forth in the appended claims.

What is claimed is:

1. An isolated and purified recombinant nucleic acid encoding a hemoglobin receptor protein having an amino acid sequence that is the amino acid sequence depicted as Seq. I.D. No. 8.

2. A recombinant expression construct comprising a nucleic acid that encodes a hemoglobin receptor protein from a *Neisseria* species having an amino acid sequence that is the amino acid sequence depicted as Seq. I.D. No. 8.

3. A transformed cell culture comprising the recombinant expression construct of claim 2.

* * * * *

SEQUENCE LISTING

```
<160> NUMBER OF SEQ ID NOS: 13

<210> SEQ ID NO 1
<211> LENGTH: 2827
<212> TYPE: DNA
<213> ORGANISM: Infectious bursal disease virus
<220> FEATURE:
<221> NAME/KEY: CDS
<222> LOCATION: (112)..(2745)

<400> SEQUENCE: 1
ggatacgatg ggtctgaccc tctgggagtc acgaattaac gtggctacta ggggcgatac        60
ccgccgctgg ccgccacgtt agtggctcct cttcttgatg attctgccac c atg agt       117
                                                          Met Ser
                                                           1 gac att ttc aac agt cca cag gcg cga agc acg atc tca gca gcg ttc        165
Asp Ile Phe Asn Ser Pro Gln Ala Arg Ser Thr Ile Ser Ala Ala Phe
         5                  10                  15 ggc ata aag cct act gct gga caa gac gtg gaa gaa ctc ttg atc cct        213
Gly Ile Lys Pro Thr Ala Gly Gln Asp Val Glu Glu Leu Leu Ile Pro
     20                  25                  30 aaa gtt tgg gtg cca cct gag gat ccg ctt gcc agc cct agt cga ctg        261
Lys Val Trp Val Pro Pro Glu Asp Pro Leu Ala Ser Pro Ser Arg Leu
 35                  40                  45                  50 gca aag ttc ctc aga gag aac ggc tac aaa gtt ttg cag cca cgg tct        309
Ala Lys Phe Leu Arg Glu Asn Gly Tyr Lys Val Leu Gln Pro Arg Ser
                 55                  60                  65 ctg ccc gag aat gag gag tat gag acc gac caa ata ctc cca gac tta        357
Leu Pro Glu Asn Glu Glu Tyr Glu Thr Asp Gln Ile Leu Pro Asp Leu
             70                  75                  80 gca tgg atg cga cag ata gaa ggg gct gtt tta aaa ccc act cta tct        405
Ala Trp Met Arg Gln Ile Glu Gly Ala Val Leu Lys Pro Thr Leu Ser
         85                  90                  95 ctc cct att gga gat cag gag tac ttc cca aag tac tac cca aca cat        453
Leu Pro Ile Gly Asp Gln Glu Tyr Phe Pro Lys Tyr Tyr Pro Thr His
    100                 105                 110 cgc cct agc aag gag aag ccc aat gcg tac ccg cca gac atc gca cta        501
Arg Pro Ser Lys Glu Lys Pro Asn Ala Tyr Pro Pro Asp Ile Ala Leu
115                 120                 125                 130
```

```
ctc aag cag atg att tac ctg ttt ctc cag gtt cca gag gcc aac gag      549
Leu Lys Gln Met Ile Tyr Leu Phe Leu Gln Val Pro Glu Ala Asn Glu
            135                 140                 145 ggc cta aag gat gaa gta acc ctc ttg acc caa aac ata agg gac aag      597
Gly Leu Lys Asp Glu Val Thr Leu Leu Thr Gln Asn Ile Arg Asp Lys
        150                 155                 160 gcc tat gga agt ggg acc tac atg gga caa gca aat cga ctt gtg gcc      645
Ala Tyr Gly Ser Gly Thr Tyr Met Gly Gln Ala Asn Arg Leu Val Ala
    165                 170                 175 atg aag gag gtc gcc act gga aga aac cca aac aag gat cct cta aag      693
Met Lys Glu Val Ala Thr Gly Arg Asn Pro Asn Lys Asp Pro Leu Lys
180                 185                 190 ctt ggg tac act ttt gag agc atc gcg cag cta ctt gac atc aca cta      741
Leu Gly Tyr Thr Phe Glu Ser Ile Ala Gln Leu Leu Asp Ile Thr Leu
195                 200                 205                 210 ccg gta ggc cca ccc ggt gag gat gac aag ccc tgg gtg cca ctc aca      789
Pro Val Gly Pro Pro Gly Glu Asp Asp Lys Pro Trp Val Pro Leu Thr
                215                 220                 225 aga gtg ccg tca cgg atg ttg gtg ctg acg gga gac gta gat ggc gac      837
Arg Val Pro Ser Arg Met Leu Val Leu Thr Gly Asp Val Asp Gly Asp
            230                 235                 240 ttt gag gtt gaa gat tac ctt ccc aaa atc aac ctc aag tca tca agt      885
Phe Glu Val Glu Asp Tyr Leu Pro Lys Ile Asn Leu Lys Ser Ser Ser
        245                 250                 255 gga cta cca tat gta ggt cgc acc aaa gga gag aca att ggc gag atg      933
Gly Leu Pro Tyr Val Gly Arg Thr Lys Gly Glu Thr Ile Gly Glu Met
    260                 265                 270 ata gct atc tca aac cag ttt ctc aga gag cta tca aca ctg ttg aag      981
Ile Ala Ile Ser Asn Gln Phe Leu Arg Glu Leu Ser Thr Leu Leu Lys
275                 280                 285                 290 caa ggt gca ggg aca aag ggg tca aac aag aag aag cta ctc agc atg     1029
Gln Gly Ala Gly Thr Lys Gly Ser Asn Lys Lys Lys Leu Leu Ser Met
                295                 300                 305 tta agt gac tat tgg tac tta tca tgc ggg ctt ttg ttt cca aag gct     1077
Leu Ser Asp Tyr Trp Tyr Leu Ser Cys Gly Leu Leu Phe Pro Lys Ala
            310                 315                 320 gaa agg tac gac aaa agt aca tgg ctc acc aag acc cgg aac ata tgg     1125
Glu Arg Tyr Asp Lys Ser Thr Trp Leu Thr Lys Thr Arg Asn Ile Trp
        325                 330                 335 tca gct cca tcc cca aca cac ctc atg atc tct atg atc acc tgg ccc     1173
Ser Ala Pro Ser Pro Thr His Leu Met Ile Ser Met Ile Thr Trp Pro
    340                 345                 350 gtg atg tcc aac agc cca aat aac gtg ttg aac att gaa ggg tgt cca     1221
Val Met Ser Asn Ser Pro Asn Asn Val Leu Asn Ile Glu Gly Cys Pro
355                 360                 365                 370 tca ctc tac aaa ttc aac ccg ttc aga gga ggg ttg aac agg atc gtc     1269
Ser Leu Tyr Lys Phe Asn Pro Phe Arg Gly Gly Leu Asn Arg Ile Val
                375                 380                 385 gag tgg ata ttg gcc ccg gaa gaa ccc aag gct ctt gta tat gcg gac     1317
Glu Trp Ile Leu Ala Pro Glu Glu Pro Lys Ala Leu Val Tyr Ala Asp
            390                 395                 400 aac ata tac att gtc cac tca aac acg tgg tac tca att gac cta gag     1365
Asn Ile Tyr Ile Val His Ser Asn Thr Trp Tyr Ser Ile Asp Leu Glu
        405                 410                 415 aag ggt gag gca aac tgc act cgc caa cac atg caa gcc gca atg tac     1413
Lys Gly Glu Ala Asn Cys Thr Arg Gln His Met Gln Ala Ala Met Tyr
    420                 425                 430 tac ata ctc acc aga ggg tgg tca gac aac ggc gac cca atg ttc aat     1461
Tyr Ile Leu Thr Arg Gly Trp Ser Asp Asn Gly Asp Pro Met Phe Asn
435                 440                 445                 450
```

```
caa aca tgg gcc acc ttt gcc atg aac att gcc cct gct cta gtg gtg    1509
Gln Thr Trp Ala Thr Phe Ala Met Asn Ile Ala Pro Ala Leu Val Val
            455                 460                 465 gac tca tcg tgc ctg ata atg aac ctg caa att aag acc tat ggt caa    1557
Asp Ser Ser Cys Leu Ile Met Asn Leu Gln Ile Lys Thr Tyr Gly Gln
            470                 475                 480 ggc agc ggg aat gca gcc acg ttc atc aac aac cac ctc ttg agc aca    1605
Gly Ser Gly Asn Ala Ala Thr Phe Ile Asn Asn His Leu Leu Ser Thr
            485                 490                 495 cta gtg ctt gac cag tgg aac ctg atg aga cag ccc aga cca gac agc    1653
Leu Val Leu Asp Gln Trp Asn Leu Met Arg Gln Pro Arg Pro Asp Ser
500                 505                 510 gag gag ttc aaa tca att gag gac aag cta ggt atc aac ttt aag att    1701
Glu Glu Phe Lys Ser Ile Glu Asp Lys Leu Gly Ile Asn Phe Lys Ile
515                 520                 525                 530 gag agg tcc att gat gat atc agg ggc aag ctg aga cag ctt gtc ctc    1749
Glu Arg Ser Ile Asp Asp Ile Arg Gly Lys Leu Arg Gln Leu Val Leu
                535                 540                 545 ctt gca caa cca ggg tac ctg agt ggg ggg gtt gaa cca gaa caa tcc    1797
Leu Ala Gln Pro Gly Tyr Leu Ser Gly Gly Val Glu Pro Glu Gln Ser
                550                 555                 560 agc cca act gtt gag ctt gac cta cta ggg tgg tca gct aca tac agc    1845
Ser Pro Thr Val Glu Leu Asp Leu Leu Gly Trp Ser Ala Thr Tyr Ser
            565                 570                 575 aaa gat ctc ggg atc tat gtg ccg gtg ctt gac aag gaa cgc cta ttt    1893
Lys Asp Leu Gly Ile Tyr Val Pro Val Leu Asp Lys Glu Arg Leu Phe
            580                 585                 590 tgt tct gct gcg tat ccc aag gga gta gag aac aag agt ctc aag tcc    1941
Cys Ser Ala Ala Tyr Pro Lys Gly Val Glu Asn Lys Ser Leu Lys Ser
595                 600                 605                 610 aaa gtc ggg atc gag cag gca tac aag gta gtc agg tat gag gcg ttg    1989
Lys Val Gly Ile Glu Gln Ala Tyr Lys Val Val Arg Tyr Glu Ala Leu
                615                 620                 625 agg ttg gta ggt ggt tgg aac tac cca ctc ctg aac aaa gcc tgc aag    2037
Arg Leu Val Gly Gly Trp Asn Tyr Pro Leu Leu Asn Lys Ala Cys Lys
                630                 635                 640 aat aac gca ggc gcc gct cgg cgg cat ctg gag gcc aag ggg ttc cca    2085
Asn Asn Ala Gly Ala Ala Arg Arg His Leu Glu Ala Lys Gly Phe Pro
            645                 650                 655 ctc gac gag ttc cta gcc gag tgg tct gag ctg tca gag ttc ggt gag    2133
Leu Asp Glu Phe Leu Ala Glu Trp Ser Glu Leu Ser Glu Phe Gly Glu
            660                 665                 670 gcc ttc gaa ggc ttc aat atc aag ctg acc gta aca tct gag agc cta    2181
Ala Phe Glu Gly Phe Asn Ile Lys Leu Thr Val Thr Ser Glu Ser Leu
675                 680                 685                 690 gcc gaa ctg aac aag cca gta ccc ccc aag ccc cca aat gtc aac aga    2229
Ala Glu Leu Asn Lys Pro Val Pro Pro Lys Pro Pro Asn Val Asn Arg
                695                 700                 705 cca gtc aac act ggg gga ctc aag gca gtc agc aac gcc ctc aag acc    2277
Pro Val Asn Thr Gly Gly Leu Lys Ala Val Ser Asn Ala Leu Lys Thr
                710                 715                 720 ggt cgg tac agg aac gaa gcc gga ctg agt ggt ctc gtc ctt cta gcc    2325
Gly Arg Tyr Arg Asn Glu Ala Gly Leu Ser Gly Leu Val Leu Leu Ala
            725                 730                 735 aca gca aga agc cgt ctg caa gat gca gtt aag gcc aag gca gaa gcc    2373
Thr Ala Arg Ser Arg Leu Gln Asp Ala Val Lys Ala Lys Ala Glu Ala
            740                 745                 750 gag aaa ctc cac aag tcc aag cca gac gac ccc gat gca gac tgg ttc    2421
Glu Lys Leu His Lys Ser Lys Pro Asp Asp Pro Asp Ala Asp Trp Phe
755                 760                 765                 770
```

-continued

```
gaa aga tca gaa act ctg tca gac ctt ctg gag aaa gcc gac atc gcc    2469
Glu Arg Ser Glu Thr Leu Ser Asp Leu Leu Glu Lys Ala Asp Ile Ala
            775                 780                 785 agc aag gtc gcc cac tca gca ctc gtg gaa aca agc gac gcc ctt gaa    2517
Ser Lys Val Ala His Ser Ala Leu Val Glu Thr Ser Asp Ala Leu Glu
        790                 795                 800 gca gtt cag tcg act tcc gtg tac acc ccc aag tac cca gaa gtc aag    2565
Ala Val Gln Ser Thr Ser Val Tyr Thr Pro Lys Tyr Pro Glu Val Lys
    805                 810                 815 aac cca cag acc gcc tcc aac ccc gtt gtt ggg ctc cac ctg ccc gcc    2613
Asn Pro Gln Thr Ala Ser Asn Pro Val Val Gly Leu His Leu Pro Ala
820                 825                 830 aag aga gcc acc ggt gtc cag gcc gct ctt ctc gga gca gga acg agc    2661
Lys Arg Ala Thr Gly Val Gln Ala Ala Leu Leu Gly Ala Gly Thr Ser
835                 840                 845                 850 aga cca atg ggg atg gag gcc cca aca cgg tcc aag aac gcc gtg aaa    2709
Arg Pro Met Gly Met Glu Ala Pro Thr Arg Ser Lys Asn Ala Val Lys
                855                 860                 865 atg gcc aaa cgg cgg caa cgc caa aag gag agc cgc taacagccat         2755
Met Ala Lys Arg Arg Gln Arg Gln Lys Glu Ser Arg
                870                 875 gatgggaacc actcaagaag aggacactaa tcccagaccc cgtatccccg gccttcgcct   2815
gcgggggccc cc                                                      2827

<210> SEQ ID NO 2
<211> LENGTH: 878
<212> TYPE: PRT
<213> ORGANISM: Infectious bursal disease virus

<400> SEQUENCE: 2

Met Ser Asp Ile Phe Asn Ser Pro Gln Ala Arg Ser Thr Ile Ser Ala
1               5                   10                  15

Ala Phe Gly Ile Lys Pro Thr Ala Gly Gln Asp Val Glu Glu Leu Leu
            20                  25                  30

Ile Pro Lys Val Trp Val Pro Glu Asp Pro Leu Ala Ser Pro Ser
        35                  40                  45

Arg Leu Ala Lys Phe Leu Arg Glu Asn Gly Tyr Lys Val Leu Gln Pro
    50                  55                  60

Arg Ser Leu Pro Glu Asn Glu Glu Tyr Glu Thr Asp Gln Ile Leu Pro
65                  70                  75                  80

Asp Leu Ala Trp Met Arg Gln Ile Glu Gly Ala Val Leu Lys Pro Thr
                85                  90                  95

Leu Ser Leu Pro Ile Gly Asp Gln Glu Tyr Phe Pro Lys Tyr Tyr Pro
            100                 105                 110

Thr His Arg Pro Ser Lys Glu Lys Pro Asn Ala Tyr Pro Pro Asp Ile
        115                 120                 125

Ala Leu Leu Lys Gln Met Ile Tyr Leu Phe Leu Gln Val Pro Glu Ala
    130                 135                 140

Asn Glu Gly Leu Lys Asp Glu Val Thr Leu Leu Thr Gln Asn Ile Arg
145                 150                 155                 160

Asp Lys Ala Tyr Gly Ser Gly Thr Tyr Met Gly Gln Ala Asn Arg Leu
                165                 170                 175

Val Ala Met Lys Glu Val Ala Thr Gly Arg Asn Pro Asn Lys Asp Pro
            180                 185                 190

Leu Lys Leu Gly Tyr Thr Phe Glu Ser Ile Ala Gln Leu Leu Asp Ile
        195                 200                 205
```

```
                        -continued

Thr Leu Pro Val Gly Pro Pro Glu Asp Asp Lys Pro Trp Val Pro
    210                 215                 220

Leu Thr Arg Val Pro Ser Arg Met Leu Val Leu Thr Gly Asp Val Asp
225                 230                 235                 240

Gly Asp Phe Glu Val Glu Asp Tyr Leu Pro Lys Ile Asn Leu Lys Ser
                245                 250                 255

Ser Ser Gly Leu Pro Tyr Val Gly Arg Thr Lys Gly Glu Thr Ile Gly
            260                 265                 270

Glu Met Ile Ala Ile Ser Asn Gln Phe Leu Arg Glu Leu Ser Thr Leu
        275                 280                 285

Leu Lys Gln Gly Ala Gly Thr Lys Gly Ser Asn Lys Lys Leu Leu
    290                 295                 300

Ser Met Leu Ser Asp Tyr Trp Tyr Leu Ser Cys Gly Leu Leu Phe Pro
305                 310                 315                 320

Lys Ala Glu Arg Tyr Asp Lys Ser Thr Trp Leu Thr Lys Thr Arg Asn
                325                 330                 335

Ile Trp Ser Ala Pro Ser Pro Thr His Leu Met Ile Ser Met Ile Thr
            340                 345                 350

Trp Pro Val Met Ser Asn Ser Pro Asn Val Leu Asn Ile Glu Gly
        355                 360                 365

Cys Pro Ser Leu Tyr Lys Phe Asn Pro Phe Arg Gly Gly Leu Asn Arg
370                 375                 380

Ile Val Glu Trp Ile Leu Ala Pro Glu Pro Lys Ala Leu Val Tyr
385                 390                 395                 400

Ala Asp Asn Ile Tyr Ile Val His Ser Asn Thr Trp Tyr Ser Ile Asp
                405                 410                 415

Leu Glu Lys Gly Glu Ala Asn Cys Thr Arg Gln His Met Gln Ala Ala
            420                 425                 430

Met Tyr Tyr Ile Leu Thr Arg Gly Trp Ser Asp Asn Gly Asp Pro Met
        435                 440                 445

Phe Asn Gln Thr Trp Ala Thr Phe Ala Met Asn Ile Ala Pro Ala Leu
    450                 455                 460

Val Val Asp Ser Ser Cys Leu Ile Met Asn Leu Gln Ile Lys Thr Tyr
465                 470                 475                 480

Gly Gln Gly Ser Gly Asn Ala Ala Thr Phe Ile Asn Asn His Leu Leu
                485                 490                 495

Ser Thr Leu Val Leu Asp Gln Trp Asn Leu Met Arg Gln Pro Arg Pro
            500                 505                 510

Asp Ser Glu Glu Phe Lys Ser Ile Glu Asp Lys Leu Gly Ile Asn Phe
        515                 520                 525

Lys Ile Glu Arg Ser Ile Asp Asp Ile Arg Gly Lys Leu Arg Gln Leu
    530                 535                 540

Val Leu Leu Ala Gln Pro Gly Tyr Leu Ser Gly Val Glu Pro Glu
545                 550                 555                 560

Gln Ser Ser Pro Thr Val Glu Leu Asp Leu Leu Gly Trp Ser Ala Thr
                565                 570                 575

Tyr Ser Lys Asp Leu Gly Ile Tyr Val Pro Val Leu Asp Lys Glu Arg
            580                 585                 590

Leu Phe Cys Ser Ala Ala Tyr Pro Lys Gly Val Glu Asn Lys Ser Leu
        595                 600                 605

Lys Ser Lys Val Gly Ile Glu Gln Ala Tyr Lys Val Val Arg Tyr Glu
    610                 615                 620
```

-continued

```
Ala Leu Arg Leu Val Gly Gly Trp Asn Tyr Pro Leu Leu Asn Lys Ala
625                 630                 635                 640

Cys Lys Asn Asn Ala Gly Ala Ala Arg Arg His Leu Glu Ala Lys Gly
            645                 650                 655

Phe Pro Leu Asp Glu Phe Leu Ala Glu Trp Ser Glu Leu Ser Glu Phe
        660                 665                 670

Gly Glu Ala Phe Glu Gly Phe Asn Ile Lys Leu Thr Val Thr Ser Glu
    675                 680                 685

Ser Leu Ala Glu Leu Asn Lys Pro Val Pro Lys Pro Pro Asn Val
690                 695                 700

Asn Arg Pro Val Asn Thr Gly Gly Leu Lys Ala Val Ser Asn Ala Leu
705                 710                 715                 720

Lys Thr Gly Arg Tyr Arg Asn Glu Ala Gly Leu Ser Gly Leu Val Leu
                725                 730                 735

Leu Ala Thr Ala Arg Ser Arg Leu Gln Asp Ala Val Lys Ala Lys Ala
                740                 745                 750

Glu Ala Glu Lys Leu His Lys Ser Lys Pro Asp Asp Pro Asp Ala Asp
        755                 760                 765

Trp Phe Glu Arg Ser Glu Thr Leu Ser Asp Leu Leu Glu Lys Ala Asp
    770                 775                 780

Ile Ala Ser Lys Val Ala His Ser Ala Leu Val Glu Thr Ser Asp Ala
785                 790                 795                 800

Leu Glu Ala Val Gln Ser Thr Ser Val Tyr Thr Pro Lys Tyr Pro Glu
                805                 810                 815

Val Lys Asn Pro Gln Thr Ala Ser Asn Pro Val Val Gly Leu His Leu
                820                 825                 830

Pro Ala Lys Arg Ala Thr Gly Val Gln Ala Ala Leu Leu Gly Ala Gly
        835                 840                 845

Thr Ser Arg Pro Met Gly Met Glu Ala Pro Thr Arg Ser Lys Asn Ala
        850                 855                 860

Val Lys Met Ala Lys Arg Arg Gln Arg Gln Lys Glu Ser Arg
865                 870                 875

<210> SEQ ID NO 3
<211> LENGTH: 3261
<212> TYPE: DNA
<213> ORGANISM: Infectious bursal disease virus
<220> FEATURE:
<221> NAME/KEY: CDS
<222> LOCATION: (97)..(531)

<400> SEQUENCE: 3
ggatacgatc ggtctgaccc cgggggagtc acccgggac aggccgtcaa ggccttgttc    60
caggatggga ctcctccttc tacaacgcta tcattg atg gtt agt aga gat cag   114
                                        Met Val Ser Arg Asp Gln
                                        1               5 aca aac gat cgc agc gat gac aaa cct gca aga tca aac cca aca gat   162
Thr Asn Asp Arg Ser Asp Asp Lys Pro Ala Arg Ser Asn Pro Thr Asp
            10                  15                  20 tgt tcc gtt cat acg gag cct tct gat gcc aac aac cgg acc ggc gtc   210
Cys Ser Val His Thr Glu Pro Ser Asp Ala Asn Asn Arg Thr Gly Val
        25                  30                  35 cat tcc gga cga cac cct gga gaa gca cac tct cag gtc aga gac ctc   258
His Ser Gly Arg His Pro Gly Glu Ala His Ser Gln Val Arg Asp Leu
    40                  45                  50
```

-continued

| | | |
|---|---|---|
| gac cta caa ttt gac tgt ggg gga cac agg gtc agg gct aat tgt ctt<br>Asp Leu Gln Phe Asp Cys Gly Gly His Arg Val Arg Ala Asn Cys Leu<br>55                     60                         65                      70 | 306 |
| ttt ccc tgg att ccc tgg ctc aat tgt ggg tgc tca cta cac act gca<br>Phe Pro Trp Ile Pro Trp Leu Asn Cys Gly Cys Ser Leu His Thr Ala<br>                    75                         80                         85 | 354 |
| ggg caa tgg gaa cta caa gtt cga tca gat gct cct gac tgc cca gaa<br>Gly Gln Trp Glu Leu Gln Val Arg Ser Asp Ala Pro Asp Cys Pro Glu<br>                    90                         95                        100 | 402 |
| cct acc ggc cag tta caa cta ctg cag gct agt gag tcg gag tct cac<br>Pro Thr Gly Gln Leu Gln Leu Leu Gln Ala Ser Glu Ser Glu Ser His<br>           105                       110                        115 | 450 |
| agt gag gtc aag cac act tcc tgg tgg cgt tta tgc act aaa cgg cac<br>Ser Glu Val Lys His Thr Ser Trp Trp Arg Leu Cys Thr Lys Arg His<br>120                         125                         130 | 498 |
| cat aaa cgc cgt gac ctt cca agg aag cct gag tgaactgaca gatgttagct<br>His Lys Arg Arg Asp Leu Pro Arg Lys Pro Glu<br>135                     140                        145 | 551 |
| acaatgggtt gatgtctgca acagccaaca tcaacgacaa aattgggaac gtcctagtag | 611 |
| gggaaggggt caccgtcctc agcttaccca catcatatga tcttgggtat gtgaggcttg | 671 |
| gtgaccccat tcccgcaata gggcttgacc caaaaatggt agccacatgt gacagcagtg | 731 |
| acaggcccag agtctacacc ataactgcag ccgatgatta ccaattctca tcacagtacc | 791 |
| aaccaggtgg ggtaacaatc acactgttct cagccaacat tgatgccatc acaagcctca | 851 |
| gcgttggggg agagctcgtg tttcaaacaa gcgtccacgg ccttgtactg ggcgccacca | 911 |
| tctacctcat aggctttgat gggacaacgg taatcaccag ggctgtggcc gcaaacaatg | 971 |
| ggctgacgac cggcaccgac aaccttatgc cattcaatct tgtgattcca caaaacgaga | 1031 |
| taacccagcc aatcacatcc atcaaactgg agatagtgac ctccaaaagt ggtggtcagg | 1091 |
| caggggatca gatgtcatgg tcggcaagag ggagcctagc agtgacgatc catggtggca | 1151 |
| actatccagg ggccctccgt cccgtcacgc tagtggccta cgaaagagtg caacaggat | 1211 |
| ccgtcgttac ggtcgctggg gtgagcaact tcgagctgat cccaaatcct gaactagcaa | 1271 |
| agaacctggt tacagaatac ggccgatttg acccaggagc catgaactac acaaaattga | 1331 |
| tactgagtga gagggaccgt cttggcatca agaccgtctg gccaacaagg gagtacactg | 1391 |
| actttcgtga atacttcatg gaggtggccg acctcaactc tccctgaag attgcaggag | 1451 |
| cattcggctt caaagacata tccggcca taaggaggat agctgtgccg gtggtctcca | 1511 |
| cattgttccc acctgccgct cccctagccc atgcaattgg ggaaggtgta gactacctgc | 1571 |
| tgggcgatga ggcacaggct gcttcaggaa ctgctcgagc cgcgtcagga aaagcaagag | 1631 |
| ctgcctcagg ccgcataagg cagctgactc tcgccgccga caagggtac gaggtagtcg | 1691 |
| cgaatctatt ccaggtgccc cagaatcccg tagtcgacgg gattcttgct tcacctgggg | 1751 |
| tactccgcgg tgcacacaac ctcgactgcg tgttaagaga gggtgccacg ctattccctg | 1811 |
| tggttattac gacagtggaa gacgccatga cacccaaagc attgaacagc aaaatgtttg | 1871 |
| ctgtcattga aggcgtgcga gaagacctcc aacctccatc tcaaagagga tccttcatac | 1931 |
| gaactctctc tggacacaga gtctatggat atgctccaga tgggggtactt ccactggaga | 1991 |
| ctggagaga ctacaccgtt gtcccaatag atgatgtctg gacgacagc attatgctgt | 2051 |
| ccaaagatcc catacctcct attgtgggaa acagtggaaa tctagccata gcttacatgg | 2111 |
| atgtgtttcg acccaaagtc ccaatccatg tggctatgac gggagccctc aatgcttgtg | 2171 |
| gcgagattga gaaagtaagc tttagaagca ccaagctcgc cactgcacac cgacttggcc | 2231 |

```
ttaggttggc tggtcccgga gcattcgatg taaacaccgg gcccaactgg gcaacgttca    2291
tcaaacgttt ccctcacaat ccacgcgact gggacaggct cccctacctc aacctaccat    2351
accttccacc caatgcagga cgccagtacc accttgccat ggctgcatca gagttcaaag    2411 agaccccga actcgagagt gccgtcagag caatggaagc agcagccaac gtggacccac    2471
tattccaatc tgcactcagt gtgttcatgt ggctggaaga gaatgggatt gtgactgaca    2531
tggccaactt cgcactcagc gacccgaacg cccatcggat gcgaaatttt cttgcaaacg    2591
caccacaagc aggcagcaag tcgcaaaggg ccaagtacgg gacagcaggc tacggagtgg    2651
aggctcgggg ccccacacca gaggaagcac agagggaaaa agacacacgg atctcaaaga    2711
agatggagac catgggcatc tactttgcaa caccagaatg ggtagcactc aatgggcacc    2771
gagggccaag cccggccag ctaaagtact ggcagaacac acgagaaata ccggacccaa    2831
acgaggacta tctagactac gtgcatgcag agaagagccg gttggcatca aagaacaaa    2891 tcctaagggc agctacgtcg atctacgggg ctccaggaca ggcagagcca ccccaagctt    2951
tcatagacga agttgccaaa gtctatgaaa tcaaccatgg acgtggccca aaccaagaac    3011
agatgaaaga tctgctcttg actgcgatgg agatgaagca tcgcaatccc aggcgggctc    3071
taccaaagcc caagccaaaa cccaatgctc aacacagag accccctggt cggctgggcc    3131
gctggatcag gaccgtctct gatgaggacc ttgagtgagg ctcctgggag tctcccgaca    3191
ccacccgcgc aggtgtggac accaattcgg ccttacaaca tcccaaattg gatccgttcg    3251
cgggtcccct                                                          3261

<210> SEQ ID NO 4
<211> LENGTH: 145
<212> TYPE: PRT
<213> ORGANISM: Infectious bursal disease virus

<400> SEQUENCE: 4

Met Val Ser Arg Asp Gln Thr Asn Asp Arg Ser Asp Asp Lys Pro Ala
1               5                   10                  15

Arg Ser Asn Pro Thr Asp Cys Ser Val His Thr Glu Pro Ser Asp Ala
            20                  25                  30

Asn Asn Arg Thr Gly Val His Ser Gly Arg His Pro Gly Glu Ala His
        35                  40                  45

Ser Gln Val Arg Asp Leu Asp Leu Gln Phe Asp Cys Gly Gly His Arg
    50                  55                  60

Val Arg Ala Asn Cys Leu Phe Pro Trp Ile Pro Trp Leu Asn Cys Gly
65                  70                  75                  80

Cys Ser Leu His Thr Ala Gly Gln Trp Glu Leu Gln Val Arg Ser Asp
                85                  90                  95

Ala Pro Asp Cys Pro Glu Pro Thr Gly Gln Leu Gln Leu Leu Gln Ala
            100                 105                 110

Ser Glu Ser Glu Ser His Ser Glu Val Lys His Thr Ser Trp Trp Arg
        115                 120                 125

Leu Cys Thr Lys Arg His His Lys Arg Arg Asp Leu Pro Arg Lys Pro
    130                 135                 140

Glu
145

<210> SEQ ID NO 5
<211> LENGTH: 3261
<212> TYPE: DNA
<213> ORGANISM: Infectious bursal disease virus
```

```
<220> FEATURE:
<221> NAME/KEY: CDS
<222> LOCATION: (131)..(3166)

<400> SEQUENCE: 5
ggatacgatc ggtctgaccc cgggggagtc acccgggggac aggccgtcaa ggccttgttc      60
caggatggga ctcctccttc tacaacgcta tcattgatgg ttagtagaga tcagacaaac     120
gatcgcagcg atg aca aac ctg caa gat caa acc caa cag att gtt ccg        169
            Met Thr Asn Leu Gln Asp Gln Thr Gln Gln Ile Val Pro
              1               5                  10 ttc ata cgg agc ctt ctg atg cca aca acc gga ccg gcg tcc att ccg       217
Phe Ile Arg Ser Leu Leu Met Pro Thr Thr Gly Pro Ala Ser Ile Pro
 15                  20                  25 gac gac acc ctg gag aag cac act ctc agg tca gag acc tcg acc tac       265
Asp Asp Thr Leu Glu Lys His Thr Leu Arg Ser Glu Thr Ser Thr Tyr
 30                  35                  40                  45 aat ttg act gtg ggg gac aca ggg tca ggg cta att gtc ttt ttc cct       313
Asn Leu Thr Val Gly Asp Thr Gly Ser Gly Leu Ile Val Phe Phe Pro
                 50                  55                  60 gga ttc cct ggc tca att gtg ggt gct cac tac aca ctg cag ggc aat       361
Gly Phe Pro Gly Ser Ile Val Gly Ala His Tyr Thr Leu Gln Gly Asn
             65                  70                  75 ggg aac tac aag ttc gat cag atg ctc ctg act gcc cag aac cta ccg       409
Gly Asn Tyr Lys Phe Asp Gln Met Leu Leu Thr Ala Gln Asn Leu Pro
         80                  85                  90 gcc agt tac aac tac tgc agg cta gtg agt cgg agt ctc aca gtg agg       457
Ala Ser Tyr Asn Tyr Cys Arg Leu Val Ser Arg Ser Leu Thr Val Arg
     95                 100                 105 tca agc aca ctt cct ggt ggc gtt tat gca cta aac ggc acc ata aac       505
Ser Ser Thr Leu Pro Gly Gly Val Tyr Ala Leu Asn Gly Thr Ile Asn
110                 115                 120                 125 gcc gtg acc ttc caa gga agc ctg agt gaa ctg aca gat gtt agc tac       553
Ala Val Thr Phe Gln Gly Ser Leu Ser Glu Leu Thr Asp Val Ser Tyr
                130                 135                 140 aat ggg ttg atg tct gca aca gcc aac atc aac gac aaa att ggg aac       601
Asn Gly Leu Met Ser Ala Thr Ala Asn Ile Asn Asp Lys Ile Gly Asn
            145                 150                 155 gtc cta gta ggg gaa ggg gtc acc gtc ctc agc tta ccc aca tca tat       649
Val Leu Val Gly Glu Gly Val Thr Val Leu Ser Leu Pro Thr Ser Tyr
        160                 165                 170 gat ctt ggg tat gtg agg ctt ggt gac ccc att ccc gca ata ggg ctt       697
Asp Leu Gly Tyr Val Arg Leu Gly Asp Pro Ile Pro Ala Ile Gly Leu
    175                 180                 185 gac cca aaa atg gta gcc aca tgt gac agc agt gac agg ccc aga gtc       745
Asp Pro Lys Met Val Ala Thr Cys Asp Ser Ser Asp Arg Pro Arg Val
190                 195                 200                 205 tac acc ata act gca gcc gat gat tac caa ttc tca tca cag tac caa       793
Tyr Thr Ile Thr Ala Ala Asp Asp Tyr Gln Phe Ser Ser Gln Tyr Gln
                210                 215                 220 cca ggt ggg gta aca atc aca ctg ttc tca gcc aac att gat gcc atc       841
Pro Gly Gly Val Thr Ile Thr Leu Phe Ser Ala Asn Ile Asp Ala Ile
            225                 230                 235 aca agc ctc agc gtt ggg gga gag ctc gtg ttt caa aca agc gtc cac       889
Thr Ser Leu Ser Val Gly Gly Glu Leu Val Phe Gln Thr Ser Val His
        240                 245                 250 ggc ctt gta ctg ggc gcc acc atc tac ctc ata ggc ttt gat ggg aca       937
Gly Leu Val Leu Gly Ala Thr Ile Tyr Leu Ile Gly Phe Asp Gly Thr
    255                 260                 265
```

```
acg gta atc acc agg gct gtg gcc gca aac aat ggg ctg acg acc ggc     985
Thr Val Ile Thr Arg Ala Val Ala Ala Asn Asn Gly Leu Thr Thr Gly
270             275                 280                 285 acc gac aac ctt atg cca ttc aat ctt gtg att cca aca aac gag ata    1033
Thr Asp Asn Leu Met Pro Phe Asn Leu Val Ile Pro Thr Asn Glu Ile
                290                 295                 300 acc cag cca atc aca tcc atc aaa ctg gag ata gtg acc tcc aaa agt    1081
Thr Gln Pro Ile Thr Ser Ile Lys Leu Glu Ile Val Thr Ser Lys Ser
            305                 310                 315 ggt ggt cag gca ggg gat cag atg tca tgg tcg gca aga ggg agc cta    1129
Gly Gly Gln Ala Gly Asp Gln Met Ser Trp Ser Ala Arg Gly Ser Leu
        320                 325                 330 gca gtg acg atc cat ggt ggc aac tat cca ggg gcc ctc cgt ccc gtc    1177
Ala Val Thr Ile His Gly Gly Asn Tyr Pro Gly Ala Leu Arg Pro Val
    335                 340                 345 acg cta gtg gcc tac gaa aga gtg gca aca gga tcc gtc gtt acg gtc    1225
Thr Leu Val Ala Tyr Glu Arg Val Ala Thr Gly Ser Val Val Thr Val
350                 355                 360                 365 gct ggg gtg agc aac ttc gag ctg atc cca aat cct gaa cta gca aag    1273
Ala Gly Val Ser Asn Phe Glu Leu Ile Pro Asn Pro Glu Leu Ala Lys
                370                 375                 380 aac ctg gtt aca gaa tac ggc cga ttt gac cca gga gcc atg aac tac    1321
Asn Leu Val Thr Glu Tyr Gly Arg Phe Asp Pro Gly Ala Met Asn Tyr
            385                 390                 395 aca aaa ttg ata ctg agt gag agg gac cgt ctt ggc atc aag acc gtc    1369
Thr Lys Leu Ile Leu Ser Glu Arg Asp Arg Leu Gly Ile Lys Thr Val
        400                 405                 410 tgg cca aca agg gag tac act gac ttt cgt gaa tac ttc atg gag gtg    1417
Trp Pro Thr Arg Glu Tyr Thr Asp Phe Arg Glu Tyr Phe Met Glu Val
    415                 420                 425 gcc gac ctc aac tct ccc ctg aag att gca gga gca ttc ggc ttc aaa    1465
Ala Asp Leu Asn Ser Pro Leu Lys Ile Ala Gly Ala Phe Gly Phe Lys
430                 435                 440                 445 gac ata atc cgg gcc ata agg agg ata gct gtg ccg gtg gtc tcc aca    1513
Asp Ile Ile Arg Ala Ile Arg Arg Ile Ala Val Pro Val Val Ser Thr
                450                 455                 460 ttg ttc cca cct gcc gct ccc cta gcc cat gca att ggg gaa ggt gta    1561
Leu Phe Pro Pro Ala Ala Pro Leu Ala His Ala Ile Gly Glu Gly Val
            465                 470                 475 gac tac ctg ctg ggc gat gag gca cag gct gct tca gga act gct cga    1609
Asp Tyr Leu Leu Gly Asp Glu Ala Gln Ala Ala Ser Gly Thr Ala Arg
        480                 485                 490 gcc gcg tca gga aaa gca aga gct gcc tca ggc cgc ata agg cag ctg    1657
Ala Ala Ser Gly Lys Ala Arg Ala Ala Ser Gly Arg Ile Arg Gln Leu
    495                 500                 505 act ctc gcc gcc gac aag ggg tac gag gta gtc gcg aat cta ttc cag    1705
Thr Leu Ala Ala Asp Lys Gly Tyr Glu Val Val Ala Asn Leu Phe Gln
510                 515                 520                 525 gtg ccc cag aat ccc gta gtc gac ggg att ctt gct tca cct ggg gta    1753
Val Pro Gln Asn Pro Val Val Asp Gly Ile Leu Ala Ser Pro Gly Val
                530                 535                 540 ctc cgc ggt gca cac aac ctc gac tgc gtg tta aga gag ggt gcc acg    1801
Leu Arg Gly Ala His Asn Leu Asp Cys Val Leu Arg Glu Gly Ala Thr
            545                 550                 555 cta ttc cct gtg gtt att acg aca gtg gaa gac gcc atg aca ccc aaa    1849
Leu Phe Pro Val Val Ile Thr Thr Val Glu Asp Ala Met Thr Pro Lys
        560                 565                 570 gca ttg aac agc aaa atg ttt gct gtc att gaa ggc gtg cga gaa gac    1897
Ala Leu Asn Ser Lys Met Phe Ala Val Ile Glu Gly Val Arg Glu Asp
575                 580                 585
```

```
ctc caa cct cca tct caa aga gga tcc ttc ata cga act ctc tct gga    1945
Leu Gln Pro Pro Ser Gln Arg Gly Ser Phe Ile Arg Thr Leu Ser Gly
590             595                 600                 605 cac aga gtc tat gga tat gct cca gat ggg gta ctt cca ctg gag act    1993
His Arg Val Tyr Gly Tyr Ala Pro Asp Gly Val Leu Pro Leu Glu Thr
                610                 615                 620 ggg aga gac tac acc gtt gtc cca ata gat gat gtc tgg gac gac agc    2041
Gly Arg Asp Tyr Thr Val Val Pro Ile Asp Asp Val Trp Asp Asp Ser
            625                 630                 635 att atg ctg tcc aaa gat ccc ata cct cct att gtg gga aac agt gga    2089
Ile Met Leu Ser Lys Asp Pro Ile Pro Pro Ile Val Gly Asn Ser Gly
        640                 645                 650 aat cta gcc ata gct tac atg gat gtg ttt cga ccc aaa gtc cca atc    2137
Asn Leu Ala Ile Ala Tyr Met Asp Val Phe Arg Pro Lys Val Pro Ile
    655                 660                 665 cat gtg gct atg acg gga gcc ctc aat gct tgt ggc gag att gag aaa    2185
His Val Ala Met Thr Gly Ala Leu Asn Ala Cys Gly Glu Ile Glu Lys
670                 675                 680                 685 gta agc ttt aga agc acc aag ctc gcc act gca cac cga ctt ggc ctt    2233
Val Ser Phe Arg Ser Thr Lys Leu Ala Thr Ala His Arg Leu Gly Leu
                690                 695                 700 agg ttg gct ggt ccc gga gca ttc gat gta aac acc ggg ccc aac tgg    2281
Arg Leu Ala Gly Pro Gly Ala Phe Asp Val Asn Thr Gly Pro Asn Trp
            705                 710                 715 gca acg ttc atc aaa cgt ttc cct cac aat cca cgc gac tgg gac agg    2329
Ala Thr Phe Ile Lys Arg Phe Pro His Asn Pro Arg Asp Trp Asp Arg
        720                 725                 730 ctc ccc tac ctc aac cta cca tac ctt cca ccc aat gca gga cgc cag    2377
Leu Pro Tyr Leu Asn Leu Pro Tyr Leu Pro Pro Asn Ala Gly Arg Gln
    735                 740                 745 tac cac ctt gcc atg gct gca tca gag ttc aaa gag acc ccc gaa ctc    2425
Tyr His Leu Ala Met Ala Ala Ser Glu Phe Lys Glu Thr Pro Glu Leu
750                 755                 760                 765 gag agt gcc gtc aga gca atg gaa gca gca gcc aac gtg gac cca cta    2473
Glu Ser Ala Val Arg Ala Met Glu Ala Ala Ala Asn Val Asp Pro Leu
                770                 775                 780 ttc caa tct gca ctc agt gtg ttc atg tgg ctg gaa gag aat ggg att    2521
Phe Gln Ser Ala Leu Ser Val Phe Met Trp Leu Glu Glu Asn Gly Ile
            785                 790                 795 gtg act gac atg gcc aac ttc gca ctc agc gac ccg aac gcc cat cgg    2569
Val Thr Asp Met Ala Asn Phe Ala Leu Ser Asp Pro Asn Ala His Arg
        800                 805                 810 atg cga aat ttt ctt gca aac gca cca caa gca ggc agc aag tcg caa    2617
Met Arg Asn Phe Leu Ala Asn Ala Pro Gln Ala Gly Ser Lys Ser Gln
    815                 820                 825 agg gcc aag tac ggg aca gca ggc tac gga gtg gag gct cgg ggc ccc    2665
Arg Ala Lys Tyr Gly Thr Ala Gly Tyr Gly Val Glu Ala Arg Gly Pro
830                 835                 840                 845 aca cca gag gaa gca cag agg gaa aaa gac aca cgg atc tca aag aag    2713
Thr Pro Glu Glu Ala Gln Arg Glu Lys Asp Thr Arg Ile Ser Lys Lys
                850                 855                 860 atg gag acc atg ggc atc tac ttt gca aca cca gaa tgg gta gca ctc    2761
Met Glu Thr Met Gly Ile Tyr Phe Ala Thr Pro Glu Trp Val Ala Leu
            865                 870                 875 aat ggg cac cga ggg cca agc ccc ggc cag cta aag tac tgg cag aac    2809
Asn Gly His Arg Gly Pro Ser Pro Gly Gln Leu Lys Tyr Trp Gln Asn
        880                 885                 890 aca cga gaa ata ccg gac cca aac gag gac tat cta gac tac gtg cat    2857
Thr Arg Glu Ile Pro Asp Pro Asn Glu Asp Tyr Leu Asp Tyr Val His
    895                 900                 905
```

-continued

| | | | | | | | | | | | | | | |
|---|---|---|---|---|---|---|---|---|---|---|---|---|---|---|
| gca | gag | aag | agc | cgg | ttg | gca | tca | gaa | gaa | caa | atc | cta | agg | gca gct | 2905 |
| Ala | Glu | Lys | Ser | Arg | Leu | Ala | Ser | Glu | Glu | Gln | Ile | Leu | Arg | Ala Ala |
| 910 | | | | 915 | | | | | 920 | | | | | 925 |

```
gca gag aag agc cgg ttg gca tca gaa gaa caa atc cta agg gca gct     2905
Ala Glu Lys Ser Arg Leu Ala Ser Glu Glu Gln Ile Leu Arg Ala Ala
910             915                 920                 925 acg tcg atc tac ggg gct cca gga cag gca gag cca ccc caa gct ttc     2953
Thr Ser Ile Tyr Gly Ala Pro Gly Gln Ala Glu Pro Pro Gln Ala Phe
                930                 935                 940 ata gac gaa gtt gcc aaa gtc tat gaa atc aac cat gga cgt ggc cca     3001
Ile Asp Glu Val Ala Lys Val Tyr Glu Ile Asn His Gly Arg Gly Pro
            945                 950                 955 aac caa gaa cag atg aaa gat ctg ctc ttg act gcg atg gag atg aag     3049
Asn Gln Glu Gln Met Lys Asp Leu Leu Leu Thr Ala Met Glu Met Lys
        960                 965                 970 cat cgc aat ccc agg cgg gct cta cca aag ccc aag cca aaa ccc aat     3097
His Arg Asn Pro Arg Arg Ala Leu Pro Lys Pro Lys Pro Lys Pro Asn
    975                 980                 985 gct cca aca cag aga ccc cct ggt cgg ctg ggc cgc tgg atc agg acc     3145
Ala Pro Thr Gln Arg Pro Pro Gly Arg Leu Gly Arg Trp Ile Arg Thr
990                 995                 1000                1005 gtc tct gat gag gac ctt gag tgaggctcct gggagtctcc cgacaccacc        3196
Val Ser Asp Glu Asp Leu Glu
                1010 cgcgcaggtg tggacaccaa ttcggcctta caacatccca aattggatcc gttcgcgggt   3256 ccct                                                                3261

<210> SEQ ID NO 6
<211> LENGTH: 1012
<212> TYPE: PRT
<213> ORGANISM: Infectious bursal disease virus

<400> SEQUENCE: 6

Met Thr Asn Leu Gln Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Gly Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205
```

-continued

```
Thr Ala Ala Asp Asp Tyr Gln Phe Ser Ser Gln Tyr Gln Pro Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Gln Thr Ser Val His Gly Leu Val
                245                 250                 255

Leu Gly Ala Thr Ile Tyr Leu Ile Gly Phe Asp Gly Thr Thr Val Ile
            260                 265                 270

Thr Arg Ala Val Ala Ala Asn Asn Gly Leu Thr Thr Gly Thr Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Glu Ile Val Thr Ser Lys Ser Gly Gly Gln
305                 310                 315                 320

Ala Gly Asp Gln Met Ser Trp Ser Ala Arg Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
        435                 440                 445

Arg Ala Ile Arg Arg Ile Ala Val Pro Val Val Ser Thr Leu Phe Pro
    450                 455                 460

Pro Ala Ala Pro Leu Ala His Ala Ile Gly Glu Gly Val Asp Tyr Leu
465                 470                 475                 480

Leu Gly Asp Glu Ala Gln Ala Ala Ser Gly Thr Ala Arg Ala Ala Ser
                485                 490                 495

Gly Lys Ala Arg Ala Ala Ser Gly Arg Ile Arg Gln Leu Thr Leu Ala
            500                 505                 510

Ala Asp Lys Gly Tyr Glu Val Val Ala Asn Leu Phe Gln Val Pro Gln
        515                 520                 525

Asn Pro Val Val Asp Gly Ile Leu Ala Ser Pro Gly Val Leu Arg Gly
    530                 535                 540

Ala His Asn Leu Asp Cys Val Leu Arg Glu Gly Ala Thr Leu Phe Pro
545                 550                 555                 560

Val Val Ile Thr Thr Val Glu Asp Ala Met Thr Pro Lys Ala Leu Asn
                565                 570                 575

Ser Lys Met Phe Ala Val Ile Glu Gly Val Arg Glu Asp Leu Gln Pro
            580                 585                 590

Pro Ser Gln Arg Gly Ser Phe Ile Arg Thr Leu Ser Gly His Arg Val
        595                 600                 605

Tyr Gly Tyr Ala Pro Asp Gly Val Leu Pro Leu Glu Thr Gly Arg Asp
    610                 615                 620
```

-continued

```
Tyr Thr Val Val Pro Ile Asp Asp Val Trp Asp Asp Ser Ile Met Leu
625                 630                 635                 640

Ser Lys Asp Pro Ile Pro Ile Val Gly Asn Ser Gly Asn Leu Ala
            645                 650                 655

Ile Ala Tyr Met Asp Val Phe Arg Pro Lys Val Pro Ile His Val Ala
            660                 665                 670

Met Thr Gly Ala Leu Asn Ala Cys Gly Glu Ile Glu Lys Val Ser Phe
            675                 680                 685

Arg Ser Thr Lys Leu Ala Thr Ala His Arg Leu Gly Leu Arg Leu Ala
            690                 695                 700

Gly Pro Gly Ala Phe Asp Val Asn Thr Gly Pro Asn Trp Ala Thr Phe
705                 710                 715                 720

Ile Lys Arg Phe Pro His Asn Pro Arg Asp Trp Asp Arg Leu Pro Tyr
                725                 730                 735

Leu Asn Leu Pro Tyr Leu Pro Pro Asn Ala Gly Arg Gln Tyr His Leu
                740                 745                 750

Ala Met Ala Ala Ser Glu Phe Lys Glu Thr Pro Glu Leu Glu Ser Ala
                755                 760                 765

Val Arg Ala Met Glu Ala Ala Ala Asn Val Asp Pro Leu Phe Gln Ser
770                 775                 780

Ala Leu Ser Val Phe Met Trp Leu Glu Glu Asn Gly Ile Val Thr Asp
785                 790                 795                 800

Met Ala Asn Phe Ala Leu Ser Asp Pro Asn Ala His Arg Met Arg Asn
                805                 810                 815

Phe Leu Ala Asn Ala Pro Gln Ala Gly Ser Lys Ser Gln Arg Ala Lys
                820                 825                 830

Tyr Gly Thr Ala Gly Tyr Gly Val Glu Ala Arg Gly Pro Thr Pro Glu
                835                 840                 845

Glu Ala Gln Arg Glu Lys Asp Thr Arg Ile Ser Lys Lys Met Glu Thr
                850                 855                 860

Met Gly Ile Tyr Phe Ala Thr Pro Glu Trp Val Ala Leu Asn Gly His
865                 870                 875                 880

Arg Gly Pro Ser Pro Gly Gln Leu Lys Tyr Trp Gln Asn Thr Arg Glu
                885                 890                 895

Ile Pro Asp Pro Asn Glu Asp Tyr Leu Asp Tyr Val His Ala Glu Lys
                900                 905                 910

Ser Arg Leu Ala Ser Glu Glu Gln Ile Leu Arg Ala Ala Thr Ser Ile
                915                 920                 925

Tyr Gly Ala Pro Gly Gln Ala Glu Pro Pro Gln Ala Phe Ile Asp Glu
                930                 935                 940

Val Ala Lys Val Tyr Glu Ile Asn His Gly Arg Gly Pro Asn Gln Glu
945                 950                 955                 960

Gln Met Lys Asp Leu Leu Leu Thr Ala Met Glu Met Lys His Arg Asn
                965                 970                 975

Pro Arg Arg Ala Leu Pro Lys Pro Lys Pro Lys Pro Asn Ala Pro Thr
                980                 985                 990

Gln Arg Pro Pro Gly Arg Leu Gly Arg Trp Ile Arg Thr Val Ser Asp
                995                1000                1005

Glu Asp Leu Glu
    1010
```

```
<210> SEQ ID NO 7
<211> LENGTH: 162
<212> TYPE: DNA
<213> ORGANISM: Infectious bursal disease virus
<220> FEATURE:
<221> NAME/KEY: CDS
<222> LOCATION: (97)..(162)

<400> SEQUENCE: 7
ggatacgatc ggtctgaccc cggggagtc acccggggac aggccgtcaa ggccttgttc        60
caggatggga ctcctccttc tacaacgcta tcattc gaa gtt agt tga gat ctg       114
                                         Glu Val Ser     Asp Leu
                                           1              5 aca aac gat cgc agc gat gac aaa cct gca aga tca aac cca aca gat      162
Thr Asn Asp Arg Ser Asp Asp Lys Pro Ala Arg Ser Asn Pro Thr Asp
         10                  15                  20

<210> SEQ ID NO 8
<211> LENGTH: 2827
<212> TYPE: DNA
<213> ORGANISM: Infectious bursal disease virus
<220> FEATURE:
<221> NAME/KEY: CDS
<222> LOCATION: (112)..(2745)

<400> SEQUENCE: 8
ggatacgatg gtctgaccc tctgggagtc acgaattaac gtggctacta ggggcgatac        60
ccgccgctgg ctgccacgtt agtggctcct cttcttgatg attctgccac c atg agt     117
                                                          Met Ser
                                                            1 gac att ttc aac agt cca cag gcg cga agc acg atc tca gca gcg ttc      165
Asp Ile Phe Asn Ser Pro Gln Ala Arg Ser Thr Ile Ser Ala Ala Phe
          5                  10                  15 ggc ata aag cct act gct gga caa gac gtg gaa gaa ctc ttg atc cct      213
Gly Ile Lys Pro Thr Ala Gly Gln Asp Val Glu Glu Leu Leu Ile Pro
         20                  25                  30 aaa gtt tgg gtg cca cct gag gat ccg ctt gcc agc cct agt cga ctg      261
Lys Val Trp Val Pro Pro Glu Asp Pro Leu Ala Ser Pro Ser Arg Leu
35                  40                  45                  50 gca aag ttc ctc aga gag aac ggc tac aaa gtt ttg cag ccg cgg tct      309
Ala Lys Phe Leu Arg Glu Asn Gly Tyr Lys Val Leu Gln Pro Arg Ser
                 55                  60                  65 ctg ccc gag aat gag gag tat gag acc gac caa ata ctc cca gac tta      357
Leu Pro Glu Asn Glu Glu Tyr Glu Thr Asp Gln Ile Leu Pro Asp Leu
             70                  75                  80 gca tgg atg cga cag ata gaa ggg gct gtt tta aaa ccc act cta tct      405
Ala Trp Met Arg Gln Ile Glu Gly Ala Val Leu Lys Pro Thr Leu Ser
         85                  90                  95 ctc cct att gga gat cag gag tac ttc cca aag tac tac cca aca cat      453
Leu Pro Ile Gly Asp Gln Glu Tyr Phe Pro Lys Tyr Tyr Pro Thr His
        100                 105                 110 cgc cct agc aag gag aag ccc aat gcg tac ccg cca gac atc gca cta      501
Arg Pro Ser Lys Glu Lys Pro Asn Ala Tyr Pro Pro Asp Ile Ala Leu
115                 120                 125                 130 ctc aag cag atg att tac ctg ttt ctc cag gtt cca gag gcc aac gag      549
Leu Lys Gln Met Ile Tyr Leu Phe Leu Gln Val Pro Glu Ala Asn Glu
                135                 140                 145 ggc cta aag gat gaa gta acc ctc ttg acc caa aac ata agg gac aag      597
Gly Leu Lys Asp Glu Val Thr Leu Leu Thr Gln Asn Ile Arg Asp Lys
            150                 155                 160
```

```
                                                      -continued gcc tat gga agt ggg acc tac atg gga caa gca act cga ctt gtg gcc      645
Ala Tyr Gly Ser Gly Thr Tyr Met Gly Gln Ala Thr Arg Leu Val Ala
        165                 170                 175 atg aag gag gtc gcc act gga aga aac cca aac aag gat cct cta aag      693
Met Lys Glu Val Ala Thr Gly Arg Asn Pro Asn Lys Asp Pro Leu Lys
    180                 185                 190 ctt ggg tac act ttt gag agc atc gcg cag cta ctt gac atc aca cta      741
Leu Gly Tyr Thr Phe Glu Ser Ile Ala Gln Leu Leu Asp Ile Thr Leu
195                 200                 205                 210 ccg gta ggc cca ccc ggt gag gat gac aag ccc tgg gtg cca ctc aca      789
Pro Val Gly Pro Pro Gly Glu Asp Asp Lys Pro Trp Val Pro Leu Thr
                215                 220                 225 aga gtg ccg tca cgg atg ttg gtg ctg acg gga gac gta gat ggc gac      837
Arg Val Pro Ser Arg Met Leu Val Leu Thr Gly Asp Val Asp Gly Asp
            230                 235                 240 ttt gag gtt gaa gat tac ctt ccc aaa atc aac ctc aag tca tca agt      885
Phe Glu Val Glu Asp Tyr Leu Pro Lys Ile Asn Leu Lys Ser Ser Ser
        245                 250                 255 gga cta cca tat gta ggt cgc acc aaa gga gag aca att ggc gag atg      933
Gly Leu Pro Tyr Val Gly Arg Thr Lys Gly Glu Thr Ile Gly Glu Met
    260                 265                 270 ata gct ata tca aac cag ttt ctc aga gag cta tca aca ctg ttg aag      981
Ile Ala Ile Ser Asn Gln Phe Leu Arg Glu Leu Ser Thr Leu Leu Lys
275                 280                 285                 290 caa ggt gca ggg aca aag ggg tca aac aag aag aag cta ctc agc atg     1029
Gln Gly Ala Gly Thr Lys Gly Ser Asn Lys Lys Lys Leu Leu Ser Met
                295                 300                 305 tta agt gac tat tgg tac tta tca tgc ggg ctt ttg ttt cca aag gct     1077
Leu Ser Asp Tyr Trp Tyr Leu Ser Cys Gly Leu Leu Phe Pro Lys Ala
            310                 315                 320 gaa agg tac gac aaa agt aca tgg ctc acc aag acc cgg aac ata tgg     1125
Glu Arg Tyr Asp Lys Ser Thr Trp Leu Thr Lys Thr Arg Asn Ile Trp
        325                 330                 335 tca gct cca tcc cca aca cac ctc atg atc tcc atg atc acc tgg ccc     1173
Ser Ala Pro Ser Pro Thr His Leu Met Ile Ser Met Ile Thr Trp Pro
    340                 345                 350 gtg atg tcc aac agc cca aat aac gtg ttg aac att gaa ggg tgt cca     1221
Val Met Ser Asn Ser Pro Asn Asn Val Leu Asn Ile Glu Gly Cys Pro
355                 360                 365                 370 tca ctc tac aaa ttc aac ccg ttc aga gga ggg ttg aac agg atc gtc     1269
Ser Leu Tyr Lys Phe Asn Pro Phe Arg Gly Gly Leu Asn Arg Ile Val
                375                 380                 385 gag tgg ata ttg gcc ccg gaa gaa ccc aag gct ctt gta tat gcg gac     1317
Glu Trp Ile Leu Ala Pro Glu Glu Pro Lys Ala Leu Val Tyr Ala Asp
            390                 395                 400 aac ata tac att gtc cac tca aac acg tgg tac tca att gac cta gag     1365
Asn Ile Tyr Ile Val His Ser Asn Thr Trp Tyr Ser Ile Asp Leu Glu
        405                 410                 415 aag ggt gag gca aac tgc act cgc caa cac atg caa gcc gca atg tac     1413
Lys Gly Glu Ala Asn Cys Thr Arg Gln His Met Gln Ala Ala Met Tyr
    420                 425                 430 tac ata ctc acc aga ggg tgg tca gac aac ggc gac cca atg ttc aat     1461
Tyr Ile Leu Thr Arg Gly Trp Ser Asp Asn Gly Asp Pro Met Phe Asn
435                 440                 445                 450 caa aca tgg gcc acc ttt gcc atg aac att gcc cct gct cta gtg gtg     1509
Gln Thr Trp Ala Thr Phe Ala Met Asn Ile Ala Pro Ala Leu Val Val
                455                 460                 465 gac tca tcg tgc ctg ata atg aac ctg caa att aag acc tat ggt caa     1557
Asp Ser Ser Cys Leu Ile Met Asn Leu Gln Ile Lys Thr Tyr Gly Gln
            470                 475                 480
```

```
ggc agc ggg aat gca gcc acg ttc atc aac aac cac ctc ttg agc acg      1605
Gly Ser Gly Asn Ala Ala Thr Phe Ile Asn Asn His Leu Leu Ser Thr
            485                 490                 495 cta gtg ctt gac cag tgg aac ttg atg aga cag ccc aga cca gac agc      1653
Leu Val Leu Asp Gln Trp Asn Leu Met Arg Gln Pro Arg Pro Asp Ser
500                 505                 510 gag gag ttc aaa tca att gag gac aag cta ggt atc aac ttt aag att      1701
Glu Glu Phe Lys Ser Ile Glu Asp Lys Leu Gly Ile Asn Phe Lys Ile
515                 520                 525                 530 gag agg tcc att gat gat atc agg ggc aag ctg aga cag ctt gtc ctc      1749
Glu Arg Ser Ile Asp Asp Ile Arg Gly Lys Leu Arg Gln Leu Val Leu
                535                 540                 545 ctt gca caa cca ggg tac ctg agt ggg ggt gtt gaa cca gaa caa tcc      1797
Leu Ala Gln Pro Gly Tyr Leu Ser Gly Gly Val Glu Pro Glu Gln Ser
            550                 555                 560 agc cca act gtt gag ctt gac cta cta ggg tgg tca gct aca tac agc      1845
Ser Pro Thr Val Glu Leu Asp Leu Leu Gly Trp Ser Ala Thr Tyr Ser
        565                 570                 575 aaa gat ctc ggg atc tat gtg ccg gtg ctt gac aag gaa cgc cta ttt      1893
Lys Asp Leu Gly Ile Tyr Val Pro Val Leu Asp Lys Glu Arg Leu Phe
580                 585                 590 tgt tct gct gcg tat ccc aag gga gta gag aac aag agt ctc aag tcc      1941
Cys Ser Ala Ala Tyr Pro Lys Gly Val Glu Asn Lys Ser Leu Lys Ser
595                 600                 605                 610 aaa gtc ggg atc gag cag gca tac aag gta gtc agg tat gag gcg ttg      1989
Lys Val Gly Ile Glu Gln Ala Tyr Lys Val Val Arg Tyr Glu Ala Leu
                615                 620                 625 agg ttg gta ggt ggt tgg aac tac cca ctc ctg aac aaa gcc tgc aag      2037
Arg Leu Val Gly Gly Trp Asn Tyr Pro Leu Leu Asn Lys Ala Cys Lys
            630                 635                 640 aat aac gca ggc gcc gct cgg cgg cat ctg gag gcc aag ggg ttc cca      2085
Asn Asn Ala Gly Ala Ala Arg Arg His Leu Glu Ala Lys Gly Phe Pro
        645                 650                 655 ctc gac gag ttc cta gcc gag tgg tct gag ctg tca gag ttc ggt gag      2133
Leu Asp Glu Phe Leu Ala Glu Trp Ser Glu Leu Ser Glu Phe Gly Glu
660                 665                 670 gcc ttc gaa ggc ttc aat atc aag ctg acc gta aca tct gag agc cta      2181
Ala Phe Glu Gly Phe Asn Ile Lys Leu Thr Val Thr Ser Glu Ser Leu
675                 680                 685                 690 gcc gaa ctg aac aag cca gta ccc ccc aag ccc cca aat gtc aac aga      2229
Ala Glu Leu Asn Lys Pro Val Pro Pro Lys Pro Pro Asn Val Asn Arg
                695                 700                 705 cca gtc aac act ggg gga ctc aag gca gtc agc aac gcc ctc aag acc      2277
Pro Val Asn Thr Gly Gly Leu Lys Ala Val Ser Asn Ala Leu Lys Thr
            710                 715                 720 ggt cgg tac agg aac gaa gcc gga ctg agt ggt ctc gtc ctt cta gcc      2325
Gly Arg Tyr Arg Asn Glu Ala Gly Leu Ser Gly Leu Val Leu Leu Ala
        725                 730                 735 aca gca aga agc cgt ctg caa gat gca gtt aag gcc aag gca gaa gcc      2373
Thr Ala Arg Ser Arg Leu Gln Asp Ala Val Lys Ala Lys Ala Glu Ala
740                 745                 750 gag aaa ctc cac aag tcc aag cca gac gac ccc gat gca gac tgg ttc      2421
Glu Lys Leu His Lys Ser Lys Pro Asp Asp Pro Asp Ala Asp Trp Phe
755                 760                 765                 770 gaa aga tca gaa act ctg tca gac ctt ctg gag aaa gcc gac atc gcc      2469
Glu Arg Ser Glu Thr Leu Ser Asp Leu Leu Glu Lys Ala Asp Ile Ala
                775                 780                 785 agc aag gtc gcc cac tca gca ctc gtg gaa aca agc gac gcc ctt gaa      2517
Ser Lys Val Ala His Ser Ala Leu Val Glu Thr Ser Asp Ala Leu Glu
            790                 795                 800
```

-continued

| | | | | | | | | | | | | | | |
|---|---|---|---|---|---|---|---|---|---|---|---|---|---|---|
| gca | gtt | cag | tcg | act | tcc | gtg | tac | acc | ccc | aag | tac | cca | gaa | gtc | aag | 2565 |
| Ala | Val | Gln | Ser | Thr | Ser | Val | Tyr | Thr | Pro | Lys | Tyr | Pro | Glu | Val | Lys |
| | 805 | | | | 810 | | | | | 815 | | | | | | aac cca cag acc gcc tcc aac ccc gtt gtt ggg ctc cac ctg ccc gcc 2613
Asn Pro Gln Thr Ala Ser Asn Pro Val Val Gly Leu His Leu Pro Ala
  820                 825                 830 aag aga gcc acc ggt gtc cag gcc gct ctt ctc gga gca gga acg agc 2661
Lys Arg Ala Thr Gly Val Gln Ala Ala Leu Leu Gly Ala Gly Thr Ser
835                 840                 845                 850 aga cca atg ggg atg gag gcc cca aca cgg tcc aag aac gcc gtg aaa 2709
Arg Pro Met Gly Met Glu Ala Pro Thr Arg Ser Lys Asn Ala Val Lys
        855                 860                 865 atg gcc aaa cgg cgg caa cgc caa aag gag agc cgc taacagccat 2755
Met Ala Lys Arg Arg Gln Arg Gln Lys Glu Ser Arg
        870                 875 gatgggaacc actcaagaag aggacactaa tcccagaccc cgtatccccg gccttcgcct    2815
gcgggggccc cc    2827

<210> SEQ ID NO 9
<211> LENGTH: 44
<212> TYPE: DNA
<213> ORGANISM: Artificial
<220> FEATURE:
<223> OTHER INFORMATION: primer: A1F5'

<400> SEQUENCE: 9
agagaattct aatacgactc actataggat acgatcggtc tgac    44

<210> SEQ ID NO 10
<211> LENGTH: 25
<212> TYPE: DNA
<213> ORGANISM: Artificial
<220> FEATURE:
<223> OTHER INFORMATION: primer: A2R

<400> SEQUENCE: 10
tgggcctgtc actgctgtca catgt    25

<210> SEQ ID NO 11
<211> LENGTH: 25
<212> TYPE: DNA
<213> ORGANISM: Artificial
<220> FEATURE:
<223> OTHER INFORMATION: primer: A3R

<400> SEQUENCE: 11
cattgctctg cagtgtgtag tgagc    25

<210> SEQ ID NO 12
<211> LENGTH: 30
<212> TYPE: DNA
<213> ORGANISM: Artificial
<220> FEATURE:
<223> OTHER INFORMATION: primer: VP5MutF

<400> SEQUENCE: 12
ctacaacgct atccttaagg gttagtagag    30

<210> SEQ ID NO 13
<211> LENGTH: 30
<212> TYPE: DNA
<213> ORGANISM: Artificial

-continued

```
<220> FEATURE:
<223> OTHER INFORMATION: primer: VP5MutR

<400> SEQUENCE: 13
ctctactaac ccttaaggat agcgttgtag                                          30
```